United States Patent [19]

Daggett et al.

[11] Patent Number: 5,521,297
[45] Date of Patent: May 28, 1996

[54] NUCLEIC ACIDS ENCODING HUMAN METABOTROPIC GLUTAMATE RECEPTORS

[75] Inventors: Lorrie Daggett; Steven B. Ellis; Chen Liaw, all of San Diego; Aaron Pontsler, Santee, all of Calif.

[73] Assignee: Salk Institute Biotechnology/Industrial Associates, La Jolla, Calif.

[21] Appl. No.: 72,574

[22] Filed: Jun. 4, 1993

[51] Int. Cl.⁶ .......................... C07H 21/02; C12N 5/10; C12N 15/79; C12N 15/85
[52] U.S. Cl. .................. 536/23.5; 435/240.1; 435/320.1
[58] Field of Search .................. 536/23.1, 23.5; 435/240.2, 320.1

[56] References Cited

U.S. PATENT DOCUMENTS 5,385,831  1/1995  Mulvihill et al. .................... 435/69.1

FOREIGN PATENT DOCUMENTS

WO92/10583  6/1992  WIPO.

OTHER PUBLICATIONS

Daggett et al., "Cloning and Functional Expression of the Human Metabotropic mGluR5 Receptor" *Abstract:* International Meeting on Metabotropic Glutamate Receptors; Taurmina, Italy, Sep. 19–23, 1993.
Daggett et al., "Cloning and Functional Expression of the Human Metabotropic mGluR5 Receptor" *Abstract:* First Meeting of Turkish Society For Neuroscience; Izmir, Turkey, Oct. 12–14, 1993.
Daggett et al., "Cloning and Functional Expression of the Human Metabotropic mGluR5 Receptor" *Abstract:* 1993 Annual Meeting, Washington, DC, Nov. 7–12, 1993.
Gabellini et al., "Carboxyl domain of glutamate receptor directs its coupling to metabolic pathways" *NeuroReport* 9:531–534 (1993).
Minakami et al., "Molecular Cloning and the Functional Expression of Two Isoforms of Human Metabotropic Glutamate Receptor Subtype 5" *Biochem. and Biophysical Research Communications* 199(3):1136–1143 (1994).

Pickering et al., "A Comparison of Two Alternatively Spliced Forms of a Metabotropic Glutamate Receptor Coupled to Phosphoinositide Turnover" *Journal of Neurochemistry* 61(1):85–92 (1993).
Pin et al., "Domains involved in the specificity of G protein activation in phospholipase C—coupled metabotropic glutamate receptors" *EMBO Journal* 13(2):342–348 (1994).
Schoepp and Conn, "Metabotropic glutamate receptors in brain function and pathology" *TIPS* 14:13–19 (1993).
Takahashi et al., "Role of the Large Extracellular Domain of Metabotropic Glutamate Receptors in Agonist Selectivity Determination" *The Journal of Biological Chemistry* 268(26):19341–19345 (1993).
Testa et al., "Metabotropic Glutamate Receptor mRNA Expression in the Basal Ganglia of the Rat" *The Journal of Neuroscience* 14(5):3005–3018 (1994).
Houamed et al., Science 252:1318–1321 (31 May 1991).
Masu et al., Nature 349:760–765 (28 Feb. 1991).

*Primary Examiner*—Stephanie W. Zitomer
*Attorney, Agent, or Firm*—Pretty Schroeder Brueggemann & Clark; Stephen E. Reiter

[57] ABSTRACT

In accordance with the present invention, there are provided nucleic acids encoding human metabotropic glutamate receptor subtypes and the proteins encoded thereby. In a particular embodiment, the invention nucleic acids encode mGluR1, mGluR2, mGluR3 and mGluR5 subtypes of human metabotropic glutamate receptors. In addition to being useful for the production of metabotropic glutamate receptor subtypes, these nucleic acids are also useful as probes, thus enabling those skilled in the art, without undue experimentation, to identify and isolate related human receptor subunits. In addition to disclosing novel metabotropic glutamate receptor subtypes, the present invention also comprises methods for using such receptor subtypes to identify and characterize compounds which affect the function of such receptors, e.g., agonists, antagonists, and modulators of glutamate receptor function.

24 Claims, 1 Drawing Sheet

NUCLEIC ACIDS ENCODING HUMAN METABOTROPIC GLUTAMATE RECEPTORS

The present invention relates to nucleic acids and receptor proteins encoded thereby. Invention nucleic acids encode novel human metabotropic glutamate receptor subtypes. The invention also relates to methods for making such receptor subtypes and for using the receptor proteins in assays designed to identify and characterize compounds which affect the function of such receptors, e.g., agonists, antagonists, and allosteric modulators of human metabotropic glutamate receptors.

BACKGROUND OF THE INVENTION

The amino acid L-glutamate is a major excitatory neurotransmitter in the mammalian central nervous system. Anatomical, biochemical and electrophysiological analyses suggest that glutamatergic systems are involved in a broad array of neuronal processes, including fast excitatory synaptic transmission, regulation of neurotransmitter releases, long-term potentiation, learning and memory, developmental synaptic plasticity, hypoxic-ischemic damage and neuronal cell death, epileptiform seizures, as well as the pathogenesis of several neurodegenerative disorders. See generally, Monaghan et al., Ann. Rev. Pharmacol. Toxicol. 29:365–402 (1980). This extensive repertoire of functions, especially those related to learning, neurotoxicity and neuropathology, has stimulated recent attempts to describe and define the mechanisms through which glutamate exerts its effects.

Currently, glutamate receptor classification schemes are based on pharmacological criteria. Glutamate has been observed to mediate its effects through receptors that have been categorized into two main groups: ionotropic and metabotropic. Ionotropic glutamate receptors contain integral cation-specific, ligand-gated ion channels, whereas metabotropic glutamate receptors are G-protein-coupled receptors that transduce extracellular signals via activation of intracellular second messenger systems. Ionotropic receptors are further divided into at least two categories based on the pharmacological and functional properties of the receptors. The two main types of ionotropic receptors are NMDA (N-methyl-D-aspartate) receptors and kainate/AMPA ($\alpha$-amino-3-hydroxy-5-methyl-4-isoxazole propionate, formally called the quisqualic acid or QUIS receptor), receptors. While the metabotropic receptors bind to some of the same ligands that bind to ionotropic glutamate receptors, the metabotropic receptors alter synaptic physiology via GTP-binding proteins and second messengers such as cyclic AMP, cyclic GMP, diacylglycerol, inositol 1,4,5-triphosphate and calcium [see, for example, Gundersen et al., Proc. R. Soc. London Ser. 221:127 (1984); Sladeczek et al., Nature 317:717 (1985); Nicoletti et al., J. Neurosci. 6:1905 (1986); Sugiyama et al., Nature 325:531 (1987)].

The electrophysiological and pharmacological properties of metabotropic glutamate receptors have been studied using animal tissues and cell lines as a source of receptors, as well as non-human recombinant receptors. The value of such studies for application to the development of human therapeutics has been limited by the availability of only non-human receptors. Moreover, it is only recently that the characteristics and structure of metabotropic glutamate receptors have been investigated at the molecular level. Such investigation has, however, only been carried out in non-human species. Because of the potential physiological and pathological significance of metabotropic glutamate receptors, it is imperative (particularly for drug screening assays) to have available human sequences (i.e., DNA, RNA, proteins) which encode representative members of the various glutamate receptor classes. The availability of such human sequences will also enable the investigation of receptor distribution in humans, the correlation of specific receptor modification with the occurrence of various disease states, etc.

BRIEF DESCRIPTION OF THE INVENTION

The present invention discloses novel nucleic acids encoding human metabotropic glutamate receptor protein subtypes and the proteins encoded thereby. In a particular embodiment the novel nucleic acids encode full-length mGluR1, mGluR2, mGluR3 and mGluR5 subtypes of human metabotropic glutamate receptors, or portions thereof. In addition to being useful for the production of metabotropic glutamate receptor subtype proteins, these nucleic acids are also useful as probes, thus enabling those skilled in the art, without undue experimentation, to identify and isolate nucleic acids encoding related receptor subtypes.

In addition to disclosing novel metabotropic glutamate receptor protein subtypes, the present invention also comprises methods for using such receptor subtypes to identify and characterize compounds which affect the function of such receptors, e.g., agonists, antagonists, and modulators of glutamate receptor function. The invention also comprises methods for determining whether unknown protein(s) are functional as metabotropic glutamate receptor subtypes.

DETAILED DESCRIPTION OF THE INVENTION

Figure 1:
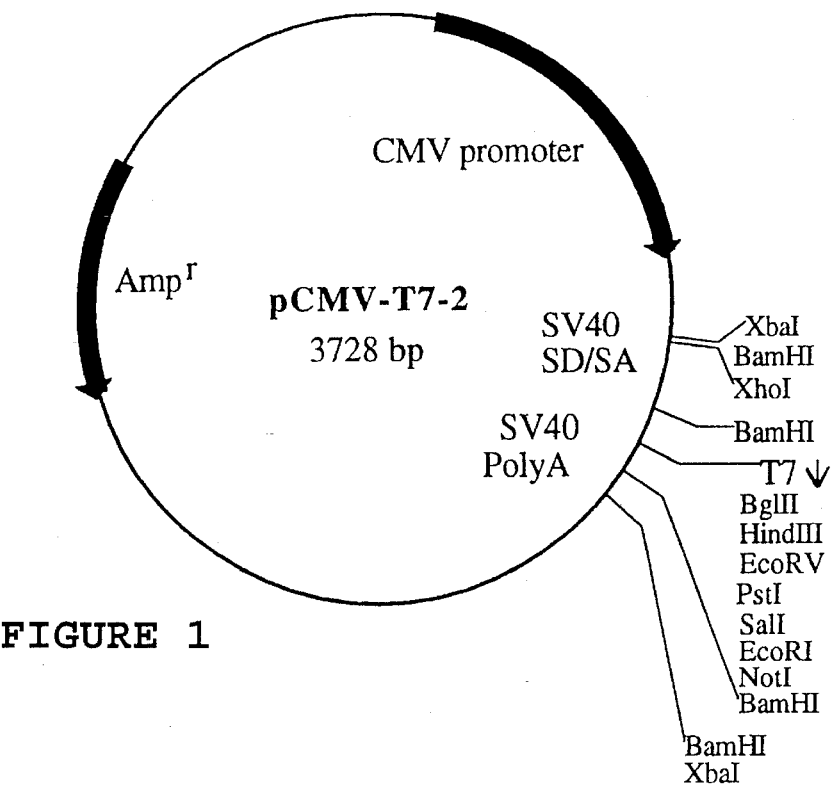
FIG. 1 presents a restriction map of the CMV promoter based vector, pCMV-T7-2.

In accordance with the present invention, there are provided isolated nucleic acids encoding human metabotropic glutamate receptor subtypes. In one aspect of the present invention, nucleic acids encoding human metabotropic glutamate receptors of the mGluR1 subtype are provided. In another aspect, nucleic acids encoding at least a portion of metabotropic glutamate receptors of the mGluR2 subtype are provided. In yet another aspect, nucleic acids encoding metabotropic glutamate receptors of the mGluR3 subtype are provided. In a further aspect, nucleic acids encoding metabotropic glutamate receptors of the mGluR5 subtype are provided. In a still further aspect, eukaryotic cells containing such nucleic acids, and eukaryotic cells expressing such nucleic acids are provided.

Also provided are protein(s) encoded by the above-described nucleic acids, as well as antibodies generated against the protein(s). In other aspects of the present invention, there are provided nucleic acid probes comprising metabotropic glutamate receptor subtype-selective portions of the above-described nucleic acids.

As employed herein, the phrase "human metabotropic glutamate receptor subtypes" refers to isolated and/or purified proteins which participate in the G-protein-coupled response of cells to glutamatergic ligands. Such receptor subtypes are individually encoded by distinct genes which do not encode other metabotropic glutamate receptor subtypes (i.e., each subtype is encoded by a unique gene). Such receptor subtypes are typically characterized by having seven putative transmembrane domains, preceded by a large extracellular amino-terminal domain and followed by a large intracellular carboxy-terminal domain. Metabotropic glutamate receptors share essentially no amino acid sequence homology with other G-protein-coupled receptors that are not metabotropic glutamate receptors.

Regarding the inter-relationship between each of the metabotropic glutamate receptor subtypes, the amino acid sequences of mGluR1 receptor subtypes are generally less than about 70% identical to the amino acid sequences of other human metabotropic glutamate receptor subtypes, with identities less than about 45% typically observed. The amino acid sequences of mGluR2 receptor subtypes are generally less than 60% identical to the amino acid sequences of other human metabotropic glutamate receptor subtypes, with identities of less than 45% typically observed. The amino acid sequences of mGluR3 receptor subtypes are generally less than 60% identical to the amino acid sequences of other human metabotropic glutamate receptor subtypes, with identities of less than 45% typically observed. The amino acid sequences of mGluR5 receptor subtypes are generally less than 70% identical to the amino acid sequences of other human metabotropic glutamate receptor subtypes, with identities of less than 45% typically observed.

Also included within the above definition are variants thereof encoded by mRNA generated by alternative splicing of a primary transcript, as well as fragments thereof which retain one or more of the above physiological and/or physical properties.

Use of the terms "isolated" or "purified" in the present specification and claims as a modifier of DNA, RNA, polypeptides or proteins means that the DNA, RNA, polypeptides or proteins so designated have been produced in such form by the hand of man, and thus are separated from their native in vivo cellular environment. As a result of this human intervention, the recombinant DNAs, RNAs, polypeptides and proteins of the invention are useful in ways that the DNAs, RNAs, polypeptides or proteins as they naturally occur are not, such as identification of selective drugs or compounds.

The term "functional" when used herein as a modifier of receptor protein(s) of the present invention, means that binding of glutamatergic ligands (such as ACPD or ACPD-like ligands, QUIS, AP4, and the like) to said receptor protein(s) modifies the receptor interaction with G-proteins, which in turn affects the levels of intracellular second messengers, leading to a variety of physiological effects. Stated another way, "functional" means that a signal is generated as a consequence of agonist activation of receptor protein(s).

As used herein, a splice variant refers to variant metabotropic glutamate receptor subtype-encoding nucleic acid(s) produced by differential processing of primary transcript(s) of genomic DNA, resulting in the production of more than one type of mRNA. cDNA derived from differentially processed primary transcript will encode metabotropic glutamate receptor subtypes that have regions of complete amino acid identity and regions having different amino acid sequences. Thus, the same genomic sequence can lead to the production of multiple, related mRNAs and proteins. Both the resulting mRNAs and proteins are referred to herein as "splice variants".

Accordingly, also contemplated within the scope of the present invention are nucleic acids that encode metabotropic glutamate receptor subtypes as defined above, but that by virtue of degeneracy of the genetic code do not necessarily hybridize to the disclosed nucleic acids under specified hybridization conditions. Such subtypes also form functional receptors, as assessed by methods described herein or known to those of skill in the art. Typically, unless a metabotropic glutamate receptor subtype is encoded by RNA that arises from alternative splicing (i.e., a splice variant), metabotropic glutamate receptor subtype-encoding nucleic acids and the metabotropic glutamate receptor protein encoded thereby share substantial sequence homology with at least one of the metabotropic glutamate receptor subtype nucleic acids (and proteins encoded thereby) described herein. It is understood that DNA or RNA encoding a splice variant may share less than 90% overall sequence homology with the DNA or RNA provided herein, but include regions of nearly 100% homology to a DNA fragment described herein, and encode an open reading frame that includes start and stop codons and encodes a functional metabotropic glutamate receptor subtype.

Exemplary DNA sequences encoding human mGluR1 subtypes are represented by nucleotides which encode substantially the same amino acid sequence as set forth in Sequence ID No. 2. Presently preferred sequences encode the amino acid sequence set forth in Sequence ID No. 2.

Exemplary DNA can alternatively be characterized as those nucleotide sequences which encode an human mGluR1 subtype and hybridize under high-stringency conditions to Sequence ID No. 1.

Stringency of hybridization is used herein to refer to conditions under which polynucleic acid hybrids are stable. As known to those of skill in the art, the stability of hybrids is reflected in the melting temperature ($T_m$) of the hybrids, $T_m$ can be approximated by the formula:

$$81.5° C.-16.6(\log_{10}[Na^+])+0.41(\%G+C)-600/l,$$

where l is the length of the hybrids in nucleotides. $T_m$ decreases approximately 1°–1.5° C. with every 1% decrease in sequence homology. In general, the stability of a hybrid is a function of sodium ion concentration and temperature. Typically, the hybridization reaction is performed under conditions of lower stringency, followed by washes of varying, but higher, stringency. Reference to hybridization stringency relates to such washing conditions. Thus, as used herein:

(1) HIGH STRINGENCY refers to conditions that permit hybridization of only those nucleic acid sequences that form stable hybrids in 0.018 M NaCl at 65° C. (i.e., if a hybrid is not stable in 0.018 M NaCl at 65° C., it will not be stable under high stringency conditions, as contemplated herein). High stringency conditions can be provided, for example, by hybridization in 50% formamide, 5X Denhart's solution, 5X SSPE, 0.2% SDS at 42° C., followed by washing in 0.1X SSPE, and 0.1% SDS at 65° C.;

(2) MODERATE STRINGENCY refers to conditions equivalent to hybridization in 50% formamide, 5X Denhart's solution, 5X SSPE, 0.2% SDS at 42° C., followed by washing in 0.2X SSPE, 0.2% SDS, at 65° C.; and (3) LOW STRINGENCY refers to conditions equivalent to hybridization in 10% formamide, 5X Denhart's solution, 6X SSPE, 0.2% SDS at 42° C., followed by washing in 1X SSPE, 0.2% SDS, at 50° C.

It is understood that these conditions may be duplicated using a variety of buffers and temperatures and that they are not necessarily precise.

Denhart's solution and SSPE (see, e.g., Sambrook, Fritsch, and Maniatis, in: *Molecular Cloning, A Laboratory Manual*, Cold Spring Harbor Laboratory Press, 1989) are well known to those of skill in the art as are other suitable hybridization buffers. For example, SSPE is pH 7.4 phosphate-buffered 0.18 M NaCl. SSPE can be prepared, for example, as a 20X stock solution by dissolving 175.3 g of NaCl, 27.6 g of $NaH_2PO_4$ and 7.4 g EDTA in 800 ml of water, adjusting the pH to 7.4, and then adding water to 1 liter. Denhart's solution (see, Denhart (1966) Biochem. Biophys. Res. Commun. 23:641) can be prepared, for example, as a 50X stock solution by mixing 5 g Ficoll (Type 400, Pharmacia LKB Biotechnology, INC., Piscataway, N.J.), 5 g of polyvinylpyrrolidone, 5 g bovine serum albumin (Fraction V; Sigma, St. Louis, Mo.) water to 500 ml and filtering to remove particulate matter.

Especially preferred sequences encoding human mGluR1 subtypes are those which have substantially the same nucleotide sequence as the coding sequences in Sequence ID No. 1; with polynucleic acid having the same sequence as the coding sequence in Sequence ID No. 1 being most preferred.

As used herein, nucleotide sequences which are substantially the same share at least about 90% identity, and amino acid sequences which are substantially the same typically share more than 95% amino acid identity. It is recognized, however, that proteins (and DNA or mRNA encoding such proteins) containing less than the above-described level of homology arising as splice variants or that are modified by conservative amino acid substitutions (or substitution of degenerate codons) are contemplated to be within the scope of the present invention.

The phrase "substantial sequence homology" is used herein in reference to the nucleotide sequence of DNA, the ribonucleotide sequence of RNA, or the amino acid sequence of protein, that have slight and non-consequential sequence variations from the .actual sequences disclosed herein. Species having substantial sequence homology are considered to be equivalent to the disclosed sequences and as such are within the scope of the appended claims. In this regard, "slight and non-consequential sequence variations" mean that "homologous" sequences, i.e., sequences that have substantial homology with the DNA, RNA, or proteins disclosed and claimed herein, are functionally equivalent to the human-derived sequences disclosed and claimed herein. Functionally equivalent sequences will function in substantially the same manner to produce substantially the same compositions as the human-derived nucleic acid and amino acid compositions disclosed and claimed herein. In particular, functionally equivalent DNAs encode human-derived proteins that are the same as those disclosed herein or that have conservative amino acid variations, such as substitution of a non-polar residue for another non-polar residue or a charged residue for a similarly charged residue. These changes include those recognized by those of skill in the art as those that do not substantially alter the tertiary structure of the protein.

Exemplary DNA sequences encoding a portion of an human mGluR2 receptor subtype are represented by nucleotides which encode substantially the same amino acid sequence as set forth in Sequence ID No. 4 (optionally including some or all of the 343 nucleotides of 3' untranslated sequence set forth in Sequence ID No. 13), or substantially the same amino acid sequence as that encoded by the human mGluR2-encoding portion of clone METAB40, deposited with the ATCC on May 4, 1993, under accession number 75465.

The deposited clone has been deposited on May 4, 1993, at the American Type Culture Collection (ATCC), 12301 Parklawn Drive, Rockville, Md., U.S.A. 20852, under the terms of the Budapest Treaty on the International Recognition of Deposits of Microorganisms for Purposes of Patent Procedure and the Regulations promulgated under this Treaty. Samples of the deposited material are and will be available to industrial property offices and other persons legally entitled to receive them under the terms of the Treaty and Regulations and otherwise in compliance with the patent laws and regulations of the United States of America and all other nations or international organizations in which this application, or an application claiming priority of this application, is filed or in which any patent granted on any such application is granted. In particular, upon issuance of a U.S. patent based on this or any application claiming priority to or incorporating this application by reference thereto, all restriction upon availability of the deposited material will be irrevocably removed.

Presently preferred polynucleic acid sequences that encode a portion of an human mGluR2 receptor subtype are those that encode the same amino acid sequence as Sequence ID No. 4, or the same amino acid sequence as that encoded by the human mGluR2-encoding portion of clone METAB40, deposited with the ATCC on May 4, 1993, under accession number 75465.

Exemplary DNAs can alternatively be characterized as those nucleotide sequences which encode a human mGluR2 receptor subtype and hybridize under high-stringency conditions to Sequence ID No. 3, or the human mGluR2-encoding portion of clone METAB40 (ATCC accession No. 75465). Especially preferred sequence encoding a portion of an human mGluR2 receptor subtype is represented by polynucleic acid which has the same nucleotide sequence as the coding sequence set forth in Sequence ID No. 3, or the nucleotide sequence of the coding sequence in the human mGluR2-encoding portion of clone METAB40.

Exemplary DNA sequences encoding human mGluR3 receptor subtypes are represented by nucleotides which encode substantially the same amino acid sequence as set forth in Sequence ID No. 6. Presently preferred polynucleic acid sequences are those that encode the same sequence as Sequence ID No. 6.

Exemplary DNAs can alternatively be characterized as those nucleotide sequences which encode a human mGluR3 receptor subtype and hybridize under high-stringency conditions to Sequence ID No. 5. Especially preferred sequences encoding human mGluR3 subtypes are those which have substantially the same nucleotide sequence as the coding sequences in Sequence ID No. 5, with the polynucleic acid having the same nucleotide sequence as the coding sequence set forth in Sequence ID No. 5 being the presently most preferred.

Exemplary DNA sequences encoding human mGluR5 receptor subtypes or portions thereof are represented by nucleotides which encode substantially the same amino acid sequence as set forth in Sequence ID Nos. 8, 10 or 12. Presently preferred polynucleic acid sequences are those that encode the same sequence as Sequence ID Nos. 8, 10 or 12.

Exemplary DNAs can alternatively be characterized as those nucleotide sequences which encode a human mGluR5 receptor subtype and hybridize under high stringency conditions to Sequence ID Nos. 7, 9 or 11. Especially preferred sequences encoding Pluman mGluR5 subtypes are those which have substantially the same nucleotide sequence as the coding sequences set forth in Sequence ID Nos. 7, 9 or 11; with polynucleic acids having the same sequence as the coding sequence set forth in Sequence ID Nos. 7, 9 or 11 being the presently most preferred.

DNA encoding human metabotropic glutamate receptor subtypes may be isolated by screening suitable human cDNA or human genomic libraries under suitable hybridization conditions with DNA disclosed herein (including nucleotides derived from any of SEQ ID Nos. 1, 3, 5, 7, 9 or 11). Suitable libraries can be prepared from neural tissue samples, e.g., hippocampus and cerebellum tissue, cell lines, and the like. For example, the library can be screened with a portion of DNA including substantially the entire receptor subtype-encoding sequence thereof, or the library may be screened with a suitable oligonucleotide probe based on a portion of the DNA.

As used herein, a probe is single-stranded DNA or RNA that has a sequence of nucleotides that includes at least 14 contiguous bases that are the same as (or the complement of) any 14 or more contiguous bases set forth in any of SEQ ID Nos. 1, 3, 5, 7, 9 or 11 Preferred regions from which to construct probes include 5' and/or 3' coding sequences, sequences predicted to encode transmembrane domains, sequences predicted to encode cytoplasmic loops, signal sequences, ligand binding sites, and the like.

Either the full-length cDNA clones or fragments thereof can be used as probes, preferably labeled with suitable label means for ready detection. Fragments useful as probes include DNA sequences from the carboxyl end-encoding portion of the DNA, and most preferably will include predicted transmembrane domain-encoding portions of the DNA sequence (the domains can be predicted based on hydropathy analysis of the deduced amino acid sequence using, for example, the method of Kyte and Doolittle (1982), *J. Mol. Biol. Vol.* 157:105). These probes can be used, for example, for the identification and isolation of additional members of the glutamate receptor family.

As a particular application of the invention sequences, genetic screening can be carried out using the nucleotide sequences of the invention as probes. Thus, nucleic acid samples from patients having neuropathological conditions suspected of involving alteration/modification of any one or more of the glutamate receptors can be screened with appropriate probes to determine if any abnormalities exist with respect to any of the endogenous glutamate receptors. Similarly, patients having a family history of disease states related to glutamate receptor dysfunction can be screened to determine if they are also predisposed to such disease states.

In accordance with another embodiment of the present invention, there is provided a method for identifying DNA encoding human metabotropic glutamate receptor protein subtypes, said method comprising:

contacting human DNA with a nucleic acid probe as described above, wherein said contacting is carried out under low- to moderate-stringency hybridization conditions, and identifying DNA(s) which hybridize to said probe.

After screening the library, positive clones are identified by detecting a hybridization signal; the identified clones are characterized by restriction enzyme mapping and/or DNA sequence analysis, and then examined, by comparison with the sequences set forth herein to ascertain whether they include DNA encoding a complete metabotropic glutamate receptor subtype (i.e., if they include translation initiation and termination codons). If the selected clones are incomplete, they may be used to rescreen the same or a different library to obtain overlapping clones. If the library is genomic, then the overlapping clones may include exons and introns. If the library is a cDNA library, then the overlapping clones will include an open reading frame. In both instances, complete clones may be identified by comparison with the DNA and deduced amino acid sequences provided herein.

Complementary DNA clones encoding various human metabotropic glutamate receptor subtypes (e.g., mGluR1, mGluR2, mGluR3, mGluR5) have been isolated. Each subtype appears to be encoded by a different gene. The DNA clones provided herein may be used to isolate genomic clones encoding each subtype and to isolate any splice variants by screening libraries prepared from different neural tissues. Nucleic acid amplification techniques, which are well known in the art, can be used to locate DNA encoding splice variants of human metabotropic glutamate receptor subtypes. This is accomplished by employing oligonucleotides based on DNA sequences surrounding known or predicted divergent sequence(s) as primers for amplifying human RNA or genomic DNA. Size and sequence determinations of the amplification products can reveal the existence of splice variants. Furthermore, isolation of human genomic DNA sequences by hybridization can yield DNA containing multiple exons, separated by introns, that correspond to different splice variants of transcripts encoding human metabotropic glutamate receptor subtypes.

It has been found that not all metabotropic glutamate receptor subtypes (and variants thereof) are expressed in all neural tissues or in all portions of the brain. Thus, in order to isolate cDNA encoding a particular subtype (or splice variants thereof), it is preferable to screen libraries prepared from different neuronal or neural tissues or cells. Preferred libraries for obtaining DNA encoding each subtype include: cerebellum to isolate human mGluR1-encoding DNAs; hippocampus to isolate human mGluR2-encoding DNAs; hippocampus and cerebellum to isolate mGluR3-encoding DNAs; hippocampus and cerebellum to isolate mGluR5-encoding DNAs; and the like.

Once DNA encoding a particular receptor subtype has been isolated, ribonuclease (RNase) protection assays can be employed to determine which tissues express mRNA encoding such subtype (or splice variant thereof). These assays provide a sensitive means for detecting and quantitating an RNA species in a complex mixture of total cellular RNA. The subtype DNA is labeled and hybridized with cellular RNA. If complementary mRNA is present in the cellular RNA, a DNA-RNA hybrid results. The RNA sample is then treated with RNase, which degrades single-stranded RNA. Any RNA-DNA hybrids are protected from RNase degradation and can be visualized by gel electrophoresis and autoradiography.

It appears that the distribution of expression of some human metabotropic glutamate receptor subtypes differs from the distribution of such receptors in rat. For example, even though RNA encoding the rat mGluR5 subtype is abundant in rat hippocampus, but is not abundant in rat cerebellum [see, e.g., Abe et al., J. Biol. Chem. 267:13361–13368 (1992)], human mGluR5-encoding cDNAs were successfully obtained from human cerebellum cDNA libraries. Thus, the distribution of some metabotropic glutamate receptor subtypes in humans and rats appears to be different.

The above-described nucleotide sequences can be incorporated into vectors for further manipulation. As used herein, vector (or plasmid) refers to discrete elements that are used to introduce heterologous DNA into cells for either expression or replication thereof. Selection and use of such vehicles are well within the skill of the artisan.

Figure 2:
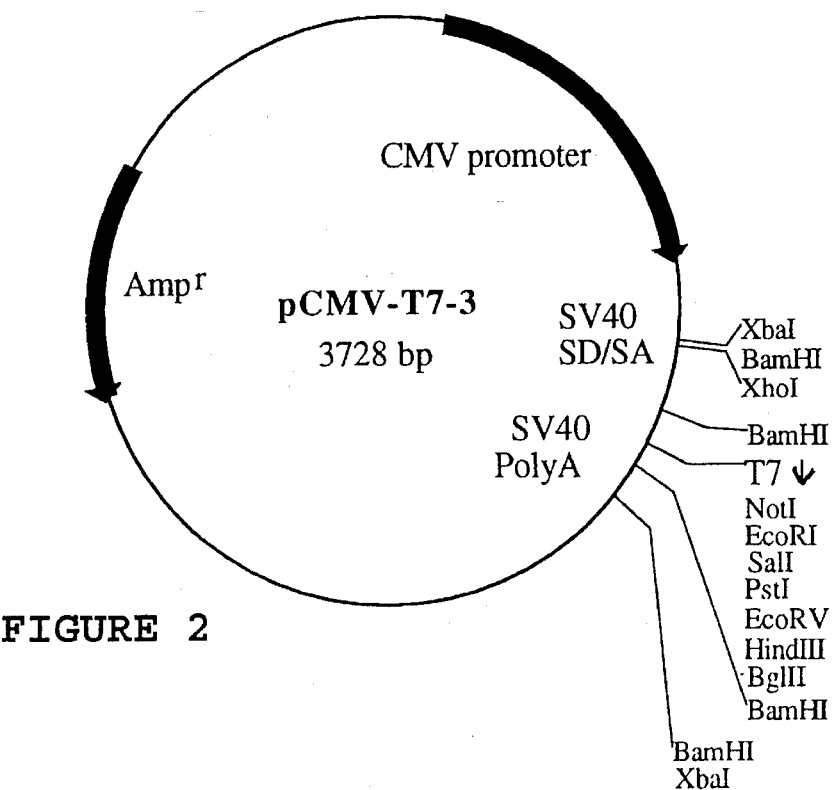
FIG. 2 presents a restriction map of the CMV promoter based vector, pCMV-T7-3.

An expression vector includes vectors capable of expressing DNAs that are operatively linked with regulatory sequences, such as promoter regions, that are capable of regulating expression of such DNA fragments. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those which integrate into the host cell genome. Presently preferred plasmids for expression of invention metabotropic glutamate receptor subtypes in eukaryotic host cells, particularly mammalian cells, include cytomegalovirus (CMV) promoter-containing vectors such as pCMV-T7-2 (see FIG. 1) and pCMV-T7-3 (see FIG. 2), pcDNA1, and the like, as well as SV40 promoter-containing vectors and MMTV LTR promoter-containing vectors.

As used herein, a promoter region refers to a segment of DNA that controls transcription of DNA to which it is operatively linked. The promoter region includes specific sequences that are sufficient for RNA polymerase recognition, binding and transcription initiation. This portion of the promoter region is referred to as the promoter. In addition, the promoter region includes sequences that modulate this recognition, binding and transcription initiation activity of RNA polymerase. These sequences may be cis acting or may be responsive to trans acting factors. Promoters, depending upon the nature of the regulation, may be constitutive or regulated. Exemplary promoters contemplated for use in the practice of the present invention include the SV40 early promoter, the cytomegalovirus (CMV) promoter, the mouse mammary tumor virus (MMTV) steroid-inducible promoter, Moloney murine leukemia virus (MMLV) promoter, and the like.

As used herein, the term "operatively linked" refers to the functional relationship of DNA with regulatory and effector sequences of nucleotides, such as promoters, enhancers, transcriptional and translational stop sites, and other signal sequences. For example, operative linkage of DNA to a promoter refers to the physical and functional relationship between the DNA and the promoter such that the transcription of such DNA is initiated from the promoter by an RNA polymerase that specifically recognizes, binds to and transcribes the DNA. In order to optimize expression and/or in vitro transcription, it may be necessary to remove, add or alter 5' untranslated portions of the clones to eliminate extra, potentially inappropriate alternative translation initiation (i.e., start) codons or other sequences that may interfere with or reduce expression, either at the level of transcription or translation. Alternatively, consensus ribosome binding sites (see, for example, Kozak (1991) J. Biol. Chem. 266:19867–19870) can be inserted immediately 5' of the start codon and may enhance expression. The desirability of (or need for) such modification may be empirically determined.

As used herein, expression refers to the process by which polynucleic acids are transcribed into mRNA and translated into peptides, polypeptides, or proteins. If the polynucleic acid is derived from genomic DNA, expression may, if an appropriate eukaryotic host cell or organism is selected, include splicing of the mRNA.

Particularly preferred base vectors which contain regulatory elements that can be linked to human metabotropic receptor-encoding DNAs for transfection of mammalian cells are cytomegalovirus (CMV) promoter-based vectors such as pCMV-T7-2 and pCMV-T7-3 (described herein) or pcDNA1 (Invitrogen, San Diego, Calif.), MMTV promoter-based vectors such as pMAMNeo (Clontech, Palo Alto, Calif.) and pMSG (Catalog No. 27-4506-01 from Pharmacia, Piscataway, N.J.), and SV40 promoter-based vectors such as pSVβ (Clontech, Palo Alto, Calif.).

Full-length DNAs encoding human metabotropic glutamate receptor subtypes have been inserted into vector pCMV-T7-2 or pCMV-T7-3. pCMV-T7-2 (and pCMV-T7-3) are pUC19-based mammalian cell expression vectors containing the CMV promoter/enhancer, SV40 splice/donor sites located immediately downstream of the promoter, a T7 bacteriophage RNA polymerase promoter positioned downstream of the splice sites, followed by an SV40 polyadenylation signal and a polylinker between the T7 promoter and the polyadenylation signal. Placement of metabotropic glutamate receptor subtype DNA between the CMV promoter and SV40 polyadenylation signal should provide for constitutive expression of the foreign DNA in a mammalian host cell transfected with the construct.

For inducible expression of human metabotropic glutamate receptor subtype-encoding DNA in a mammalian cell, the DNA can be inserted into a plasmid such as pMAMNeo or pMSG. These plasmids contain the mouse mammary tumor virus (MMTV) LTR promoter for steroid-inducible expression of operatively associated foreign DNA. If the host cell does not express endogenous glucocorticoid receptors required for glucocorticoid induction of the MMTV LTR promoter, the cell will also be transfected with DNA encoding the glucocorticoid receptor (ATCC accession no. 67200). For synthesis of in vitro transcripts, full-length human DNA clones encoding human mGluR1, mGluR3 and mGluR5 can also be subcloned into pIBI24 (International Biotechnologies, Inc., New Haven, Conn.), pCMV-T7-2 (see FIG. 1) or pCMVT-T7-3 (see FIG. 2) or pGEM7Z (Promega, Madison, Wis.).

In accordance with another embodiment of the present invention, there are provided cells containing the above-described polynucleic acids (i.e., DNA or mRNA). Such host cells as bacterial, yeast and mammalian cells can be used for replicating DNA and producing metabotropic glutamate receptor subtype(s). Methods for constructing expression vectors, preparing in vitro transcripts, transfecting DNA into mammalian cells, injecting oocytes, and performing electrophysiological and other analyses for assessing receptor expression and function as described herein are also described in PCT Application Nos. PCT/US91/05625 and PCT/US92/11090, and in co-pending U.S. application Ser. Nos. 07/563,751 and 07/812,254. The subject matter of these documents is hereby incorporated by reference herein in their entirety.

Incorporation of cloned DNA into a suitable expression vector, transfection of eukaryotic cells with a plasmid vector or a combination of plasmid vectors, each encoding one or more distinct genes or with linear DNA, and selection of transfected cells are well known in the art (see, e.g., Sambrook et al. (1989) *Molecular Cloning: A Laboratory Manual*, Second Edition, Cold Spring Harbor Laboratory Press). Heterologous DNA may be introduced into host cells by any method known to those of skill in the art, such as transfection with a vector encoding the heterologous DNA by $CaPO_4$ precipitation (see, e.g., Wigler et al. (1979) Proc. Natl. Acad. Sci. 76:1373–1376). Recombinant cells can then be cultured under conditions whereby the subtype(s) encoded by the DNA is (are) expressed. Preferred cells include mammalian cells (e.g., HEK293, CHO and Ltk⁻ cells), yeast cells (e.g., methylotrophic yeast cells, such as *Pichia pastoris*), bacterial cells (e.g., *Escherichia coli*), and the like.

While the DNA provided herein may be expressed in any eukaryotic cell, including yeast cells (such as, for example, *P. pastoris* (see U.S. Pat. Nos. 4,882,279, 4,837,148, 4,929,555 and 4,855,231), *Saccharomyces cerevisiae, Candida tropicalis, Hansenula polymorpha,* and the like), mammalian expression systems, including commercially available systems and other such systems known to those of skill in the art which express G-proteins (either endogenously or recombinantly), for expression of DNA encoding the human metabotropic glutamate receptor subtypes provided herein are presently preferred. Xenopus oocytes are preferred for expression of in vitro mRNA transcripts of DNA encoding those human metabotropic receptor subtypes that are coupled to the PI hydrolysis/$Ca^{++}$ signalling pathways. An endogenous inositol triphosphate second messenger-mediated pathway in oocytes permits functional expression of human metabotropic receptors in these cells. Oocytes expressing recombinant human metabotropic receptors respond to agonists via the oocyte G-protein-coupled $IP_3$ generation pathway, which stimulates release of $Ca^{++}$ from internal stores, and reportedly activates a chloride channel that can be detected as a delayed oscillatory current by voltage-clamp recording.

Host cells for functional recombinant expression of human metabotropic receptors preferably express endogenous or recombinant guanine nucleotide-binding proteins (i.e., G-proteins). G-proteins are a highly conserved family of membrane-associated proteins composed of $\alpha$, $\beta$ and $\gamma$ subunits. The $\alpha$ subunit, which binds GDP and GTP, differs in different G-proteins. The attached pair of $\beta$ and $\gamma$ subunits may or may not be unique; different $\alpha$ chains may be linked to an identical $\alpha\gamma$ pair or to different pairs [Linder and Gilman, Sci. Am. 267:56–65 (1992)]. More than 30 different cDNAs encoding G protein $\alpha$ subunits have been cloned [Simon et al., Science 252:802 (1991)]. Four different $\beta$ polypeptide sequences are known [Simon et al., Science 252:802 (1991)]. Three of five identified $\gamma$ cDNAs have been cloned [Hurley et al., PNAS U.S.A. 81:6948 (1984); Gautam et al., Science 244:971 (1989); and Gautam et al., PNAS U.S.A. 87:7973 (1990)]. The sequences of a fourth $\gamma$ cDNA [Kleuss et al., Science 259:832 (1993)] and a fifth $\gamma$ cDNA [Fisher and Aronson, Mol. Cell. Bio. 12:1585 (1992)] have been established, and additional $\gamma$ subtypes may exist [Tamir et al., Biochemistry 30:3929 (1991)]. G-proteins switch between active and inactive states by guanine nucleotide exchange and GTP hydrolysis. Inactive G protein is stimulated by a ligand-activated receptor to exchange GDP for GTP. In the active form, the $\alpha$ subunit, bound to GTP, dissociates from the $\beta\gamma$ complex, and the subunits then interact specifically with cellular effector molecules to evoke a cellular response. Because different G-proteins can interact with different effector systems (e.g., phospholipase C, adenyl cyclase systems) and different receptors, it is useful to investigate different host cells for expression of different recombinant human metabotropic receptor subtypes. Alternatively, host cells can be transfected with G-protein subunit-encoding DNAs for heterologous expression of differing G proteins.

In preferred embodiments, human metabotropic glutamate receptor subtype-encoding DNA is ligated into a vector, and introduced into suitable host cells to produce transformed cell lines that express a specific human metabotropic glutamate receptor subtype, or specific combinations of subtypes. The resulting cell lines can then be produced in quantity for reproducible quantitative analysis of the effects of known or potential drugs on receptor function. In other embodiments, mRNA may be produced by in vitro transcription of DNA encoding each subtype. This mRNA, either from a single subtype clone or from a combination of clones, can then be injected into Xenopus oocytes where the mRNA directs the synthesis of functional human metabotropic glutamate receptor subtypes. Alternatively, the subtype-encoding DNA can be directly injected into oocytes for expression of functional human metabotropic glutamate receptor subtypes. The transfected mammalian cells or injected oocytes may then be used in the methods of drug screening provided herein.

Eukaryotic cells in which DNA or RNA may be introduced include any cells that are transfectable by such DNA or RNA or into which such DNA or RNA may be injected and which cells express (endogenously or recombinantly) G-proteins. Preferred cells are those that express little, if any, endogenous metabotropic receptors and can be transiently or stably transfected and also express invention DNA and RNA. Presently most preferred cells are those that can form recombinant or heterologous human metabotropic glutamate receptors comprising one or more subtypes encoded by the heterologous DNA. Such cells may be identified empirically or selected from among those known to be readily transfected or injected.

Exemplary cells for introducing DNA include cells of mammalian origin (e.g., COS cells, mouse L cells, Chinese hamster ovary (CHO) cells, human embryonic kidney (HEK) cells, African green monkey cells and other such cells known to those of skill in the art), amphibian cells (e.g., *Xenopus laevis* oocytes), yeast cells (e.g., *Saccharomyces cerevisiae, Pichia pastoris*), and the like. Exemplary cells for expressing injected RNA transcripts include *Xenopus laevis* oocytes. Cells that are preferred for transfection of DNA are known to those of skill in the art or may be empirically identified, and include HEK293 (which are available from ATCC under accession #CRL 1573); Ltk⁻ cells (which are available from ATCC under accession #CCL1.3); COS-7 cells (which are available from ATCC under accession #CRL 1651); CHO cells (which are available from ATCC under accession #CRL9618, CCL61 or CRL9096); DG44 cells (dhfr CHO cells; see, e.g., Urlaub et al. (1986) Cell. Molec. Genet. 12: 555); and BHK cells (see Waechter and Baserga, PNAS U.S.A. 79:1106–1110 (1982); also available from ATCC under accession #CRL10314). Presently preferred cells include HEK293 cells, particularly HEK293 cells that can be frozen in liquid nitrogen and then thawed and regrown; for example, those described in U.S. Pat. No. 5,024,939 to Gorman (see, also, Stillman et al. (1985) Mol. Cell. Biol. 5:2051–2060), DG44 and Ltk⁻ cells.

DNA may be stably incorporated into cells or may be transiently expressed using methods known in the art. Stably transfected mammalian cells may be prepared by transfecting cells with an expression vector having a selectable marker gene (such as, for example, the gene for thymidine kinase, dihydrofolate reductase, neomycin resistance, and the like), and growing the transfected cells under conditions selective for cells expressing the marker gene. To prepare transient transfectants, mammalian cells are transfected with a reporter gene (such as the *E. coli* β-galactosidase gene) to monitor transfection efficiency. Selectable marker genes are typically not included in the transient transfections because the transfectants are typically not grown under selective conditions, and are usually analyzed within a few days after transfection.

To produce such stably or transiently transfected cells, the cells should be transfected with a sufficient concentration of subtype-encoding nucleic acids to form human metabotropic glutamate receptors indicative of the human subtypes encoded by the heterologous DNA. The precise amounts of DNA encoding the subtypes may be empirically determined and optimized for a particular subtype, cells and assay conditions. Recombinant cells that express metabotropic glutamate receptors containing subtypes encoded only by the heterologous DNA or RNA are especially preferred.

Heterologous DNA may be maintained in the cell as an episomal element or may be integrated into chromosomal DNA of the cell. The resulting recombinant cells may then be cultured or subcultured (or passaged, in the case of mammalian cells) from such a culture or a subculture thereof. Methods for transfection, injection and culturing recombinant cells are known to the skilled artisan. Similarly, the human metabotropic glutamate receptor subtypes may be purified using protein purification methods known to those of skill in the art. For example, antibodies or other ligands that specifically bind to one or more subtypes may be used for affinity purification of a given metabotropic glutamate receptor subtype.

As used herein, heterologous or foreign DNA and RNA are used interchangeably and refer to DNA or RNA that does not occur naturally as part of the genome of the cell in which it is present or to DNA or RNA which is found in a location or locations in the genome that differ from that in which it occurs in nature. Typically, heterologous or foreign DNA and RNA refers to DNA or RNA that is not endogenous to the host cell and has been artificially introduced into the cell. Examples of heterologous DNA include DNA that encodes a human metabotropic glutamate receptor subtype, DNA that encodes RNA or proteins that mediate or alter expression of endogenous DNA by affecting transcription, translation, or other regulatable biochemical processes, and the like. The cell that expresses heterologous DNA may contain DNA encoding the same or different expression products. Heterologous DNA need not be expressed and may be integrated into the host cell genome or maintained episomally.

Those of skill in the art can readily identify a variety of assays which can be used to detect the expression of functional mGluRs. Examples include PI turnover assays [see, e.g., Nakajima et al., J. Biol. Chem. 267:2437–2442 (1992) and Example 3.C.2], cAMP assays [see, e.g., Nakajima et al., supra and Example 3.C.4.], calcium ion flux assays [see, e.g., Ito et al., J. Neurochem. 56:531–540 (1991) and Example 3.C.1], cGMP assays [see, e.g., Steiner et al., J. Biol. Chem 247:1106–1113 (1972)], arachidonic acid release assays [see, e.g., Felder et al., J. Biol. Chem. 264:20356–20362 (1989)], and the like.

The DNA, mRNA, vectors, receptor subtypes, and cells provided herein permit production of selected metabotropic glutamate receptor subtypes, as well as antibodies to said receptor subtypes. This provides a means to prepare synthetic or recombinant receptors and receptor subtypes that are substantially free of contamination from many other receptor proteins whose presence can interfere with analysis of a single metabotropic glutamate receptor subtype. The availability of desired receptor subtypes makes it possible to observe the effect of a drug substance on a particular receptor subtype or combination of metabotropic glutamate receptor subtypes, and to thereby perform initial in vitro screening of the drug substance in a test system that is specific for humans and specific for a human metabotropic glutamate receptor subtype or combination of metabotropic glutamate receptor subtypes. The availability of specific antibodies makes it possible to identify the subtype combinations expressed in vivo. Such specific combinations can then be employed as preferred targets in drug screening.

The ability to screen drug substances in vitro to determine the effect of the drug on specific receptor compositions should permit the development and screening of receptor subtype-specific or disease-specific drugs. Also, testing of single receptor subtypes or specific combinations of various receptor subtypes with a variety of potential agonists or antagonists provides additional information with respect to the function and activity of the individual subtypes and should lead to the identification and design of compounds that are capable of very specific interaction with one or more receptor subtypes. The resulting drugs should exhibit fewer unwanted side effects than drugs identified by screening with cells that express a variety of receptor subtypes.

Further in relation to drug development and therapeutic treatment of various disease states, the availability of DNAs encoding human metabotropic glutamate receptor subtypes enables identification of any alterations in such genes (e.g., mutations) which may correlate with the occurrence of certain disease states. In addition, the creation of animal models of such disease states becomes possible, by specifically introducing such mutations into synthetic DNA sequences which can then be introduced into laboratory animals or in vitro assay systems to determine the effects thereof.

In another aspect, the invention comprises functional peptide fragments, and functional combinations thereof, encoded by the DNAs of the invention. Such functional peptide fragments can be produced by those skilled in the art, without undue experimentation, by eliminating some or all of the amino acids in the sequence not essential for the peptide to function as a glutamate receptor. A determination of the amino acids that are essential for glutamate receptor function is made, for example, by systematic digestion of the DNAs encoding the peptides and/or by the introduction of deletions into the DNAs. The modified (e.g., deleted or digested) DNAs are expressed, for example, by transcribing the DNA and then introducing the resulting mRNA into Xenopus oocytes, where translation of the mRNAs will occur. Functional analysis of the proteins thus expressed in the oocytes is accomplished by exposing the oocytes to ligands known to bind to and functionally activate glutamate receptors, and then monitoring the oocytes to see if endogenous channels are in turn activated. If currents are detected, the fragments are functional as glutamate receptors.

In accordance with still another embodiment of the present invention, there is provided a method for identifying compounds which bind to human metabotropic glutamate receptor subtype(s), said method comprising employing receptor proteins of the invention in a competitive binding assay. Such an assay can accommodate the rapid screening of a large number of compounds to determine which compounds, if any, are capable of displacing specifically bound [$^3$H] glutamate, i.e., binding to metabotropic glutamate receptors. Subsequently, more detailed assays can be carried out with those compounds found to bind, to further determine whether such compounds act as modulators, agonists or antagonists of invention receptors.

Another application of the binding assay of the invention is the assay of test samples (e.g., biological fluids) for the presence or absence of receptors of the present invention. Thus, for example, serum from a patient displaying symptoms related to glutamatergic pathway dysfunction can be assayed to determine if the observed symptoms are perhaps caused by over- or under-production of such receptor subtype(s).

The binding assays contemplated by the present invention can be carried out in a variety of ways, as can readily be identified by those of skill in the art. For example, competitive binding assays can be employed, such as radioreceptor assays, and the like.

In accordance with a further embodiment of the present invention, there is provided a bioassay for identifying compounds which modulate the activity of human metabotropic glutamate receptor subtypes of the invention, said bioassay comprising:

(a) exposing cells containing DNA encoding human metabotropic glutamate receptor subtype(s), wherein said cells express functional metabotropic glutamate receptors, to at least one compound whose ability to modulate the activity of said receptors is sought to be determined; and thereafter (b) monitoring said cells for changes in second messenger activity.

The above-described bioassay enables the identification of agonists, antagonists and allosteric modulators of human metabotropic glutamate receptors. According to this method, recombinant metabotropic glutamate receptors are contacted with an "unknown" or test substance (in the further presence of a known metabotropic glutamate agonist, when antagonist activity is being tested), the second messenger activity of the known glutamate receptor is monitored subsequent to the contact with the "unknown" or test substance, and those substances which increase or decrease the second messenger response of the known glutamate receptor(s) are identified as functional ligands (i.e., modulators, agonists or antagonists) for human metabotropic glutamate receptors. Second messenger activities which can be monitored include changes in the concentration of intracellular calcium ions, $IP_3$, cAMP levels, or monitoring of arachidonic acid release or activation or inhibition of ion current (when the host cell is an oocyte).

In accordance with a particular embodiment of the present invention, recombinant human metabotropic glutamate receptor-expressing mammalian cells or oocytes can be contacted with a test compound, and the modulating effect(s) thereof can then be evaluated by comparing the metabotropic glutamate receptor-mediated response in the presence and absence of test compound, or by comparing the metabotropic glutamate receptor-mediated response of test cells, or control cells (i.e., cells that do not express metabotropic glutamate receptors), to the presence of the compound.

As used herein, a compound or signal that "modulates the activity of a metabotropic glutamate receptor subtype" refers to a compound or signal that alters the activity of metabotropic glutamate receptors so that activity of the metabotropic glutamate receptor is different in the presence of the compound or signal than in the absence of the compound or signal. In particular, such compounds or signals include agonists and antagonists. The term agonist refers to a substance or signal, such as glutamate or ACPD, that activates receptor function; and the term antagonist refers to a substance that blocks agonist-induced receptor activation. Antagonists include competitive and non-competitive antagonists. A competitive antagonist (or competitive blocker) interacts with or near the site specific for the agonist (e.g., ligand or neurotransmitter) for the same or closely situated site. A non-competitive antagonist or blocker inactivates the functioning of the receptor by interacting with a site other than the site that interacts with the agonist.

As understood by those of skill in the art, assay methods for identifying compounds that modulate human metabotropic glutamate receptor activity (e.g., agonists and antagonists) generally require comparison to a control. One type of a "control" cell or "control" culture is a cell or culture that is treated substantially the same as the cell or culture exposed to the test compound, except the control culture is not exposed to test compound. For example, in methods that use voltage clamp electrophysiological procedures, the same cell can be tested in the presence and absence of test compound, by merely changing the external solution bathing the cell. Another type of "control" cell or "control" culture may be a cell or a culture of cells which are identical to the transfected cells, except the cells employed for the control culture do not express the recombinant human metabotropic glutamate receptor subtype(s) expressed in the transfected cells. In this situation, the response of test cell to test compound is compared to the response (or lack of response) of receptor-negative (control) cell to test compound, when cells or cultures of each type of cell are exposed to substantially the same reaction conditions in the presence of compound being assayed.

In accordance with yet another embodiment of the present invention, the second messenger activity of human metabotropic glutamate receptors can be modulated by contacting such receptors with an effective amount of at least one compound identified by the above-described bioassay.

In accordance with yet another embodiment of the present invention, there are provided antibodies generated against the above-described receptor proteins. Such antibodies can be employed for studying receptor tissue localization, subtype composition, structure of functional domains, as well as in diagnostic applications, therapeutic applications, and the like. Preferably, for therapeutic applications, the antibodies employed will be monoclonal antibodies.

The above-described antibodies can be prepared employing standard techniques, as are well known to those of skill in the art, using the invention receptor proteins or portions thereof as antigens for antibody production. Both anti-peptide and anti-fusion protein antibodies can be used [see, for example, Bahouth et al. (1991) *Trends Pharmacol Sci.* vol. 12:338–343; *Current Protocols in Molecular Biology* (Ausubel et al., eds.) John Wiley and Sons, New York (1989)]. Factors to consider in selecting portions of the metabotropic glutamate receptor subtypes for use as immunogen (as either a synthetic peptide or a recombinantly produced bacterial fusion protein) include antigenicity, accessibility (i.e., extracellular and cytoplasmic domains), uniqueness to the particular subtype, etc.

The availability of subtype-specific antibodies makes possible the application of the technique of immunohistochemistry to monitor the distribution and expression density of various subtypes (e.g., in normal vs diseased brain tissue). Such antibodies could also be employed for diagnostic and therapeutic applications.

In accordance with still another embodiment of the present invention, there are provided methods for modulating the ion channel activity of receptor(s) of the invention by contacting said receptor(s) with an effective amount of the above-described antibodies.

The antibodies of the invention can be administered to a subject employing standard methods, such as, for example, by intraperitoneal, intramuscular, intravenous, or subcutaneous injection, implant or transdermal modes of administration, and the like. One of skill in the art can readily determine dose forms, treatment regiments, etc, depending on the mode of administration employed.

The invention will now be described in greater detail by reference to the following non-limiting examples.

EXAMPLE 1

Isolation of DNA Encoding Human Metabotropic Glutamate Receptors

A. mGluR5 Receptor cDNA cDNA Library Screening

RNA isolated from human hippocampus tissue was used as a template for the synthesis of oligo dt-primed, single-stranded cDNA according to standard procedures [see, for example, Gubler and Hoffman (1983) Gene 25:263–269]. The single-stranded cDNA was converted to double-stranded cDNA, and EcoRI/SnaBI/XhoI adaptors were added to the ends of the cDNAs. The cDNAs were separated by size using agarose gel electrophoresis, and those that were >2.5 kb were ligated into EcoRI-digested λgt10 bacteriophage vectors. The resulting primary human hippocampus cDNA library (~2×10$^5$ recombinants) was screened for hybridization to a fragment of the DNA encoding the rat mGluR1 receptor (nucleotides 1 to 1723 plus 5' untranslated sequence; see Masu et al. (1991) Nature 349:760–765). Hybridization was performed in 5X SSPE, 5X Denhart's solution, 50% formamide, 0.2% SDS, 200 µg/ml denatured, sonicated herring sperm DNA at 42° C. and washes were performed in 1.0X SSPE, 0.2% SDS at 65° C. One hybridizing plaque, METAB1, was identified which contains a 3273 bp insert.

To obtain additional human mGluR5-encoding clones, METAB1 was radiolabeled and used to screen two human cerebellum cDNA libraries prepared as follows. cDNA was synthesized using random primers to prime first-strand cDNA synthesis from RNA isolated from human cerebellum tissue. The cDNAs were pooled based on length and two libraries were generated: one with inserts greater than 2.8 kb in length (i.e., a large-insert library) and one with inserts 1–2.8 kb in length (i.e., a medium-insert library). The libraries (1×10$^6$ recombinants in each) were screened for hybridization to the METAB1 probe using the same hybridization conditions as used for screening the hippocampus library for hybridization to the rat mGluR1 DNA fragment. Washes were performed in 1X SSPE, 0.2% SDS at 55° C. One hybridizing plaque, METAB2, was identified in the large-insert library, whereas four hybridizing plaques, METAB3-METAB6, were identified in the medium-insert library.

In another round of screening for human mGluR5encoding DNAs, a randomly primed human hippocampus cDNA library (2×10$^6$ recombinants) containing inserts ranging in size from 1–2 kb and the medium-insert cerebellum cDNA library were screened for hybridization to radiolabeled METAB5 using the same conditions as those used in screening the large- and medium-insert cerebellum libraries with METAB1. Three hybridizing plaques (METAB10-METAB12) were identified in the hippocampus library and five additional hybridizing plaques (METAB13-METAB17) were identified in another primary screening of the cerebellum library. Selected plaques were purified.

Characterization of Isolated Clones

Characterization of the inserts of the purified plaques by restriction enzyme mapping and DNA sequence analysis revealed that at least three apparent splice variants of the human mGluR5 transcript were represented by the isolated clones. Analysis of METAB1 indicated that it contains a translation initiation codon but no translation termination codon. The deduced amino acid sequence is ~70% identical to the rat mGluR1 deduced amino acid sequence, but >90% identical to the rat mGluR5 deduced amino acid sequence [Abe et al. (1992) J. Biol. Chem. 267:13361–13368].

DNA sequence analysis of METAB5 showed that it overlaps the 3' end of METAB1 at the 5' end and continues for an additional 343 nucleotides in the 3' direction. Comparison of the overlapping regions of METAB1 and METAB5 revealed that METAB1 contains 96 nucleotides that are not present in METAB5 (i.e., METAB1 contains a 96-nucleotide insertion relative to METAB5). METAB5 also does not contain a translation termination codon. The insert of METAB12 overlaps the 3' end of METAB5 at the 5' end, however, and extends farther in the 3' direction to include a translation termination codon.

DNA sequence analysis of METAB2 showed that the first 869 nucleotides at the 5' end overlap, and are identical to a portion of the 3' end of METAB1; however, the sequences of METAB1 and METAB2 diverge at the beginning of the 96-nucleotide insertion of METAB1. METAB2 extends approximately 2700 nucleotides in the 3' direction and contains a putative translation termination codon 4 nucleotides 3' of the point of divergence with METAB1.

Partial DNA sequence analysis of METAB14 indicated that it encodes a portion of another human metabotropic receptor, mGluR1 (see Example IB).

Preparation of Full-Length mGluR5 cDNA Constructs

Full-length constructs representing three putative splice variants of the human mGluR5 transcript, designated mGluR5a, mGluR5b and mGluR5c, can be generated and incorporated into expression vectors for use in preparing in vitro transcripts of the cDNAs and/or expression of the cDNAs in mammalian cells. The base expression vector typically used is pCMV-T7-3 (see FIG. 2) or pCMV-T7-2 (see FIG. 1). Plasmid pCMV-T7-3 is a pUC19-based vector that contains a cytomegalovirus (CMV) promoter/enhancer, SV40 splice donor/splice acceptor sites located immediately downstream of the promoter, a T7 bacteriophage RNA polymerase promoter positioned downstream of the SV40 splice sites, an SV40 polyadenylation signal downstream of the T7 promoter, and a polylinker between the T7 promoter and the polyadenylation signal. This vector thus contains all the regulatory elements required for expression of heterologous DNA in a mammalian host cell, wherein the heterologous DNA has been incorporated into the vector at the polylinker. In addition, because the T7 promoter is located just upstream of the polylinker, this plasmid can be used for synthesis of in vitro transcripts of heterologous DNA that has been subcloned into the vector at the polylinker. pCMV-T7-3 and pCMV-T7-2 differ only in the orientation of the restriction sites in the polylinker.

To prepare a full-length mGluR5a construct (see Sequence ID No. 7), portions of clones METAB1, METAB5, and METAB12 were ligated together. Initially, the inserts of METAB1, METAB5 and METAB12 were separately transferred from λgt10 as EcoRI fragments into EcoRI-digested pGEM-7Zf (Promega, Madison, Wis.) for ease of manipulation. The pGEM-7Zf vector containing the METAB1 insert was digested with ScaI/NheI to release a 3.8 kb fragment containing the 5' half of the ampicillin resistance gene and a 5' portion of the METAB1 insert (nucleotides 1–2724 of Sequence ID No. 7). The pGEM-7Zf vector containing the insert of METAB5 was digested with ScaI/NheI to release a 2.6 kb fragment containing the 3' half of the ampicillin resistance gene and a 3' portion of METAB5 (nucleotides 2725–3469 of Sequence ID No. 7), and this fragment was ligated with the 3.8 kb fragment from the pGEM-7Zf vector containing METAB1 to create pGEM-METAB1+5. pGEM-METAB1+5 was digested with ScaI/NotI to release a 4.4 kb fragment containing the 5' half of the ampicillin resistance gene and nucleotides 1–3316 of Sequence ID No. 7. This 4.4 kb fragment was then ligated with a 2.6 kb fragment obtained by ScaI/NotI (partial) digestion of the pGEM-7Zf vector containing the METAB12 insert [the 2.6 kb fragment contains the 3' half of the ampicillin resistance gene and a 3' portion of METAB12 (nucleotides 3317–4085 of Sequence ID No. 7)]. The resulting vector contained the complete mGluR5a coding sequence in pGEM-7Zf. The full-length mGluR5a cDNA was isolated from the vector as an AatII (blunt-ended)-HindIII fragment and subcloned into NotI (blunt-ended)/HindIII-digested pCMV-T7-3 to generate construct mGluR5a1.

In summary, construct mGluR5a1 contains 369 bp of 5' untranslated sequence from METAB1 (nucleotides 1–369 of Sequence ID No. 7) and a complete coding sequence (nucleotides 370–3912 of Sequence ID No. 7) for the mGluR5a variant of the mGluR5 receptor, as well as 173 bp of 3' untranslated sequence (nucleotides 3913–4085 of Sequence ID No. 7). The mGluR5a-encoding sequence is operatively linked to the regulatory elements in pCMV-T7-3 for use in expressing the receptor in mammalian host cells and for use in generating in vitro transcripts of the DNA to be expressed in Xenopus oocytes.

Two additional mGluR5a constructs (mGluR5a2 and mGluR5a3) were prepared by modification of the 5' untranslated region of the first mGluR5a construct. The above-described mGluR5a construct contains seven potentially inappropriate ATG translation initiation codons in the 5' untranslated region that precedes the proposed translation initiation codon (nucleotides 370 to 372 of Sequence ID No. 7). The mGluR5a1 construct was digested with Ba131 to accomplish the following: (1) remove 255 nucleotides of sequence (nucleotides 1–255 of Sequence ID No. 7, containing six of the seven upstream ATG triplets), thereby creating mGluR5a2 and (2) remove 348 nucleotides of sequence (nucleotides 1–348 of Sequence ID No. 7, containing all upstream ATG triplets), thereby creating mGluR5a3. Thus, mGluR5a2 is identical to mGluR5a1 except that it lacks some of the 5' untranslated sequence and thus contains only one ATG triplet upstream of the proposed translation initiation codon. Similarly, mGluR5a3 is identical to mGluR5a1 except that it lacks all of the ATG triplets upstream of the proposed translation initiation codon and contains only 21 nucleotides of 5' untranslated sequence.

A third mGluR5a construct, MMTV-hmGluR5a, was prepared for use in MMTV promoter-regulated expression of mGluR5a as follows. mGluR5a3 was digested with XbaI. The 4.1 kb fragment containing the SV40 splice sites, the full-length mGluR5a coding sequence (plus 21 nucleotides of 5' untranslated sequence and 173 nucleotides of 3' untranslated sequence) and the polyadenylation signal was isolated, blunt-ended and ligated to a 2 kb EcoRI-NdeI (blunt-ended) fragment of pBR322 to create pBR-hmGluR5. Vector pMAMneo (Clontech, Palo Alto, Calif.), which contains the MMTV LTR promoter, and ampicillin and neomycin resistance genes, was digested with BamHI, to remove the neomycin resistance gene, and allowed to religate. The vector was then digested with EcoRI, and the fragment containing the ampicillin resistance gene was religated with the larger vector fragment in the reverse orientation. This vector was digested with PstI/NheI, and the 2.3 kb fragment containing a 5' portion of the ampicillin resistance gene and the MMTV-LTR was isolated. Plasmid pBR-hmGluR5 was digested with PstI/XbaI, and the 5.3 kb fragment containing a 3' portion of the ampicillin resistance gene and the mGluR5a sequence (with SV40 splice sites and polyadenylation signal) was ligated with the 2.3 kb Pst/NheI fragment of pBR-hmGluR5 to create MMTV-hmGluR5a.

Thus, pMMTV-hmGluR5a contains the MMTV-LTR followed by SV40 splice sites in operative linkage with the mGluR5a DNA (containing nucleotides 349–4085 of Sequence ID No. 7) followed by a polyadenylation signal.

A fourth mGluR5a construct, pSV-hmGluR5, was prepared for use in SV40 promoter-regulated expression of mGluR5a as follows. mGluR5a3 was partially digested with XhoI, treated with Klenow and allowed to religate to itself, thereby destroying the XhoI site located 3' of the mGluR5a DNA. The plasmid was then digested with ScaI/XhoI, generating a fragment containing the SV40 splice sites, the full-length mGluR5a coding sequence (plus 21 nucleotides of 5' untranslated sequence and 173 nucleotides of 3' untranslated sequence), the polyadenylation signal and a 3' portion of the ampicillin resistance gene. Plasmid pSVβ (Clontech, Palo Alto, Calif.) was digested with ScaI/XhoI, and the fragment containing a 5 portion of the ampicillin resistance gene and the SV40 early promoter was ligated to the ScaI/XhoI fragment containing the mGluR5a DNA to create pSV-hmGluR5. Thus, pSV-hmGluR5 contains the SV40 early promoter followed by SV40 splice sites in operative linkage with the mGluR5a DNA (containing nucleotides 349–4085 of Sequence ID No. 7) followed by a polyadenylation signal.

To prepare a full-length mGluR5b construct, an mGluR5a construct (mGluR5a1, mGluR5a2 or mGluR5a3) was digested with NheI/PmlI to release a fragment containing nucleotides 2725–3020 of Sequence ID No. 7. The remaining vector fragment was then ligated to the NheI/PmlI fragment isolated from METAB1. The resulting vector, mGluR5b, is identical to the mGluR5a construct from which it was prepared, except that it includes a 96 bp insertion (nucleotides 3000–3095 of Sequence ID No. 9) located between nucleotides 2999 and 3000 of Sequence ID No. 7. Sequence ID No. 9 is the complete nucleotide sequence of the full-length mGluR5b cDNA prepared from vector mGluR5a1.

To prepare a full-length mGluR5c construct, an mGluR5a construct (mGluR5a1, mGluR5a2 or mGluR5a3) is digested with NheI/HindIII (the HindIII site is present in the polylinker of the pCMV-T7-3 portion of the mGluR5a vector) to release a fragment containing nucleotides 2725–4085 of Sequence ID No. 7. The remaining vector fragment is then ligated to the NheI/HindIII fragment isolated from METAB2. The resulting full-length cDNA, mGluR5c (Sequence ID No. 11), is identical to the mGluR5a construct from which it was prepared for the first 2630 nucleotides of the coding sequence; however, at nucleotide 2631 of the coding sequence, the coding sequences of mGluR5c and mGluR5a diverge (e.g., beginning at nucleotide 3000 of Sequence ID No. 7) with the mGluR5c coding sequence having a guanine nucleotide as nucleotide 263], of the coding sequence followed immediately by a translation termination codon (nucleotides 3001–3003 of Sequence ID No. 11).

B. mGluR1 Receptor cDNA cDNA Library Screening

The medium-insert cerebellum library was screened for hybridization to a fragment of the DNA encoding the rat mGluR1 receptor (nucleotides 1 to 3031 plus 5' untranslated sequence; see Masu et al. (1991) Nature 349:760–765). Hybridization was performed in 5X SSPE, 5X Denhart's solution, 50% formamide, 0.2% SDS, 200 µg/ml denatured, sonicated herring sperm DNA at 42° C. and washes were performed in 1X SSPE, 0.2% SDS at 55° C. Three hybridizing plaques, METAB7-METAB9, were identified.

In a subsequent round of screening, an independent plating of 1×10⁶ recombinants of the human medium-insert cerebellum cDNA library was probed for additional human mGluR1 clones. This plating was screened sequentially for hybridization first to a DNA fragment containing nucleotides 1–1256 (plus 5' untranslated sequence) of the rat mGluR1 cDNA (i.e., a 5' probe) and then to a DNA fragment containing nucleotides 2075–3310 of the rat mGluR1a cDNA (i.e., a 3' probe) using the same hybridization and wash conditions as those used in the previous screening that identified clones METAB7-METAB9. Three clones (METAB18, METAB21 and METAB22) were identified by hybridization to the 5' probe, and three clones (METAB19, METAB20 and METAB23) were identified by hybridization to the 3' probe.

The 5' rat mGluR1 fragment was used as a probe to screen the large-insert human cerebellum cDNA library for further mGluR1 clones. Hybridization and wash conditions were essentially identical to those used in isolating the six mGluR1 clones from the medium-insert cerebellum library(except 20% formamide was used in the hybridization solution). Three plaques, METAB58, METAB59 and METAB60, hybridized to the probe.

Characterization of Isolated Clones

The inserts of the purified plaques were characterized by restriction enzyme mapping and DNA sequence analysis. METAB58 is ~2.8 kb and contains 5' untranslated sequence, a translation initiation codon and ~2.3 kb of coding sequence. The 3' end of METAB58 overlaps the 5' end of METAB19. METAB19 extends ~700 bp in the 3' direction and contains a translation termination codon. Thus, METAB58 and METAB19 overlap to encode a full-length mGluR1 receptor (see Sequence ID No. 1). The other clones are also partial mGluR1 cDNAs that contain nucleotide sequences from the portion of the mGluR1 coding sequence located between the translation initiation and termination codons.

To determine if additional clones encoding the 3' end of the human mGluR1 transcript were present in human cDNA libraries, the cDNAs from the hippocampus/basal ganglia and cerebellum libraries were subjected to nucleic acid amplification. The 5' primer consisted of nucleotides 2218 to 2240 of Sequence ID No. 1 whereas the 3' primer was a degenerate oligonucleotide based on amino acids 890–897 of the rat mGluR1a coding sequence (see Pin et al. (1992) Neurobiology 89:10331–10335). The products of the amplification were analyzed by gel electrophoresis. A single product (i.e., a 500 bp fragment) was detected in only the hippocampus/basal ganglia library.

To obtain additional clones representing the 3' end of the mGluR1 transcript, the hippocampus and cerebellum cDNA libraries can be screened (using conditions similar to those used for obtaining human mGluR1 cDNAs described above) with a fragment from the 3' end of the rat mGluR1a cDNA (e.g., the ~2 kb NcoI/ClaI fragment of the rat mGluR1a cDNA). This probe corresponds to a portion of the 3' region of the mGluR1 cDNA that does not appear to be alternatively spliced. Hybridizing clones are then analyzed by restriction mapping and DNA sequence analysis to determine if different 3' ends are represented.

Preparation of Full-Length mGluR1 cDNA Constructs

To prepare a full-length construct encoding the B form of the human mGluR1 receptor, portions of clones METAB58 and METAB19 were ligated. METAB58 was digested with EcoRI/AccI and the 2456 bp fragment containing nucleotides 171–2626 of Sequence ID No. 1 was isolated. The 704 bp fragment of METAB19 (containing nucleotides 2627–3330 of Sequence ID No. 1) was isolated by digestion of METAB19 with AccI/XhoI. This fragment was ligated to the 2456 bp fragment of METAB58 and to EcoRI/SalI-digested vector pCMV-T7-3. The resulting construct encoding human mGluR1B contained 234 nucleotides of 5' untranslated sequence (nucleotides 171–404 of Sequence ID No. 1), the entire mGluR1B coding sequence (nucleotides 405–3122 of Sequence ID No. 1), and 208 nucleotides of 3' untranslated sequence (nucleotides 3123–3330 of Sequence ID No. 1). The mGluR1B-encoding sequence is operatively linked to the regulatory elements in pCMV-T7-3 for expression in mammalian cells.

Several methods can be employed to determine which mGluR5 and mGluR1 receptor variants are actually expressed in various human tissues. For example, oligonucleotides specific for the nucleotide sequences located 5' and 3' of the insertions/deletions (i.e., regions of divergence) of mGluR transcripts described herein can be used to prime nucleic acid amplifications of RNA isolated from various tissues and/or cDNA libraries prepared from various tissues. The presence or absence of amplification products and the sizes of the products indicate which variants are expressed in the tissues. The products can also be characterized more thoroughly by DNA sequence analysis.

RNase protection assays can also be used to determine which variant transcripts are expressed in various tissues. These assays are a sensitive method for detecting and quantitating an RNA species in a complex mixture of total cellular RNA. A portion of the mGluR DNA is labeled and hybridized with cellular RNA. If complementary mRNA is present in the cellular RNA, a DNA-RNA hybrid results. The RNA sample is then treated with RNase, which degrades single-stranded RNA. Any RNA-DNA hybrids are protected from RNase degradation and can be visualized by gel electrophoresis and autoradiography.

Isolation of genomic clones containing human metabotropic receptor-encoding sequences by, for example, hybridization to the human mGluR cDNAs disclosed herein and subsequent characterization of the clones provides further information on possible splice variants of the mGluR primary transcripts.

C. mGluR3 Receptor cDNA cDNA Library Screening

A human hippocampus cDNA library (generated using random primers to prime cDNA synthesis and then selecting cDNAs that were 1.0–2.8 kb for ligation to λgt10 vectors)

was screened for hybridization to a 500 bp SmaI/XbaI fragment of the rat mGluR2 cDNA and a 3 kb AccI-BamHI fragment of the rat mGluR3 cDNA [see Tanabe et al. (1992) Neuron 8:169–179]. Hybridization was performed in 5X SSPE, 5X Denhart's solution, 50% formamide, 0.2% SDS, 200 μg/ml denatured, sonicated herring sperm DNA at 42° C. and washes were performed in 0.5X SSPE, 0.2% SDS at 65° C. Three hybridizing plaques, METAB40, METAB41 and METAB45, were identified.

A portion of the 5' end of METAB45 (i.e., the first 244 bp; nucleotides 2634–2877 of Sequence ID No. 5) was then used to screen an amplified cerebellum library (generated using random primers to prime cDNA synthesis and then selecting cDNAs that were >2.8 kb for ligation to λgt10 vectors) and an amplified hippocampus cDNA library (generated using random primers to prime cDNA synthesis and then selecting cDNAs that were >2.0 kb for ligation to λgt10 vectors) for additional mGluR3 clones. One million clones from each library were screened. Hybridization and wash conditions were identical to those used in isolating METAB40, METAB41 and METAB45 from the hippocampus library. Three hybridizing plaques were identified in each library: METAB46, METAB49 and METAB50 in the cerebellum library and METAB47, METAB48 and METAB51B in the hippocampus library.

Characterization of Isolated Clones

The inserts of the purified plaques were characterized by restriction enzyme mapping and DNA sequence analysis. Each of the isolated clones are partial cDNAs encoding portions of the human mGluR3 receptor, except for clone METAB40, which encodes a portion of the human mGluR2 receptor (see Example 1.D.). Clones METAB41, METAB45 and METAB47–49 contain sequence from the 3' end of the mGluR3 coding sequence as well as a translation termination codon. Clones METAB46, METAB50 and METAB51B contain sequence from the 5' end of the mGluR3 cDNA, including a translation initiation codon, and varying amounts of 5' untranslated sequence.

Preparation of Full-Length mGluR3 cDNA Constructs

Four constructs containing the full-length human mGluR3 coding sequence were prepared by ligating portions of METAB48 and METAB46 or METAB51B. The full-length coding sequence is provided in Sequence ID No. 5 (nucleotides 1064–3703). The inserts of clones METAB46 and METAB51B were separately subcloned into pCMV-T7-3 as EcoRI fragments. The insert of clone METAB48 was subcloned as an EcoRI fragment into pCMV-T7-2.

To generate construct mGluR3B, the pCMV-T7-3 plasmid containing the METAB51B insert was digested with ScaI/BglII, and the 2.6 kb fragment containing the 5' half of the ampicillin resistance gene and a 5' portion of the METAB51B insert (nucleotides 748–1671 of Sequence ID No. 5) was isolated. This fragment was ligated to a 4.3 kb fragment isolated from a ScaI/BglII digest of the pCMV-T7-3 plasmid harboring the insert of METAB48 [the 4.3 kb fragment contains the 3' half of the ampicillin resistance gene and a 3' portion of METAB48 (nucleotides 1672–3919 of Sequence ID No. 5)]. The resulting construct, mGluR3B, contains 316 nucleotides of 5' untranslated sequence (nucleotides 748–1063 of Sequence ID No. 5), the entire mGluR3 coding sequence (nucleotides 1064–3703 of Sequence ID No. 5), and 216 nucleotides of 3' untranslated sequence (nucleotides 3704–3919 of Sequence ID No. 5). The mGluR3Bencoding sequence is operatively linked to the regulatory elements in pCMV-T7-3 for expression in mammalian cells.

To generate construct mGluR3C, the pCMV-T7-2 plasmid harboring the insert of METAB46 was digested with ScaI/BglII and the 3.6 kb fragment containing the 5' half of the ampicillin resistance gene and a 5' portion of METAB46 (nucleotides 1–1671 of Sequence ID No. 5) was isolated. This fragment was ligated to the same ScaI/BglII fragment of METAB48 as was used in construct mGluR3B. The resulting construct, mGluR3C, contains 1063 nucleotides of 5' untranslated sequence (nucleotides 1–1063 of Sequence ID No. 5), the entire mGluR3 coding sequence (nucleotides 1064–3703 of Sequence ID No. 5)., and 216 nucleotides of 3' untranslated sequence (nucleotides 3704–3919 of Sequence ID No. 5). The mGluR3C-encoding sequence is operatively linked to the regulatory elements from vectors pCMV-T7-2 and pCMV-T7-3 for expression in mammalian cells.

Construct mGluR3A was generated by digesting mGluR3C with EcoRV and NotI to remove a fragment containing nucleotides 1–1035 of Sequence ID No. 5, making the NotI site blunt-ended and then allowing the larger vector fragment to re-ligate. Construct mGluR3A contains 28 nucleotides of 5' untranslated sequence (nucleotides 1036–1063 of Sequence ID No. 5), the entire mGluR3 coding sequence (nucleotides 1064–3703 of Sequence ID No. 5) and 216 nucleotides of 3' untranslated sequence (nucleotides 3704–3919 of Sequence ID No. ! 5). The mGluR3A-encoding sequence is operatively linked to the regulatory elements from vectors pCMV-T7-3 and pCMV-T7-2 for expression in mammalian cells.

To generate construct pSV-hmGluR3C (for use in SV40 promoter-regulated expression of mGluR3), the pCMV-T7-2 plasmid harboring the insert of METAB46 was digested with ScaI/NotI, and the fragment containing the 3' portion of the ampicillin resistance gene and the entire METAB46 insert was isolated. Plasmid pSVβ was digested with ScaI/NotI, and the fragment containing the 5' portion of the ampicillin resistance gene and the SV40 early promoter and splice sites was ligated to the ScaI/NotI fragment from the pCMV-T7-2 vector harboring METAB46 to create pSV-METAB46. Plasmid pSV-METAB46 was digested with ScaI/BglII and the fragment containing the 5' portion of the ampicillin resistance gene, the SV40 early promoter and splice sites and a 5' portion of METAB46 (nucleotides 1–1671 of Sequence ID No. 5) was isolated. This fragment ligated to the same ScaI/BglII fragment of METAB48 as was used in constructs mGluR3B and mGluR3C. The resulting construct, pSV-hmGluR3C, contains the SV40 promoter followed by SV40 splice sites in operative linkage with the mGluR3 DNA (containing nucleotides 1–3919 of Sequence ID No. 5) followed by a polyadenylation signal.

D. mGluR2 Receptor cDNA

Clone METAB40 was isolated from a human hippocampus cDNA library as described in Example 1.C. The insert cDNA of METAB40 is 1100 bp in length and encodes the 3' end of a human mGluR2 receptor, including a translation termination codon and 3' untranslated sequence. The first 355 nucleotides of METAB40 are provided in Sequence ID No. 3; the last 343 nucleotides of METAB40 (which are all from the 3' untranslated sequence) are provided in Sequence ID No. 13).

To isolate clones containing DNA representing the 5' portion of the mGluR2 transcript, the human hippocampus cDNA library can be screened for hybridization to an oligonucleotide corresponding to the 5' end of METAB40. Hybridizing plaques are purified and characterized by DNA sequence analysis. Clones that overlap with METAB40 and contain a translation initiation codon can be ligated to METAB40 at appropriate restriction sites to generate a full-length mGluR2-encoding cDNA construct.

EXAMPLE 2

Expression of Recombinant Human Metabotropic Glutamate Receptors in Oocytes

Xenopus oocytes were injected with in vitro transcripts prepared from constructs containing DNA encoding human metabotropic receptors. Electrophysiological measurements of the oocyte transmembrane currents were made using the two-electrode voltage clamp technique (see e.g., Stuhmer (1992) Meth. Enzymol. 207: 319–339).

A. Preparation of In Vitro Transcripts

Recombinant capped transcripts of metabotropic receptor cDNAs contained in construct mGluR5a3 were synthesized from linearized plasmids using the Megascript Kit (Cat. #1334, Ambion, Inc., Austin, Tex.). The mass of each synthesized transcript was determined by UV absorbance and the integrity of each transcript was determined by electrophoresis through an agarose gel.

B. Electrophysiology

Xenopus oocytes were injected with 10–50 ng of metabotropic receptor transcripts per oocyte. The preparation and injection of oocytes were carried out as described by Dascal [(1987) Crit. Rev. Biochem. 22:317–387]. Two-to-six days following mRNA injection, the oocytes were examined using the two-electrode voltage clamp technique. The cells were bathed in Ringer's solution (115 mM NaCl, 2.5 mM KCl, 1.8 mM $CaCl_2$, 10 m MHEPES, pH 7.3), and the membrane potential was clamped at $-80$ to $-100$ mV. Drugs were applied by pipetting 60 µl aliquots of drug-containing solution directly into the bath. Data were sampled at 2–5 Hz with a Labmaster data acquisition board in PC-386 using AXOTAPE version 1.2 (Axon Instruments, Foster City, Calif.) software. Data were exported to a laser printer or plotted using Sigmaplot version 5.0.

Metabotropic receptor-modulating compounds, i.e., 0.001–0.1 µM quisqualate, 0.1–10 µM glutamate and 0.1–300 µM 1S,3R-ACPD (1-amino-cyclopentyl-1,3-dicarboxylic acid), were applied to the bath and the transmembrane currents were recorded. Significant currents were detected after application of the compounds. Dose-response studies in which the currents measured after application of varying amounts of each compound were compared revealed that the current magnitude increased with increasing concentration of each compound. Analysis of these data enabled a calculation of $EC_{50}$ values for each compound which were used in determining the relative potencies of the compounds.

EXAMPLE 3

Recombinant Expression of Human Metabotropic Glutamate Receptor Subunits in Mammalian Cells Human embryonic kidney (HEK 293 ) and Chinese hamster ovary (CHO) cells (i.e, DG44 cells; see Urlaub et al. (1986) Som. Cell. Molec. Genet. 12: 555) were transfected with DNA encoding human metabotropic receptors. Transfectants were analyzed for expression of metabotropic receptors using various assays, e.g., inositol phosphate ($IP_1$) assays, $Ca^{2+}$-sensitive fluorescent indicator-based assays, and [$^3$H]-glutamate binding assays.

A. Transient Transfection of HEK 293 Cells

HEK 293 cells were transiently transfected with DNA encoding mGluR5a (constructs mGluR5a2 and mGluR5a3 and construct MMTV-hmGluR5a) receptors. Approximately $2 \times 10^6$ HEK cells were transiently transfected with 5–18 µg (or 0.18 µg in some transfections, see Example 3.C.2.) of the indicated plasmid according to standard $CaPO_4$ transfection procedures [see Wigler et al. (1979) Proc. Natl. Acad. Sci. USA 76:1373–1376]. In addition, 0.5–2 µg (or 0.18 µg in some transfections, see Example 3.C.2) of plasmid pCMVβgal (Clontech Laboratories, Palo Alto, Calif.), which contains the *Escherichia coli* β-galactosidase gene fused to the CMV promoter, were co-transfected as a reporter gene for monitoring the efficiency of transfection. The transfectants were analyzed for β-galactosidase expression by direct staining of the product of a reaction involving β-galactosidase and the X-gal substrate [Jones (1986) EMBO 5:3133–3142]. Transfectants can also be analyzed for β-galactosidase expression by measurement of β-galactosidase activity [Miller (1972) in Experiments in Molecular Genetics, pp.352–355, Cold Spring Harbor Press].

HEK 293 cells that were transiently transfected with 5 µg of MMTV-hmGluR5A were co-transfected with 5 µg of pRShGR (ATCC accession no. 67200) which contains DNA encoding a glucocorticoid receptor operatively linked to the Rous Sarcoma virus (RSV) LTR promoter. Co-expression of glucocorticoid receptors in these cells should insure that induction of expression of the MMTV promoter-mGluR5a DNA occurs upon addition of glucocorticoid (e.g., dexamethasone) to the cells.

The efficiency of these transfections of HEK cells was typical of standard efficiencies (i.e., ~50%).

B. Stable Transfection of Mammalian Cells

Mammalian cells, such as HEK 293, Ltk⁻ and CHO cells (e.g., DG44 cells), can be stably transfected using the calcium phosphate transfection procedure [Current Protocols in Molecular Biology, Vol. 1, Wiley Inter-Science, Supplement 14, Unit 9.1.1–1.9 (1990)]. When CHO cells are used as hosts, it is generally preferable to use the SV40 promoter to regulate expression of the human metabotropic receptor-encoding cDNA. Ten-cm plates, each containing $1–2 \times 10^6$ cells, are transfected with 1 ml of DNA/calcium phosphate precipitate containing approximately 5–10 µg of metabotropic receptor-encoding DNA and 0.5–1 µg of DNA encoding a selectable marker, for example, the neomycin-resistance gene (i.e., pSV2neo) for selection of HEK 293 transformants, the thymidine kinase gene for Ltk⁻ cell transfectants, or the dihydrofolate reductase (dhfr) gene for selection of DG44 cell transformants. After ~14 days of growth in the appropriate selective media, colonies form and are individually isolated using cloning cylinders. The isolates are then subjected to limiting dilution and screened to identify those that express metabotropic receptors using, for example, methods described below.

Analysis of Transfectants

1. Fluorescent indicator-based assays

Activation of G-protein-coupled metabotropic receptors by agonists leads to stimulation of the phosphatidylinositol (PI) hydrolysis/intracellular $Ca^{2+}$ signalling pathway and/or the inhibitory cAMP cascade. Methods of detecting transient increases in intracellular calcium concentration can be applied to the analysis of functional expression of metabotropic receptors that are coupled to the PI hydrolysis/$Ca^{2+}$ mobilization pathway or to both the PI hydrolysis/$Ca^{2+}$ mobilization pathway and the inhibitory cAMP cascade. One method for measuring intracellular calcium levels relies on calcium-sensitive fluorescent indicators.

Calcium-sensitive indicators, such as fluo-3 and fura-2 (Molecular Probes, Inc., Eugene, Oreg.) are available as acetoxymethyl esters which are membrane permeable. When the acetoxymethyl ester form of the indicator enters a cell, the ester group is removed by cytosolic esterases, thereby trapping the free indicator in the cytosol. Interaction of the free indicator with calcium results in increased fluorescence of the indicator; therefore, an increase in the intracellular $Ca^{2+}$ concentration of cells containing the indicator can be expressed directly as an increase in fluorescence (or an increase in the ratio of the fluorescence at two wavelengths when fura-2 is used). An automated fluorescence detection system for assaying metabotropic receptors has been described in commonly assigned pending U.S. patent application Ser. No. 07/812,254 now abandoned and corresponding PCT patent application No. WO93/13423, both of which are hereby incorporated by reference herein. Additionally, fluorescence imaging techniques can be utilized to visualize intracellular $Ca^{2+}$ oscillations.

HEK cells that were transiently transfected with DNA encoding a human mGluR5a receptor were analyzed for expression of functional recombinant metabotropic receptors using the automated fluorescent indicator-based assay and the fluorescence imaging assay. Likewise, cells stably transfected with metabotropic receptor DNAs can also be analyzed for functional metabotropic receptors using these assay systems.

a. Automated fluorescence assay

Untransfected HEK 293 cells (or HEK 293 cells transiently transfected with pCMV-T7-3) and HEK 293 cells that had been transfected with mGluR5a-encoding DNA were plated in the wells of a 96-well microtiter dish (Nunc Catalog No. 1-6708, distributed by Alameda Industries, Escondido, Calif.) that had been precoated with poly-L-lysine at a density of $2 \times 10^5$ cells/well and loaded with fluo-3 by incubation for 2 hours at 20° C. in a medium containing 20 µM fluo-3, 0.2% Pluronic F-127 in HBS (125 mM NaCl, 5 mM KCl, 1.8 mM $CaCl_2$, 0.62 mM $MgCl_2$, 20 mM glucose, 20 nM HEPES, pH 7.4). The cells were then washed with assay buffer (i.e. HBS). The microtiter dish was then placed into a fluorescence plate reader (e.g., Fluoroskan II, Lab Products International, Ltd., Raleigh, N.C.), and the basal fluorescence of each well was measured and recorded before addition of metabotropic receptor-modulating compounds such as quisqualate, glutamate, trans-ACPD (1-amino-cyclopentane-1,3-dicarboxylic acid), 1S,3R-ACPD, AP3 (2-amino-3-phosphonopropionate) AP5 (2-amino-5phosphonopentanoate), and CNQX (6-cyano-7-nitroquinoxaline-2,3-dione) to the wells. The fluorescence of the wells was monitored repeatedly (75 readings at 0.63-sec intervals) following addition of agonist.

In general, the fluorescence of the untransfected HEK 293 cells did not change after addition of any of these compounds. The fluorescence of HEK 293 cells transiently transfected with either the mGluR5a3 or MMTV-hmGluR5a constructs increased in response to application of glutamate, quisqualate, trans-ACPD, or 1S,3R-ACPD. The fluorescence increased to a peak value, then decreased over time to the basal level of fluorescence in cells prior to application of the compounds. The effects of AP3, AP5 or CNQX on glutamate-, quisqualate- or trans-ACPD-stimulated fluorescence increases in cells transfected with mGluR5a2 were also investigated. Neither of these compounds (AP3, AP5 or CNQX) inhibited the agonist-induced fluorescence increases in these cells.

Dose-response studies in which the peak fluorescence values measured after application of varying amounts of glutamate, quisqualate or 1S,3R-ACPD to cells transfected with mGluR5a3 were compared revealed that the magnitude of the peak fluorescence increased with increasing concentration of each compound. Analysis of these data enabled a calculation of $EC_{50}$ values for each compound which were used in determining the relative potencies of the compounds.

HEK 293 cells transiently co-transfected with MMTV-hmGluR5a and pRShGR (a glucocorticoid receptor construct) were also analyzed in the fluorescence assay. The fluorescence of these cells increased in response to 100 µM quisqualate; the peak response was greater when the cells were preincubated with dexamethasone (~1 µM) for 16 hrs at 37° C. before being assayed.

b. Fluorescence imaging assay

HEK 293 cells that had been transiently transfected with mGluR5a3 and untransfected HEK 293 cells (control) were analyzed by digital video imaging in order to visualize metabotropic receptor-mediated changes in intracellular $Ca^{2+}$ concentration. Transfectants ($4-10^5$ cells per 35-mm culture dish with glass-insert bottom) were loaded with fura-2 by exposing the cells to 1 µM fura-2 (acetoxymethyl ester) for 25 min at room temperature in the dark. The cells were then washed three times with DMEM and four times with Ringer's (160 mM NaCl, 5 mM KCl, 2 mM $CaCl_2$, 1 mM $MgCl_2$, 11 mM glucose, 5 mM HEPES, pH 7.3) solution.

The transfectants and untransfected cells were then placed on the stage of an Axiovert 100 TV inverted microscope (Zeiss, Oberkochren, Germany) equipped with a 150 W xenon lamp as the UV light source. An Image 1 Fluor System (Universal Imaging, West Chester, Pa.) was used to control the alternate excitation of the cells at 340 and 380 nm (typically every 3 sec) through a 40X 1.3 N.A. oil immersion objective. Light emitted at greater than 510 nm was collected by a CCD 72 intensified CCD camera (MTI Dage, Michigan City, Ind.) and digitized. The background emitted light was subtracted from the 340 and 380 nm excitation images. The corrected values were used in calculating the 340/380 intensity ratio. These uncalibrated fura-2 ratio values were reliable indicators of changes in the intracellular $Ca^{2+}$ concentration.

The uncalibrated fura-2 ratios were used to generate pseudocolor images with purple corresponding to resting intracellular $Ca^{2+}$ concentration (~100 nM) and red to high intracellular $Ca^{2+}$ concentration (~1 µM). For quantitative analysis, the average ratio value in a 12-by-12 pixel region over each cell was calculated by the software for each ratio image in an experiment and imported into a spreadsheet for further analysis and graphing.

To demonstrate that HEK 293 cells express the intracellular components required in receptor-mediated activation of the PI hydrolysis/$Ca^{2+}$ mobilization pathway, transfectants and untransfected cells (which express endogenous G-protein-coupled muscarinic acetylcholine receptors) were exposed to 1 mM carbamylcholine (CCh; a muscarinic acetylcholine receptor agonist), and the cells were monitored for increases in intracellular $Ca^{2+}$ concentration. Typically, a detectable increase in the intracellular $Ca^{2+}$ concentration of the majority of the cells was observed in response to CCh addition in the imaging studies.

Both transfected and untransfected HEK 293 cells were also monitored for increases in intracellular $Ca^{2+}$ concentration in response to 100 μM quisqualate. On average, the intracellular $Ca^{2+}$ concentration of the untransfected cells did not change after exposure to $Ca^{2+}$ quisqualate. In contrast, the intracellular concentration of 26.7±22.3% of the transfected cells increased in response to application of 100 μM quisqualate.

2. Phosphatidylinositol hydrolyis ($Ip_1$) assays

Because activation of G-protein-coupled metabotropic receptors by agonists can lead to stimulation of the phosphatidylinositol (PI) hydrolysis pathway, methods of detecting increases in the products of PI hydrolysis (e.g., $IP_3$, $IP_2$ or $IP_1$) can be applied to the analysis of functional expression of metabotropic receptors that are coupled to the PI hydrolysis/$Ca^{2+}$ mobilization pathway or to both the PI hydrolysis/$Ca^{2+}$ mobilization pathway and the inhibitory cAMP cascade. One method for measuring $IP_1$ and/or $IP_2$ and/or $IP_3$ generated by hydrolysis of PI involves incorporation of [$^3$H]-myo-inositol into cell membrane phospholipids and subsequent separation of [$^3$H]-$IP_1$, [$^3$H]-$IP_2$ and [$^3$H]-$IP_3$, followed by quantitation of the radioactivity in each fraction, as follows.

HEK 293 cells that had been transiently transfected with mGluR5a3 were plated in 24-well microtiter plates at a density of 8×10$^5$ cells/well. After the cells were allowed to settle and adhere to the bottom of the plate for a few hours, 2 μCi of [$^3$H]-myo-inositol (Amersham catalog # PT6-271, Arlington Heights, Ill.; specific activity=17.7 Ci/mmol) was added to each well and incubated overnight at 37° C. The next day, the cells were examined under a Nikon Diaphot inverted microscope to assess the health of the cells morphologically as well as to determine if the wells contained a confluent layer of cells. Media was then aspirated and the cells were washed twice with 0.5 ml Krebs bicarbonate buffer [117.9 mM NaCl, 4.72 mM KCl, 2.54 mM $CaCl_2$, 1.18 mM $MgSO_4$, 1.19 mM $KH_2PO_4$, 25 mM $NaHCO_3$, 11.1 mM dextrose (equilibrated with 95% $O_2$, 5% $CO_2$, pH 7.4)]. The cells were incubated for 45 min. at room temperature. The buffer was then aspirated from each well and the cells were washed and incubated in 0.5 ml/well for 45 min at room temperature. The buffer was aspirated from each well, and the cells were then incubated for 20 min at 37° C. with 450 μl Krebs-bicarbonate buffer containing 10 mM LiCl instead of 10 mM NaCl (to block hydrolysis of $IP_1$ to inositol and inorganic phosphate) and 10 mM unlabeled myoinositol.

To begin treatment of the cells with metabotropic receptor-modulating compounds, 50 μl of Krebs-bicarbonate buffer (control) or 10× the final concentration of the compound was added to each well and the incubation was continued for 40 min. Incubation was terminated by addition of 1 ml ice-cold methanol to each well.

In order to isolate $IP_1$ from the cells, the cells were removed from the plates by scraping with plastic pipette tips, and the cell suspension was transferred to 12×75 mm glass tubes. The tubes were thoroughly vortexed, and a 150-μl aliquot, i.e., one-tenth of the total volume, of each reaction mixture was transferred to another tube for protein determination. The water-soluble inositol phosphates were separated from the radiolabelled membrane phospholipids by extraction in i ml chloroform. The tubes were incubated at room temperature for 30 min before centrifugation at 500 x g for 5 min at 4° C. The aqueous (top) layer containing the [$^3$H]-inositol phosphates was transferred to 10-ml syringes connected to Accell QMA SEP-PAK columns (Millipore; Calif.), which were attached to an Amersham Superseparator apparatus that was modified to allow collection into 20-ml scintillation vials. Water (10 ml) was added to the cartridge to remove [$^3$H]-inositol precursor, followed by 4 ml 0.02 M triethylammonium hydrogen carbonated buffer (TEAB, Fluka; N.Y.). To separately remove [$^3$H]-$IP_1$, [$^3$H]-$IP_2$ and [$^3$H]-$IP_3$ from the cartridge, 4 ml of 0.1 M TEAB, 4 ml of 0.3 M TEAB and 4 ml of 0.4 M TEAB were sequentially added to the cartridge and the separate eluate fractions were collected in large scintillation vials. Ecolume cocktail (15 ml; ICN; Calif.) was added to each vial for subsequent scintillation counting to determine the amount of each IP in the separate fractions. Protein concentration was determined using the Bio-Rad Protein Micro-Assay (Bio-Rad, Richmond, Calif.).

HEK 293 cells transiently transfected with 18 μg of mGluR5a3 displayed relatively high basal levels of $IP_1$ when analyzed in this assay. However, HEK 293 cells transiently transfected with 0.18 μg of mGluR5a3 exhibited lower basal $IP_1$ levels and detectable increases in $IP_1$ levels when treated with 1 mM glutamate, 1 mM quisqualate or 1 mM 1S, 3R-ACPD. The quisqualate-induced increase in $IP_1$ levels was not affected by 1 mMAP3.

Dose-response studies which compared the $IP_1$ levels measured after application of varying amounts of glutamate, quisqualate or 1S, 3R-ACPD to cells transfected with mGluR5a3 revealed that 3[$IP_1$ levels increased with increasing concentration of each compound. Analysis of these data enabled calculation of $EC_{50}$ values for each compound which were used in determining the relative potencies of the compounds.

3. Metabotropic Receptor Ligand Binding Assays

HEK cells transiently transfected with mGluR5a3 or with pUC19 (negative control) were analyzed for [$^3$H]-glutamate binding. Rat brain membranes were included in the binding assays as a positive control.

a. Preparation of Membranes i. Rat forebrain membranes

Rat forebrain membranes were prepared from rat brains as described by Schoepp et al. [(1992) Neurosci. Lett. 145:100]. Briefly, forebrains, consisting essentially of cerebral cortex, striatum and hippocampus, from ten rat brains were homogenized in 50 volumes of 30 mM ice-cold Tris-HCl containing 2.5 mM $CaCl_2$, pH 7.6 using a Polytron (Brinkman, Westbury, N.Y.). The homogenate was centrifuged at 30,000 x g for 15 minutes at 4° C. The supernatant was discarded, the pellet was resuspended in 50 volumes of buffer using a Polytron and the suspension was centrifuged at 30,000 x g for 15 min. This step was repeated twice. The pellet was resuspended in buffer and incubated at 37° C. for 30 min. The suspension was then centrifuged at 30,000 x g for 15 min. at 4° C. This step was repeated three times. The final pellet was resuspended in 15 volumes of 50mM Tris-HCl, pH 7.6, buffer, aliquoted, quick frozen and stored at −70° C.

ii. Membranes from Transfected and Untransfected HEK293 Cells

In order to prepare membranes from HEK 293 cells transfected with mGluR5a-encoding DNA or pUC19 (negative control), cells were scraped from the tissue culture plates, and the plates rinsed with 5 ml of PBS (phosphate-buffered saline: 137 mM NaCl, 2.7 mM KCl, 10 mM $Na_2HPO_4$, 1.7 mM $KH_2PO_4$). The cells were centrifuged at low speed in a table-top centrifuge, and the cell pellet was rinsed with PBS. The cell pellet was resuspended in 20 volumes of 50 mM Tris-HCl containing 0.5 mM PMSF, pH 7.6. The cells were homogenized on ice in a Dounce (teflon/glass) homogenizer using 10–20 strokes. The homogenate was centrifuged at 120,000 x g for 30 min. at 4° C. The final membrane pellet was resuspended in 50 mM Tris-HCl containing 0.5 mM PMSF, pH 7.6. The membrane preparations were aliquoted, quick-frozen, and stored at −70° C. The protein concentration was determined using the method of Bradford [(1976) Anal. Biochem. 72:2.48].

b. [$^3$H]-Glutamate binding assays

Specific binding of [$^3$H]-glutamate to metabotropic receptors in rat forebrain membranes was determined basically as described by Schoepp et al. (supra). On the day of the assay, frozen homogenate was thawed and washed three times with 50 mM Tris-HCl, pH 7.6. The final pellet was resuspended in 50 mM Tris-HCl, pH 7.6. The protein concentration was determined using the method of Bradford [(1976) Anal. Biochem. 72:248]. The suspension was centrifuged at 30,000 x g for 15 min. in order to be able to resuspend the pellet in the assay buffer (50 mM Tris-HCl, 0.5 mM PMSF, 0.1% BSA, pH 7.6) at a concentration of 1 mg/ml. The membrane suspension was incubated in triplicate with 10 or 100 nM [$^3$H]-glutamate (New England Nuclear, Boston, Mass.; catalog no. NET-490, specific activity=57.4 Ci/mmol) in a total volume of 0.5 ml assay buffer containing 100 μM NMDA (Sigma, St. Louis, Mo.), 100 μM AMPA and 100 μM kainate (Research Biochemicals Inc., Natick, Mass.) to block [$^3$H]-glutamate binding to ionotropic glutamate receptors and 100 μM SITS (Sigma, St. Louis, Mo.) to inhibit [$^3$H]-glutamate binding to chloride-dependent uptake sites for 45 min on ice. Bound radioactivity was separated from free radioactivity by centrifugation for 5 min. at 20,000 x g (4° C.) in an SM-24 rotor (Sorvall, Wilmington, Del.). The pellets were washed twice with 5–6 ml of ice-cold 50 mM Tris-HCl buffer, pH 7.6. The pellets were solubilized by vortexing in 5 ml of Ecolume scintillation cocktail. The radioactivity was measured in a Beckman scintillation counter. The nonspecific binding observed in the presence of 1 mM glutamate was subtracted from the total binding in order to determine specific binding.

Specific binding of [$^3$H]-glutamate to membranes prepared from HEK 293 cells transfected with mGluR5a-encoding DNA or pUC19 was determined essentially as described for measuring binding to rat brain membranes with minor modifications. On the day of the assay, frozen homogenate was thawed and centrifuged in a MR-150 high-speed refrigerated microcentrifuge (Peninsula Laboratories, Inc., Belmont, Calif.). The pellet was washed twice with assay buffer (50 mM Tris-HCl, 0.5 mM PMSF, 0.1% BSA, pH 7.6), and the final pellet was resuspended in assay buffer at a concentration of 1 mg/ml. NMDA, AMPA and kainate were excluded from the assay mixture when HEK 293 cell membranes were being analyzed for [$^3$H]-glutamate binding.

Specific binding of [$^3$H]-glutamate to rat brain membranes was measured using 200 μg of membrane and 100 nM [$^3$H]-glutamate. The ratio of total-to-nonspecific binding was approximately 2:1.

Specific binding of [$^3$H]-glutamate to membranes prepared from HEK 293 cells transfected with mGluR5a3 or pUC19 was measured using 200 μg of membranes and 100 nM [$^3$H]-glutamate. The amount of specific binding to membranes prepared from HEK 293 cells transfected with mGluR5a3 was significantly higher than that to membranes prepared from HEK 293 cells transfected with pUC19. Competitive binding studies were conducted in which the amount of specific binding of [$^3$H]-glutamate to membranes prepared from HEK 293 cells transfected with mGluR5a3 in the presence of various concentrations of unlabeled glutamate was determined. $IC_{50}$ values were calculated from the data obtained in these studies.

4. Cyclic AMP (cAMP) Assays

Because activation of some G-protein-coupled receptors results in decreases or increases in cAMP, assays that measure intracellular cAMP levels can also be used to evaluate recombinant human metabotropic receptors expressed in mammalian host cells. Mammalian cells transiently or stably transfected with human metabotropic receptor-encoding DNA or pUC19 (negative control) are plated in 24well microtiter plates at a density of $5\times10^5$ cells/well and allowed to incubate overnight. The following day, cells are examined under a Nikon Diaphot inverted microscope to assess the health of the cells morphologically as well as to determine if the wells contain a confluent layer of cells. Media is then aspirated and the cells are washed twice with 0.5 ml Krebs bicarbonate buffer (same buffer used in the PI hydrolysis assay; see Example 3.C.2) containing 1 mM IBMX (3-isobutyl-1-methylxanthine; Sigma, St. Louis, Mo.) and 0.1% BSA. Alternatively, 1X PBS can be used in place of Krebs bicarbonate buffer. Each wash is followed with a 30-min incubation at 37° C. The buffer is aspirated from each well and the cells are then incubated for 20 min at 37° C. with 0.2 ml Krebs-bicarbonate buffer containing 1 mM IBMX and 0.1% BSA.

To begin treatment of the cells with metabotropic receptor-modulating compounds, 50 μl of Krebs-bicarbonate buffer with or without 5X the final concentration of forskolin is added to some of the cells (basal control) and 5X the final concentration of the compound plus 5X the final concentration of forskolin is added to some cells (test cells) and the incubation is continued for 15 min at 37° C. At the end of this 15-min period, the reaction is terminated by adding 25 μl of 1% Triton X-100 solution and the incubation is continued for another 10 min. The lysed cells plus the cell suspension are transferred to 12×75 mm polypropylene tubes with plastic pipette tips. Each well is rinsed with 75 μl of Krebs-bicarbonate buffer containing 1 mM IBMX and 0.1% BSA. The rinse is combined with the cell lysate. The cell lysate suspension is centrifuged at 2300 x g for 5 min and the supernatant is assayed for cAMP levels using an RIA kit (Amersham Life Sciences catalog #TRK 432; Arlington Heights, Ill.).

5. Northern Blot Hybridization Analysis

Cells transfected with human metabotropic receptor-encoding DNA can also be analyzed for expression of the corresponding transcript by northern blot analysis. Total RNA was isolated from ~1×10$^7$ cells that have been transfected with the human metabotropic receptor-encoding DNA, and 10–15 μg of RNA is used for northern hybridization analysis. The inserts from human metabotropic receptor-encoding plasmids are nick-translated and used as probes. Typical conditions for northern blot hybridization and washing are as follows:

hybridization in 5x SSPE, 5X Denhart's solution, 50% formamide, at 42° C. followed by washing in 0.2x SSPE, 0.1% SDS, at 65° C.

While the invention has been described in detail with reference to certain preferred embodiments thereof, it will be understood that modifications and variations are within the spirit and scope of that which is described and claimed.

SUMMARY OF THE SEQUENCES

Sequence ID No. 1 is the nucleic acid sequence (and the deduced amino acid sequence) of a DNA encoding a metabotropic glutamate receptor subtype (mGluR1B) of the present invention.

Sequence ID No. 2 is the deduced amino acid sequence of the nucleotide sequence of Sequence ID No. 1.

Sequence ID No. 3 is a nucleotide sequence (and the deduced amino acid sequence) of a partial clone encoding a portion of an human mGluR2 receptor subtype.

Sequence ID No. 4 is the amino acid sequence of a portion of an human mGluR2 receptor subunit as encoded by the nucleotide sequence of Sequence ID No. 3.

Sequence ID No. 5 is the nucleic acid sequence (and the deduced amino acid sequence) of a DNA encoding a metabotropic glutamate receptor subtype (mGluR3) of the present invention.

Sequence ID No. 6 is the deduced amino acid sequence of the nucleotide sequence of Sequence ID No. 5.

Sequence ID No. 7 is the nucleic acid sequence (and the deduced amino acid sequence) of a DNA encoding a metabotropic glutamate receptor (mGluR5al) of the present invention.

Sequence ID No. 8 is the deduced amino acid sequence of the nucleotide sequence of Sequence ID No. 7.

Sequence ID No. 9 is the nucleic acid sequence (and the deduced amino acid sequence) of a DNA encoding an mGluR5 variant metabotropic glutamate receptor (mGluR5b) of the present invention.

Sequence ID No. 10 is the deduced amino acid sequence of the nucleotide sequence of Sequence ID No. 9.

Sequence ID No. 11 is the nucleic acid sequence (and the deduced amino acid sequence) of a DNA encoding an mGluR5 variant metabotropic glutamate receptor (mGluR5c) of the present invention.

Sequence ID No. 12 is the deduced amino acid sequence of the nucleotide sequence of Sequence ID No. 11.

Sequence ID No. 13 is 343 nucleotides of 3' untranslated sequence of an human mGluR2 receptor subtype.

---

That which is claimed is:

1. Nucleic acid encoding human metabotropic glutamate receptor subtype mGluR1, or the full complement of said nucleic acid, wherein said nucleic acid has the nucleotide sequence set forth in Sequence ID No. 1.

2. Nucleic acid encoding human metabotropic glutamate receptor subtype mGluR2, or the full complement of said nucleic acid.

3. Nucleic acid according to claim 2 wherein said nucleic acid or the full complement of said nucleic acid hybridizes under high stringency conditions to base 1 to base 354 of Sequence ID No. 3, or the human mGluR2-encoding portion of clone METAB40 (ATCC accession no. 75465).

4. Nucleic acid encoding human metabotropic glutamate receptor subtype mGluR3, or the full complement of said nucleic acid.

5. Nucleic acid according to claim 4 wherein said nucleic acid or the full complement of said nucleic acid hybridizes under high stringency conditions to base 1064 to base 3703 of Sequence ID No. 5.

6. Nucleic acid encoding human metabotropic glutamate receptor subtype mGluR5, or the full complement of said nucleic acid.

7. Nucleic acid according to claim 6 wherein said nucleic acid or the full complement of said nucleic acid hybridizes under high stringency conditions to base 370 to base 3912 of Sequence ID No. 7, base 370 to base 4008 of Sequence ID No. 9, or base 370 to base 3003 of Sequence ID No. 11.

8. Eukaryotic cells transfected with nucleic acid according to claim 1.

9. Eukaryotic cells expressing the human metabotropic glutamate receptor protein subtype of claim 1.

10. Amphibian oocytes transformed with nucleic acid according to claim 1, and expressing the human metabotropic glutamate receptor subtype encoded thereby.

11. Nucleic acid according to claim 1 wherein said nucleic acid encodes the amino acid sequence set forth in Sequence ID No. 2.

12. Nucleic acid according to claim 2 wherein said nucleic acid is characterized by encoding the amino acid sequence set forth in Sequence ID No. 4, or encoding the amino acid sequence of the human mGluR2-encoding portion of clone METAB40 (ATCC accession no. 75465).

13. Nucleic acid according to claim 2 wherein the nucleotide sequence of said nucleic acid is characterized as having the nucleotide sequence set forth in Sequence ID No. 3, or in the human mGluR2-encoding portion of clone METAB40 (ATCC accession no. 75465).

14. Nucleic acid according to claim 4 wherein said nucleic acid encodes the amino acid sequence set forth in Sequence ID No. 6.

15. Nucleic acid according to claim 4 wherein the nucleotide sequence of said nucleic acid is as set forth in Sequence ID No. 5.

16. Nucleic acid according to claim 6 wherein said nucleic acid encodes the amino acid sequence set forth in Sequence ID Nos. 8, 10 or 12.

17. Nucleic acid according to claim 6 wherein the nucleotide sequence of said nucleic acid is as set forth in Sequence ID Nos. 7, 9 or 11.

18. Eukaryotic cells transfected with nucleic acid according to claim 2.

19. Eukaryotic cells transfected with nucleic acid according to claim 4.

20. Eukaryotic cells transfected with nucleic acid according to claim 6.

21. Amphibian oocytes transformed with nucleic acid according to claim 2.

22. Amphibian oocytes transformed with nucleic acid according to claim 4.

23. Amphibian oocytes transformed with nucleic acid according to claim 16.

24. Nucleic acid according to claim 6 wherein mGluR5 is selected from the group of splice variants consisting of mGlura1, mGluR5a2, mGluRa3 mGluR5b and mGluR5c.

* * * * *

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 3330 base pairs
        ( B ) TYPE: nucleic acid
        ( C ) STRANDEDNESS: both
        ( D ) TOPOLOGY: both ( i i ) MOLECULE TYPE: cDNA ( i x ) FEATURE:
        ( A ) NAME/KEY: CDS
        ( B ) LOCATION: 405..3122
        ( D ) OTHER INFORMATION: /product="HUMAN MGLUR1B"

( x i ) SEQUENCE DESCRIPTION: SEQ ID NO:1:

```
GGTACGTACA  CTCGAGCGCC  GAGCGTGGCC  ACGGTCCTCT  GGCCCCGGGA  CCATAGCGCT           60

GTCTACCCCG  ACTCAGGTAC  TCAGCATCTA  GCTCACCGCT  GCCAACACGA  CTTCCACTGT          120

ACTCTTGATC  AATTTACCTT  GATGCACTAC  CGGTGAAGAA  CGGGGACTCG  AATTCCCTTA          180

CAAACGCCTC  CAGCTTGTAG  AGGCGGTCGT  GGAGGACCCA  GAGGAGGAGA  CGAAGGGGAA          240

GGAGGCGGTG  GTGGAGGAGG  CAAAGGCCTT  GGACGACCAT  TGTTGGCGAG  GGGCACCACT          300

CCGGGAGAGG  CGGCGCTGGG  CGTCTTGGGG  GTGCGCGCCG  GGAGCCTGCA  GCGGGACCAG          360

CGTGGGAACG  CGGCTGGCAG  GCTGTGGACC  TCGTCCTCAC  CACC ATG GTC GGG CTC           416
                                                  Met Val Gly Leu
                                                    1

CTT TTG TTT TTT TTC CCA GCG ATC TTT TTG GAG GTG TCC CTT CTC CCC                464
```

|     |     |     |     |     |     |     |     |     |     |     |     |     |     |     |     |
|---|---|---|---|---|---|---|---|---|---|---|---|---|---|---|---|
| Leu | Leu | Phe | Phe | Phe | Pro | Ala | Ile | Phe | Leu | Glu | Val | Ser | Leu | Leu | Pro |
| 5 | | | | | 10 | | | | | 15 | | | | | 20 |

| AGA | AGC | CCC | GGC | AGG | AAA | GTG | TTG | CTG | GCA | GGA | GCG | TCG | TCT | CAG | CGC | 512 |
|---|---|---|---|---|---|---|---|---|---|---|---|---|---|---|---|---|
| Arg | Ser | Pro | Gly | Arg | Lys | Val | Leu | Leu | Ala | Gly | Ala | Ser | Ser | Gln | Arg | |
| | | | | 25 | | | | | 30 | | | | | 35 | | |

| TCG | GTG | GCC | AGA | ATG | GAC | GGA | GAT | GTC | ATC | ATC | GGA | GCC | CTC | TTC | TCA | 560 |
|---|---|---|---|---|---|---|---|---|---|---|---|---|---|---|---|---|
| Ser | Val | Ala | Arg | Met | Asp | Gly | Asp | Val | Ile | Ile | Gly | Ala | Leu | Phe | Ser | |
| | | | | 40 | | | | | 45 | | | | | 50 | | |

| GTC | CAT | CAC | CAG | CCT | CCA | GCC | GAG | AAA | GTA | CCC | GAG | AGG | AAG | TGT | GGG | 608 |
|---|---|---|---|---|---|---|---|---|---|---|---|---|---|---|---|---|
| Val | His | His | Gln | Pro | Pro | Ala | Glu | Lys | Val | Pro | Glu | Arg | Lys | Cys | Gly | |
| | | 55 | | | | | 60 | | | | | 65 | | | | |

| GAG | ATC | AGG | GAG | CAG | TAT | GGC | ATC | CAG | AGG | GTG | GAG | GCC | ATG | TTC | CAC | 656 |
|---|---|---|---|---|---|---|---|---|---|---|---|---|---|---|---|---|
| Glu | Ile | Arg | Glu | Gln | Tyr | Gly | Ile | Gln | Arg | Val | Glu | Ala | Met | Phe | His | |
| | | 70 | | | | | 75 | | | | | 80 | | | | |

| ACG | TTG | GAT | AAG | ATC | AAC | GCG | GAC | CCG | GTC | CTC | CTG | CCC | AAC | ATC | ACC | 704 |
|---|---|---|---|---|---|---|---|---|---|---|---|---|---|---|---|---|
| Thr | Leu | Asp | Lys | Ile | Asn | Ala | Asp | Pro | Val | Leu | Leu | Pro | Asn | Ile | Thr | |
| 85 | | | | | 90 | | | | | 95 | | | | | 100 | |

| CTG | GGC | AGT | GAG | ATC | CGG | GAC | TCC | TGC | TGG | CAC | TCT | TCC | GTG | GCT | CTG | 752 |
|---|---|---|---|---|---|---|---|---|---|---|---|---|---|---|---|---|
| Leu | Gly | Ser | Glu | Ile | Arg | Asp | Ser | Cys | Trp | His | Ser | Ser | Val | Ala | Leu | |
| | | | | 105 | | | | | 110 | | | | | 115 | | |

| GAA | CAG | AGC | ATT | GAG | TTC | ATT | AGG | GAC | TCT | CTG | AGG | CCC | ATC | CGA | GAT | 800 |
|---|---|---|---|---|---|---|---|---|---|---|---|---|---|---|---|---|
| Glu | Gln | Ser | Ile | Glu | Phe | Ile | Arg | Asp | Ser | Leu | Arg | Pro | Ile | Arg | Asp | |
| | | | 120 | | | | | 125 | | | | | 130 | | | |

| GAG | AAG | GAT | GGG | ATC | AAC | CGG | TGT | CTG | CCT | GAC | GGC | CAG | TCC | CTC | CCC | 848 |
|---|---|---|---|---|---|---|---|---|---|---|---|---|---|---|---|---|
| Glu | Lys | Asp | Gly | Ile | Asn | Arg | Cys | Leu | Pro | Asp | Gly | Gln | Ser | Leu | Pro | |
| | | 135 | | | | | 140 | | | | | 145 | | | | |

| CCA | GGC | AGG | GCT | AAG | AAG | CCC | ATT | GCG | GGA | GTG | ATC | GGT | GCC | GGC | TCC | 896 |
|---|---|---|---|---|---|---|---|---|---|---|---|---|---|---|---|---|
| Pro | Gly | Arg | Ala | Lys | Lys | Pro | Ile | Ala | Gly | Val | Ile | Gly | Ala | Gly | Ser | |
| | | 150 | | | | | 155 | | | | | 160 | | | | |

| AGC | TCT | GTA | GCC | ATT | CAA | GTG | CAG | AAC | CTG | CTC | CAG | CTC | TTC | GAC | ATC | 944 |
|---|---|---|---|---|---|---|---|---|---|---|---|---|---|---|---|---|
| Ser | Ser | Val | Ala | Ile | Gln | Val | Gln | Asn | Leu | Leu | Gln | Leu | Phe | Asp | Ile | |
| 165 | | | | | 170 | | | | | 175 | | | | | 180 | |

| CCC | CAG | ATC | GCT | TAT | TCA | GCC | ACA | AGC | ATC | GAC | CTG | AGT | GAC | AAA | ACT | 992 |
|---|---|---|---|---|---|---|---|---|---|---|---|---|---|---|---|---|
| Pro | Gln | Ile | Ala | Tyr | Ser | Ala | Thr | Ser | Ile | Asp | Leu | Ser | Asp | Lys | Thr | |
| | | | | 185 | | | | | 190 | | | | | 195 | | |

| TTG | TAC | AAA | TAC | TTC | CTG | AGG | GTG | GTC | CCT | TCT | GAC | ACT | TTG | CAG | GCA | 1040 |
|---|---|---|---|---|---|---|---|---|---|---|---|---|---|---|---|---|
| Leu | Tyr | Lys | Tyr | Phe | Leu | Arg | Val | Val | Pro | Ser | Asp | Thr | Leu | Gln | Ala | |
| | | | 200 | | | | | 205 | | | | | 210 | | | |

| AGG | GCG | ATG | CTT | GAC | ATA | GTC | AAA | CGT | TAC | AAT | TGG | ACC | TAT | GTC | TCT | 1088 |
|---|---|---|---|---|---|---|---|---|---|---|---|---|---|---|---|---|
| Arg | Ala | Met | Leu | Asp | Ile | Val | Lys | Arg | Tyr | Asn | Trp | Thr | Tyr | Val | Ser | |
| | | | 215 | | | | | 220 | | | | | 225 | | | |

| GCA | GTC | CAC | ACG | GAA | GGG | AAT | TAT | GGC | GAG | AGC | GGA | ATG | GAC | GCT | TCC | 1136 |
|---|---|---|---|---|---|---|---|---|---|---|---|---|---|---|---|---|
| Ala | Val | His | Thr | Glu | Gly | Asn | Tyr | Gly | Glu | Ser | Gly | Met | Asp | Ala | Ser | |
| | | 230 | | | | | 235 | | | | | 240 | | | | |

| ACA | GAG | CTG | GCT | GTC | CAG | GAA | GGC | CTC | TGT | TTC | GCC | CAT | TCT | GAC | AAA | 1184 |
|---|---|---|---|---|---|---|---|---|---|---|---|---|---|---|---|---|
| Thr | Glu | Leu | Ala | Val | Gln | Glu | Gly | Leu | Cys | Phe | Ala | His | Ser | Asp | Lys | |
| 245 | | | | | 250 | | | | | 255 | | | | | 260 | |

| ATC | TAC | AGC | AAC | GCT | GGG | GAG | AAG | AGC | TTT | GAC | CGG | CTC | TTG | TGC | ACA | 1232 |
|---|---|---|---|---|---|---|---|---|---|---|---|---|---|---|---|---|
| Ile | Tyr | Ser | Asn | Ala | Gly | Glu | Lys | Ser | Phe | Asp | Arg | Leu | Leu | Cys | Thr | |
| | | | | 265 | | | | | 270 | | | | | 275 | | |

| CTC | CGA | GAG | AGG | CTT | CCC | AAG | GTT | AGA | GTT | GTG | GTC | TGC | TTC | TGT | GAA | 1280 |
|---|---|---|---|---|---|---|---|---|---|---|---|---|---|---|---|---|
| Leu | Arg | Glu | Arg | Leu | Pro | Lys | Val | Arg | Val | Val | Val | Cys | Phe | Cys | Glu | |
| | | | 280 | | | | | 285 | | | | | 290 | | | |

| GGC | ATG | ACA | GTG | CGA | GGA | CTC | CTG | AGC | GCC | ATG | CGG | CGC | CTT | GGC | GTC | 1328 |
|---|---|---|---|---|---|---|---|---|---|---|---|---|---|---|---|---|
| Gly | Met | Thr | Val | Arg | Gly | Leu | Leu | Ser | Ala | Met | Arg | Arg | Leu | Gly | Val | |
| | | 295 | | | | | 300 | | | | | 305 | | | | |

| GTG | GGC | GAG | TTC | TCA | CTC | ATT | GGA | AGT | GAT | GGA | TGG | GCA | GAC | AGA | GAT | 1376 |
|---|---|---|---|---|---|---|---|---|---|---|---|---|---|---|---|---|
| Val | Gly | Glu | Phe | Ser | Leu | Ile | Gly | Ser | Asp | Gly | Trp | Ala | Asp | Arg | Asp | |
| | 310 | | | | | 315 | | | | | 320 | | | | | |

| GAA | GTC | ATT | GAA | GGT | TAT | GAG | GTG | GAA | GCC | AAC | GGG | GGA | ATC | ACG | ATA | 1424 |
|---|---|---|---|---|---|---|---|---|---|---|---|---|---|---|---|---|

|     |     |     |     |     |     |     |     |     |     |     |     |     |     |     |     |
|-----|-----|-----|-----|-----|-----|-----|-----|-----|-----|-----|-----|-----|-----|-----|-----|
| Glu | Val | Ile | Glu | Gly | Tyr | Glu | Val | Glu | Ala | Asn | Gly | Gly | Ile | Thr | Ile |
| 325 |     |     |     | 330 |     |     |     |     | 335 |     |     |     |     | 340 |     |

```
AAG CTG CAG TCT CCA GAG GTC AGG TCA TTT GAT GAT TAT TTC CTG AAA           1472
Lys Leu Gln Ser Pro Glu Val Arg Ser Phe Asp Asp Tyr Phe Leu Lys
            345             350             355

CTG AGG CTG GCA CAC AAC ACG AGG AAT CCC TGG TTC CCT GAG TTC TGG           1520
Leu Arg Leu Ala His Asn Thr Arg Asn Pro Trp Phe Pro Glu Phe Trp
                360             365             370

AAA CAT CGC TTC CAG TGC CGC CTT CCA GGA CAC CTT CTG GAA AAT CCC           1568
Lys His Arg Phe Gln Cys Arg Leu Pro Gly His Leu Leu Glu Asn Pro
        375             380             385

AAC TTT AAA CGA ATC TGC ACA GGC AAT GAA AGC TTA GAA GAA AAC TAT           1616
Asn Phe Lys Arg Ile Cys Thr Gly Asn Glu Ser Leu Glu Glu Asn Tyr
    390             395             400

GTC CAG GAC AGT AAG ATG GGG TTT GTC ATC AAT GCC ATC TAT GCC ATG           1664
Val Gln Asp Ser Lys Met Gly Phe Val Ile Asn Ala Ile Tyr Ala Met
405             410             415             420

GAA CAT GGG CTG CAG AAC ATG CAC CAT CCC CTC TGC CCC TGG CAC GTG           1712
Glu His Gly Leu Gln Asn Met His His Pro Leu Cys Pro Trp His Val
                425             430             435

GGC CTC TGT GAT GCC ATG AAG CCC ATC GAC GGC AGC AAG CTG CTG GAC           1760
Gly Leu Cys Asp Ala Met Lys Pro Ile Asp Gly Ser Lys Leu Leu Asp
        440             445             450

TTC CTC ATC AAG TCC TCA TTC ATT GGA GTA TCT GGA GAG GAG GTG TGG           1808
Phe Leu Ile Lys Ser Ser Phe Ile Gly Val Ser Gly Glu Glu Val Trp
    455             460             465

TTT GAT GAG AAA GGA GAC GCT CCT GGA AGG TAT GAT ATC ATG AAT CTG           1856
Phe Asp Glu Lys Gly Asp Ala Pro Gly Arg Tyr Asp Ile Met Asn Leu
470             475             480

CAG TAC ACT GAA GCT AAT CGC TAT GAC TAT GTG CAC GTT GGA ACC TGG           1904
Gln Tyr Thr Glu Ala Asn Arg Tyr Asp Tyr Val His Val Gly Thr Trp
485             490             495             500

CAT GAA GGA GTG CTG AAC ATT GAT GAT TAC AAA ATC CAG ATG AAC AAG           1952
His Glu Gly Val Leu Asn Ile Asp Asp Tyr Lys Ile Gln Met Asn Lys
                505             510             515

AGT GGA GTG GTG CGG TCT GTG TGC AGT GAG CCT TGC TTA AAG GGC CAG           2000
Ser Gly Val Val Arg Ser Val Cys Ser Glu Pro Cys Leu Lys Gly Gln
        520             525             530

ATT AAG GTT ATA CGG AAA GGA GAA GTG AGC TGC TGC TGG ATT TGC ACG           2048
Ile Lys Val Ile Arg Lys Gly Glu Val Ser Cys Cys Trp Ile Cys Thr
    535             540             545

GCC TCC AAA GAG AAT GAA TTT GTC CAA GAT GAG TTC ACC CGC AAA GCT           2096
Ala Ser Lys Glu Asn Glu Phe Val Gln Asp Glu Phe Thr Arg Lys Ala
550             555             560

TGT GAC TTG GGA TGG TGG CCC AAT GCA GCT CTT ACA GGG TGT GAG CCC           2144
Cys Asp Leu Gly Trp Trp Pro Asn Ala Ala Leu Thr Gly Cys Glu Pro
565             570             575             580

ACT CCC CGT TAT CTT GAG TGG AGT GAC ATA GAA TCC ATT ATA GCC ATC           2192
Thr Pro Arg Tyr Leu Glu Trp Ser Asp Ile Glu Ser Ile Ile Ala Ile
                585             590             595

GCC TTT TCA TGC CTG GGA ATC CTT GTT ACC TTG TTT GTC ACC CTA ATC           2240
Ala Phe Ser Cys Leu Gly Ile Leu Val Thr Leu Phe Val Thr Leu Ile
        600             605             610

TTC GTA CTG TAC CGG GAA ACA CCA GTG GTC AAA TCC TCC AGT CGG GAG           2288
Phe Val Leu Tyr Arg Glu Thr Pro Val Val Lys Ser Ser Ser Arg Glu
    615             620             625

CTC TGC TAC ATC ATC CTA GCT GGC ATC TTC CTT GGT TAT GTG TGC CCA           2336
Leu Cys Tyr Ile Ile Leu Ala Gly Ile Phe Leu Gly Tyr Val Cys Pro
630             635             640

TTC ACT CTC ATT GCC AAA CCT ACT ACC ACA TCC TGG AGC CTC CAG CGC           2384
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| Phe | Thr | Leu | Ile | Ala | Lys | Pro | Thr | Thr | Thr | Ser | Trp | Ser | Leu | Gln | Arg |      |
| 645 |     |     |     |     | 650 |     |     |     | 655 |     |     |     |     |     | 660 |      |
| CTC | TTG | GTT | GGC | CTC | TCC | TCT | GCG | ATG | TGC | TAC | TCT | GCT | TTA | GTG | ACT | 2432 |
| Leu | Leu | Val | Gly | Leu | Ser | Ser | Ala | Met | Cys | Tyr | Ser | Ala | Leu | Val | Thr |      |
|     |     |     |     | 665 |     |     |     |     | 670 |     |     |     |     | 675 |     |      |
| AAA | ACC | AAT | CGT | ATT | GAA | CGC | ATC | CTG | GCT | GGC | AGC | AAG | AAG | AAG | ATC | 2480 |
| Lys | Thr | Asn | Arg | Ile | Glu | Arg | Ile | Leu | Ala | Gly | Ser | Lys | Lys | Lys | Ile |      |
|     |     |     | 680 |     |     |     |     | 685 |     |     |     |     | 690 |     |     |      |
| TGC | ACC | CGG | AAG | CCC | AGG | TTC | ATG | AGT | GCC | TGG | GCT | CAG | GTG | ATC | ATT | 2528 |
| Cys | Thr | Arg | Lys | Pro | Arg | Phe | Met | Ser | Ala | Trp | Ala | Gln | Val | Ile | Ile |      |
|     |     | 695 |     |     |     |     | 700 |     |     |     |     | 705 |     |     |     |      |
| GCC | TCA | ATT | CTG | ATT | AGT | GTG | CAA | CTA | ACC | CTG | GTG | GTA | ACC | CTG | ATC | 2576 |
| Ala | Ser | Ile | Leu | Ile | Ser | Val | Gln | Leu | Thr | Leu | Val | Val | Thr | Leu | Ile |      |
|     | 710 |     |     |     |     | 715 |     |     |     |     | 720 |     |     |     |     |      |
| ATC | ATG | GAA | CCC | CCT | ATG | CCC | ATT | CTG | TCC | TAC | CCA | AGT | ATC | AAG | GAA | 2624 |
| Ile | Met | Glu | Pro | Pro | Met | Pro | Ile | Leu | Ser | Tyr | Pro | Ser | Ile | Lys | Glu |      |
| 725 |     |     |     |     | 730 |     |     |     | 735 |     |     |     |     |     | 740 |      |
| GTC | TAC | CTT | ATC | TGC | AAT | ACC | AGC | AAC | CTG | GGT | GTG | GTG | GCC | CCT | TGG | 2672 |
| Val | Tyr | Leu | Ile | Cys | Asn | Thr | Ser | Asn | Leu | Gly | Val | Val | Ala | Pro | Trp |      |
|     |     |     |     | 745 |     |     |     | 750 |     |     |     |     | 755 |     |     |      |
| GGC | TAC | AAT | GGA | CTC | CTC | ATC | ATG | AGC | TGT | ACC | TAC | TAT | GCC | TTC | AAG | 2720 |
| Gly | Tyr | Asn | Gly | Leu | Leu | Ile | Met | Ser | Cys | Thr | Tyr | Tyr | Ala | Phe | Lys |      |
|     |     |     | 760 |     |     |     |     | 765 |     |     |     |     | 770 |     |     |      |
| ACC | CGC | AAC | GTG | CCC | GCC | AAC | TTC | AAT | GAG | GCC | AAA | TAT | TTC | GCG | TTC | 2768 |
| Thr | Arg | Asn | Val | Pro | Ala | Asn | Phe | Asn | Glu | Ala | Lys | Tyr | Phe | Ala | Phe |      |
|     |     | 775 |     |     |     |     | 780 |     |     |     |     | 785 |     |     |     |      |
| ACC | ATG | TAC | ACC | ACC | TGT | ATC | ATC | TGG | CTA | GCT | TTG | GGG | CCC | ATT | TAC | 2816 |
| Thr | Met | Tyr | Thr | Thr | Cys | Ile | Ile | Trp | Leu | Ala | Leu | Gly | Pro | Ile | Tyr |      |
|     | 790 |     |     |     |     | 795 |     |     |     |     | 800 |     |     |     |     |      |
| TTT | GGG | AGC | AAC | TAC | AAG | ATC | ATC | ACA | ACT | TGC | TTT | GGA | GTG | AGT | CTC | 2864 |
| Phe | Gly | Ser | Asn | Tyr | Lys | Ile | Ile | Thr | Thr | Cys | Phe | Gly | Val | Ser | Leu |      |
| 805 |     |     |     |     | 810 |     |     |     | 815 |     |     |     |     |     | 820 |      |
| AGT | GTA | ACA | GTG | GCT | CTG | GGG | TGC | ATG | TTC | ACT | CCC | AAG | ATG | TAC | ATC | 2912 |
| Ser | Val | Thr | Val | Ala | Leu | Gly | Cys | Met | Phe | Thr | Pro | Lys | Met | Tyr | Ile |      |
|     |     |     |     | 825 |     |     |     |     | 830 |     |     |     |     | 835 |     |      |
| ATT | ATT | GCC | AAG | CCT | GAG | AGG | AAT | GTC | CGC | AGT | GCC | TTC | ACC | ACC | TCT | 2960 |
| Ile | Ile | Ala | Lys | Pro | Glu | Arg | Asn | Val | Arg | Ser | Ala | Phe | Thr | Thr | Ser |      |
|     |     |     | 840 |     |     |     |     | 845 |     |     |     |     | 850 |     |     |      |
| GAT | GTT | GTC | CGC | ATG | CAT | GTT | GGC | GAT | GGC | AAA | GTG | CCC | TGC | CGC | TCC | 3008 |
| Asp | Val | Val | Arg | Met | His | Val | Gly | Asp | Gly | Lys | Val | Pro | Cys | Arg | Ser |      |
|     |     | 855 |     |     |     |     | 860 |     |     |     |     | 865 |     |     |     |      |
| AAC | ACT | TTC | CTC | AAC | ATC | TTC | CGA | AGA | AAG | AAG | GCA | GGG | GCA | GGG | AAT | 3056 |
| Asn | Thr | Phe | Leu | Asn | Ile | Phe | Arg | Arg | Lys | Lys | Ala | Gly | Ala | Gly | Asn |      |
|     | 870 |     |     |     |     | 875 |     |     |     |     | 880 |     |     |     |     |      |
| GCC | AAG | AAG | AGG | CAG | CCA | GAA | TTC | TCG | CCC | ACC | AGC | CAA | TGT | CCG | TCG | 3104 |
| Ala | Lys | Lys | Arg | Gln | Pro | Glu | Phe | Ser | Pro | Thr | Ser | Gln | Cys | Pro | Ser |      |
| 885 |     |     |     |     | 890 |     |     |     | 895 |     |     |     |     |     | 900 |      |
| GCA | CAT | GTG | CAG | CTT | TGAAACCCC | CACACTGCAG | TGAATGTTTC | TAACGGCAAG |     |     |     |     |     |     |     | 3159 |
| Ala | His | Val | Gln | Leu |     |     |     |     |     |     |     |     |     |     |     |      |
|     |     |     |     | 905 |     |     |     |     |     |     |     |     |     |     |     |      |

```
TCTGTGTCAT GGTCTGAACC AGGTGGAGGA CAGGTGCCCA AGGGACAGCA CATGTGGCAC    3219

CGCCTCTCTG TGCACGTGAA GACCAATGAG ACGGCCTGCA ACCAAACAGC CGTCATCAAA    3279

CCCCTCACTA AAAGTTACCA AGGCTCTGGC AAGAGCCTGA CCTTTTCAGA T             3330
```

( 2 ) INFORMATION FOR SEQ ID NO:2:

( i ) SEQUENCE CHARACTERISTICS:
        ( A ) LENGTH: 905 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | Val | Gly | Leu | Leu | Leu | Phe | Phe | Phe | Pro | Ala | Ile | Phe | Leu | Glu | Val |
|---|---|---|---|---|---|---|---|---|---|---|---|---|---|---|---|
| 1 | | | | 5 | | | | | 10 | | | | | 15 | |
| Ser | Leu | Leu | Pro | Arg | Ser | Pro | Gly | Arg | Lys | Val | Leu | Leu | Ala | Gly | Ala |
| | | | 20 | | | | | 25 | | | | | 30 | | |
| Ser | Ser | Gln | Arg | Ser | Val | Ala | Arg | Met | Asp | Gly | Asp | Val | Ile | Ile | Gly |
| | | 35 | | | | | 40 | | | | | 45 | | | |
| Ala | Leu | Phe | Ser | Val | His | His | Gln | Pro | Pro | Ala | Glu | Lys | Val | Pro | Glu |
| | 50 | | | | | 55 | | | | | 60 | | | | |
| Arg | Lys | Cys | Gly | Glu | Ile | Arg | Glu | Gln | Tyr | Gly | Ile | Gln | Arg | Val | Glu |
| 65 | | | | | 70 | | | | | 75 | | | | | 80 |
| Ala | Met | Phe | His | Thr | Leu | Asp | Lys | Ile | Asn | Ala | Asp | Pro | Val | Leu | Leu |
| | | | | 85 | | | | | 90 | | | | | 95 | |
| Pro | Asn | Ile | Thr | Leu | Gly | Ser | Glu | Ile | Arg | Asp | Ser | Cys | Trp | His | Ser |
| | | | 100 | | | | | 105 | | | | | 110 | | |
| Ser | Val | Ala | Leu | Glu | Gln | Ser | Ile | Glu | Phe | Ile | Arg | Asp | Ser | Leu | Arg |
| | | | 115 | | | | | 120 | | | | | 125 | | |
| Pro | Ile | Arg | Asp | Glu | Lys | Asp | Gly | Ile | Asn | Arg | Cys | Leu | Pro | Asp | Gly |
| | 130 | | | | | 135 | | | | | 140 | | | | |
| Gln | Ser | Leu | Pro | Pro | Gly | Arg | Ala | Lys | Lys | Pro | Ile | Ala | Gly | Val | Ile |
| 145 | | | | | 150 | | | | | 155 | | | | | 160 |
| Gly | Ala | Gly | Ser | Ser | Ser | Val | Ala | Ile | Gln | Val | Gln | Asn | Leu | Leu | Gln |
| | | | | 165 | | | | | 170 | | | | | 175 | |
| Leu | Phe | Asp | Ile | Pro | Gln | Ile | Ala | Tyr | Ser | Ala | Thr | Ser | Ile | Asp | Leu |
| | | | 180 | | | | | 185 | | | | | 190 | | |
| Ser | Asp | Lys | Thr | Leu | Tyr | Lys | Tyr | Phe | Leu | Arg | Val | Val | Pro | Ser | Asp |
| | | 195 | | | | | 200 | | | | | 205 | | | |
| Thr | Leu | Gln | Ala | Arg | Ala | Met | Leu | Asp | Ile | Val | Lys | Arg | Tyr | Asn | Trp |
| | 210 | | | | | 215 | | | | | 220 | | | | |
| Thr | Tyr | Val | Ser | Ala | Val | His | Thr | Glu | Gly | Asn | Tyr | Gly | Glu | Ser | Gly |
| 225 | | | | | 230 | | | | | 235 | | | | | 240 |
| Met | Asp | Ala | Ser | Thr | Glu | Leu | Ala | Val | Gln | Glu | Gly | Leu | Cys | Phe | Ala |
| | | | | 245 | | | | | 250 | | | | | 255 | |
| His | Ser | Asp | Lys | Ile | Tyr | Ser | Asn | Ala | Gly | Glu | Lys | Ser | Phe | Asp | Arg |
| | | | 260 | | | | | 265 | | | | | 270 | | |
| Leu | Leu | Cys | Thr | Leu | Arg | Glu | Arg | Leu | Pro | Lys | Val | Arg | Val | Val | Val |
| | | 275 | | | | | 280 | | | | | 285 | | | |
| Cys | Phe | Cys | Glu | Gly | Met | Thr | Val | Arg | Gly | Leu | Leu | Ser | Ala | Met | Arg |
| | 290 | | | | | 295 | | | | | 300 | | | | |
| Arg | Leu | Gly | Val | Val | Gly | Glu | Phe | Ser | Leu | Ile | Gly | Ser | Asp | Gly | Trp |
| 305 | | | | | 310 | | | | | 315 | | | | | 320 |
| Ala | Asp | Arg | Asp | Glu | Val | Ile | Glu | Gly | Tyr | Glu | Val | Glu | Ala | Asn | Gly |
| | | | | 325 | | | | | 330 | | | | | 335 | |
| Gly | Ile | Thr | Ile | Lys | Leu | Gln | Ser | Pro | Glu | Val | Arg | Ser | Phe | Asp | Asp |
| | | | 340 | | | | | 345 | | | | | 350 | | |
| Tyr | Phe | Leu | Lys | Leu | Arg | Leu | Ala | His | Asn | Thr | Arg | Asn | Pro | Trp | Phe |
| | | 355 | | | | | 360 | | | | | 365 | | | |
| Pro | Glu | Phe | Trp | Lys | His | Arg | Phe | Gln | Cys | Arg | Leu | Pro | Gly | His | Leu |
| | 370 | | | | | 375 | | | | | 380 | | | | |
| Leu | Glu | Asn | Pro | Asn | Phe | Lys | Arg | Ile | Cys | Thr | Gly | Asn | Glu | Ser | Leu |
| 385 | | | | | 390 | | | | | 395 | | | | | 400 |

```
Glu Glu Asn Tyr Val Gln Asp Ser Lys Met Gly Phe Val Ile Asn Ala
                405                 410                 415

Ile Tyr Ala Met Glu His Gly Leu Gln Asn Met His His Pro Leu Cys
            420                 425                 430

Pro Trp His Val Gly Leu Cys Asp Ala Met Lys Pro Ile Asp Gly Ser
        435                 440                 445

Lys Leu Leu Asp Phe Leu Ile Lys Ser Ser Phe Ile Gly Val Ser Gly
    450                 455                 460

Glu Glu Val Trp Phe Asp Glu Lys Gly Asp Ala Pro Gly Arg Tyr Asp
465                 470                 475                 480

Ile Met Asn Leu Gln Tyr Thr Glu Ala Asn Arg Tyr Asp Tyr Val His
            485                 490                 495

Val Gly Thr Trp His Glu Gly Val Leu Asn Ile Asp Asp Tyr Lys Ile
        500                 505                 510

Gln Met Asn Lys Ser Gly Val Val Arg Ser Val Cys Ser Glu Pro Cys
        515                 520                 525

Leu Lys Gly Gln Ile Lys Val Ile Arg Lys Gly Glu Val Ser Cys Cys
    530                 535                 540

Trp Ile Cys Thr Ala Ser Lys Glu Asn Glu Phe Val Gln Asp Glu Phe
545                 550                 555                 560

Thr Arg Lys Ala Cys Asp Leu Gly Trp Trp Pro Asn Ala Ala Leu Thr
            565                 570                 575

Gly Cys Glu Pro Thr Pro Arg Tyr Leu Glu Trp Ser Asp Ile Glu Ser
        580                 585                 590

Ile Ile Ala Ile Ala Phe Ser Cys Leu Gly Ile Leu Val Thr Leu Phe
    595                 600                 605

Val Thr Leu Ile Phe Val Leu Tyr Arg Glu Thr Pro Val Val Lys Ser
    610                 615                 620

Ser Ser Arg Glu Leu Cys Tyr Ile Ile Leu Ala Gly Ile Phe Leu Gly
625                 630                 635                 640

Tyr Val Cys Pro Phe Thr Leu Ile Ala Lys Pro Thr Thr Thr Ser Trp
            645                 650                 655

Ser Leu Gln Arg Leu Leu Val Gly Leu Ser Ser Ala Met Cys Tyr Ser
        660                 665                 670

Ala Leu Val Thr Lys Thr Asn Arg Ile Glu Arg Ile Leu Ala Gly Ser
        675                 680                 685

Lys Lys Lys Ile Cys Thr Arg Lys Pro Arg Phe Met Ser Ala Trp Ala
    690                 695                 700

Gln Val Ile Ile Ala Ser Ile Leu Ile Ser Val Gln Leu Thr Leu Val
705                 710                 715                 720

Val Thr Leu Ile Ile Met Glu Pro Pro Met Pro Ile Leu Ser Tyr Pro
            725                 730                 735

Ser Ile Lys Glu Val Tyr Leu Ile Cys Asn Thr Ser Asn Leu Gly Val
            740                 745                 750

Val Ala Pro Trp Gly Tyr Asn Gly Leu Leu Ile Met Ser Cys Thr Tyr
        755                 760                 765

Tyr Ala Phe Lys Thr Arg Asn Val Pro Ala Asn Phe Asn Glu Ala Lys
770                 775                 780

Tyr Phe Ala Phe Thr Met Tyr Thr Thr Cys Ile Ile Trp Leu Ala Leu
785                 790                 795                 800

Gly Pro Ile Tyr Phe Gly Ser Asn Tyr Lys Ile Ile Thr Thr Cys Phe
        805                 810                 815

Gly Val Ser Leu Ser Val Thr Val Ala Leu Gly Cys Met Phe Thr Pro
        820                 825                 830
```

```
Lys  Met  Tyr  Ile  Ile  Ile  Ala  Lys  Pro  Glu  Arg  Asn  Val  Arg  Ser  Ala
          835                      840                845

Phe  Thr  Thr  Ser  Asp  Val  Val  Arg  Met  His  Val  Gly  Asp  Gly  Lys  Val
     850                 855                      860

Pro  Cys  Arg  Ser  Asn  Thr  Phe  Leu  Asn  Ile  Phe  Arg  Arg  Lys  Lys  Ala
865                      870                875                          880

Gly  Ala  Gly  Asn  Ala  Lys  Lys  Arg  Gln  Pro  Glu  Phe  Ser  Pro  Thr  Ser
               885                      890                     895

Gln  Cys  Pro  Ser  Ala  His  Val  Gln  Leu
               900                      905
```

( 2 ) INFORMATION FOR SEQ ID NO:3:

( i ) SEQUENCE CHARACTERISTICS:
        ( A ) LENGTH: 355 base pairs
        ( B ) TYPE: nucleic acid
        ( C ) STRANDEDNESS: both
        ( D ) TOPOLOGY: both ( i i ) MOLECULE TYPE: cDNA ( i x ) FEATURE:
        ( A ) NAME/KEY: CDS
        ( B ) LOCATION: 1..354
        ( D ) OTHER INFORMATION: /product="HUMAN MGLUR2 FRAGMENT"

( x i ) SEQUENCE DESCRIPTION: SEQ ID NO:3:

```
GCC  AAG  CCA  TCC  ACG  GCA  GTG  TGT  ACC  TTA  CGG  CGT  CTT  GGT  TTG  GGC     48
Ala  Lys  Pro  Ser  Thr  Ala  Val  Cys  Thr  Leu  Arg  Arg  Leu  Gly  Leu  Gly
1                        5                        10                      15

ACT  GCC  TTC  TCT  GTC  TGC  TAC  TCA  GCC  CTG  CTC  ACC  AAG  ACC  AAC  CGC     96
Thr  Ala  Phe  Ser  Val  Cys  Tyr  Ser  Ala  Leu  Leu  Thr  Lys  Thr  Asn  Arg
                    20                       25                       30

ATT  GCA  CGC  ATC  TTC  GGT  GGG  GCC  CGG  GAG  GGT  GCC  CAG  CGG  CCA  CGC    144
Ile  Ala  Arg  Ile  Phe  Gly  Gly  Ala  Arg  Glu  Gly  Ala  Gln  Arg  Pro  Arg
               35                       40                       45

TTC  ATC  AGT  CCT  GCC  TCA  CAG  GTG  GCC  ATC  TGC  CTG  GAA  CTT  ATC  TCG    192
Phe  Ile  Ser  Pro  Ala  Ser  Gln  Val  Ala  Ile  Cys  Leu  Glu  Leu  Ile  Ser
          50                       55                       60

GGC  CAG  CTG  CTC  ATC  GTG  GTC  GCC  TGG  CTG  GTG  GTG  GAG  GCA  CCG  GGC    240
Gly  Gln  Leu  Leu  Ile  Val  Val  Ala  Trp  Leu  Val  Val  Glu  Ala  Pro  Gly
65                       70                       75                      80

ACA  GGC  AAG  GAG  ACA  GCC  CCC  GAA  CGG  CGG  GAG  GTG  GTG  ACA  CTG  CGC    288
Thr  Gly  Lys  Glu  Thr  Ala  Pro  Glu  Arg  Arg  Glu  Val  Val  Thr  Leu  Arg
                    85                       90                       95

TGC  AAC  CAC  CGC  GAT  GCA  AGT  ATG  TTG  GGC  TCG  CTG  GCC  TAC  AAT  GTG    336
Cys  Asn  His  Arg  Asp  Ala  Ser  Met  Leu  Gly  Ser  Leu  Ala  Tyr  Asn  Val
               100                     105                      110

CTC  CTC  ATC  GCG  CTC  TGC  A                                                    355
Leu  Leu  Ile  Ala  Leu  Cys
          115
```

( 2 ) INFORMATION FOR SEQ ID NO:4:

( i ) SEQUENCE CHARACTERISTICS:
        ( A ) LENGTH: 118 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Ala  Lys  Pro  Ser  Thr  Ala  Val  Cys  Thr  Leu  Arg  Arg  Leu  Gly  Leu  Gly
1                        5                        10                      15
```

| | | | | | | | | | | | | |
|---|---|---|---|---|---|---|---|---|---|---|---|---|
|Thr|Ala|Phe|Ser|Val|Cys|Tyr|Ser|Ala|Leu|Leu|Thr|Lys|Thr|Asn|Arg|
| | | |20| | | |25| | | |30| | | |
|Ile|Ala|Arg|Ile|Phe|Gly|Gly|Ala|Arg|Glu|Gly|Ala|Gln|Arg|Pro|Arg|
| | |35| | | |40| | | |45| | | | |
|Phe|Ile|Ser|Pro|Ala|Ser|Gln|Val|Ala|Ile|Cys|Leu|Glu|Leu|Ile|Ser|
| |50| | | |55| | | |60| | | | | |
|Gly|Gln|Leu|Leu|Ile|Val|Val|Ala|Trp|Leu|Val|Val|Glu|Ala|Pro|Gly|
|65| | | |70| | | |75| | | |80| | |
|Thr|Gly|Lys|Glu|Thr|Ala|Pro|Glu|Arg|Arg|Glu|Val|Val|Thr|Leu|Arg|
| | | |85| | | |90| | | |95| | | |
|Cys|Asn|His|Arg|Asp|Ala|Ser|Met|Leu|Gly|Ser|Leu|Ala|Tyr|Asn|Val|
| | |100| | | |105| | | |110| | | | |
|Leu|Leu|Ile|Ala|Leu|Cys|
| | |115| | | |

( 2 ) INFORMATION FOR SEQ ID NO:5:

( i ) SEQUENCE CHARACTERISTICS:
        ( A ) LENGTH: 3919 base pairs
        ( B ) TYPE: nucleic acid
        ( C ) STRANDEDNESS: both
        ( D ) TOPOLOGY: both ( i i ) MOLECULE TYPE: cDNA ( i x ) FEATURE:
        ( A ) NAME/KEY: CDS
        ( B ) LOCATION: 1064..3703
        ( D ) OTHER INFORMATION: /product="HUMAN MGLUR3"

( x i ) SEQUENCE DESCRIPTION: SEQ ID NO:5:

```
CGGCCTCCCT GGCTCTCACA CTCCCTCTCT GCTCCCGCTC TCCTAATCTC CTCTGGCATG        60
CGGTCAGCCC CCTGCCCAGG GACCACAGGA GAGTTCTTGT AAGGACTGTT AGTCCCTGCT       120
TACCTGAAAG CCAAGCGCTC TAGCAGAGCT TTAAAGTTGG AGCCGCCACC CTCCCTACCG       180
CCCCATGCCC CTTCACCCCA CTCCGAAATT CACCGACCTT TGCATGCACT GCCTAAGGAT       240
TTCAGAGTGA GGCAAAGCAG TCGGCAAATC TACCCTGGCT TTTCGTATAA AAATCCTCTC       300
GTCTAGGTAC CCTGGCTCAC TGAAGACTCT GCAGATATAC CCTTATAAGA GGGAGGGTGG       360
GGGAGGGAAA AGAACGAGAG AGGGAGGAAA GAATGAAAAG GAGAGGATGC CAGGAGGTCC       420
GTGCTTCTGC CAAGAGTCCC AATTAGATGC GACGGCTTCA GCCTGGTCAA GGTGAAGGAA       480
AGTTGCTTCC GCGCCTAGGA AGTGGGTTTG CCTGATAAGA GAAGGAGGAG GGGACTCGGC       540
TGGGAAGAGC TCCCCTCCCC TCCGCGGAAG ACCACTGGGT CCCCTCTTTC GGCAACCTCC       600
TCCCTCTCTT CTACTCCACC CCTCCGTTTT CCCACTCCCC ACTGACTCGG ATGCCTGGAT       660
GTTCTGCCAC CGGGCAGTGG TCCAGCGTGC AGCCGGGAGG GGGCAGGGGC AGGGGGCACT       720
GTGACAGGAA GCTGCGCGCA CAAGTTGGCC ATTTCGAGGG CAAAATAAGT TCTCCCTTGG       780
ATTTGGAAAG GACAAAGCCA GTAAGCTACC TCTTTTGTGT CGGATGAGGA GGACCAACCA       840
TGAGCCAGAG CCCGGGTGCA GGCTCACCGC CGCCGCTGCC ACCGCGGTCA GCTCCAGTTC       900
CTGCCAGGAG TTGTCGGTGC GAGGAATTTT GTGACAGGCT CTGTTAGTCT GTTCCTCCCT       960
TATTTGAAGG ACAGGCCAAA GATCCAGTTT GGAAATGAGA GAGGACTAGC ATGACACATT      1020
GGCTCCACCA TTGATATCTC CCAGAGGTAC AGAAACAGGA TTC ATG AAG ATG TTG        1075
                                              Met Lys Met Leu
                                                1
ACA AGA CTG CAA GTT CTT ACC TTA GCT TTG TTT TCA AAG GGA TTT TTA       1123
Thr Arg Leu Gln Val Leu Thr Leu Ala Leu Phe Ser Lys Gly Phe Leu
```

| | | | | | | | | | | | | | | | | |
|---|---|---|---|---|---|---|---|---|---|---|---|---|---|---|---|---|
| CTC | TCT | TTA | GGG | GAC | CAT | AAC | TTT | CTA | AGG | AGA | GAG | ATT | AAA | ATA | GAA | 1171 |
| Leu | Ser | Leu | Gly | Asp | His | Asn | Phe | Leu | Arg | Arg | Glu | Ile | Lys | Ile | Glu | |
| | | | | 25 | | | | | 30 | | | | | 35 | | |
| GGT | GAC | CTT | GTT | TTA | GGG | GGC | CTG | TTT | CCT | ATT | AAC | GAA | AAA | GGC | ACT | 1219 |
| Gly | Asp | Leu | Val | Leu | Gly | Gly | Leu | Phe | Pro | Ile | Asn | Glu | Lys | Gly | Thr | |
| | | | 40 | | | | | 45 | | | | | 50 | | | |
| GGA | ACT | GAA | GAA | TGT | GGG | CGA | ATC | AAT | GAA | GAC | CGA | GGG | ATT | CAA | CGC | 1267 |
| Gly | Thr | Glu | Glu | Cys | Gly | Arg | Ile | Asn | Glu | Asp | Arg | Gly | Ile | Gln | Arg | |
| | | 55 | | | | | 60 | | | | | 65 | | | | |
| CTG | GAA | GCC | ATG | TTG | TTT | GCT | ATT | GAT | GAA | ATC | AAC | AAA | GAT | GAT | TAC | 1315 |
| Leu | Glu | Ala | Met | Leu | Phe | Ala | Ile | Asp | Glu | Ile | Asn | Lys | Asp | Asp | Tyr | |
| | 70 | | | | | 75 | | | | | 80 | | | | | |
| TTG | CTA | CCA | GGA | GTG | AAG | TTG | GGT | GTT | CAC | ATT | TTG | GAT | ACA | TGT | TCA | 1363 |
| Leu | Leu | Pro | Gly | Val | Lys | Leu | Gly | Val | His | Ile | Leu | Asp | Thr | Cys | Ser | |
| 85 | | | | 90 | | | | | 95 | | | | | 100 | | |
| AGG | GAT | ACC | TAT | GCA | TTG | GAG | CAA | TCA | CTG | GAG | TTT | GTC | AGG | GCA | TCT | 1411 |
| Arg | Asp | Thr | Tyr | Ala | Leu | Glu | Gln | Ser | Leu | Glu | Phe | Val | Arg | Ala | Ser | |
| | | | | 105 | | | | | 110 | | | | | 115 | | |
| TTG | ACA | AAA | GTG | GAT | GAA | GCT | GAG | TAT | ATG | TGT | CCT | GAT | GGA | TCC | TAT | 1459 |
| Leu | Thr | Lys | Val | Asp | Glu | Ala | Glu | Tyr | Met | Cys | Pro | Asp | Gly | Ser | Tyr | |
| | | | 120 | | | | | 125 | | | | | 130 | | | |
| GCC | ATT | CAA | GAA | AAC | ATC | CCA | CTT | CTC | ATT | GCA | GGG | GTC | ATT | GGT | GGC | 1507 |
| Ala | Ile | Gln | Glu | Asn | Ile | Pro | Leu | Leu | Ile | Ala | Gly | Val | Ile | Gly | Gly | |
| | | 135 | | | | | 140 | | | | | 145 | | | | |
| TCT | TAT | AGC | AGT | GTT | TCC | ATA | CAG | GTG | GCA | AAC | CTG | CTG | CGG | CTC | TTC | 1555 |
| Ser | Tyr | Ser | Ser | Val | Ser | Ile | Gln | Val | Ala | Asn | Leu | Leu | Arg | Leu | Phe | |
| | 150 | | | | | 155 | | | | | 160 | | | | | |
| CAG | ATC | CCT | CAG | ATC | AGC | TAC | GCA | TCC | ACC | AGC | GCC | AAA | CTC | AGT | GAT | 1603 |
| Gln | Ile | Pro | Gln | Ile | Ser | Tyr | Ala | Ser | Thr | Ser | Ala | Lys | Leu | Ser | Asp | |
| 165 | | | | | 170 | | | | | 175 | | | | | 180 | |
| AAG | TCG | CGC | TAT | GAT | TAC | TTT | GCC | AGG | ACC | GTG | CCC | CCC | GAC | TTC | TAC | 1651 |
| Lys | Ser | Arg | Tyr | Asp | Tyr | Phe | Ala | Arg | Thr | Val | Pro | Pro | Asp | Phe | Tyr | |
| | | | | 185 | | | | | 190 | | | | | 195 | | |
| CAG | GCC | AAA | GCC | ATG | GCT | GAG | ATC | TTG | CGC | TTC | TTC | AAC | TGG | ACC | TAC | 1699 |
| Gln | Ala | Lys | Ala | Met | Ala | Glu | Ile | Leu | Arg | Phe | Phe | Asn | Trp | Thr | Tyr | |
| | | | 200 | | | | | 205 | | | | | 210 | | | |
| GTG | TCC | ACA | GTA | GCC | TCC | GAG | GGT | GAT | TAC | GGG | GAG | ACA | GGG | ATC | GAG | 1747 |
| Val | Ser | Thr | Val | Ala | Ser | Glu | Gly | Asp | Tyr | Gly | Glu | Thr | Gly | Ile | Glu | |
| | | 215 | | | | | 220 | | | | | 225 | | | | |
| GCC | TTC | GAG | CAG | GAA | GCC | CGC | CTG | CGC | AAC | ATC | TGC | ATC | GCT | ACG | GCG | 1795 |
| Ala | Phe | Glu | Gln | Glu | Ala | Arg | Leu | Arg | Asn | Ile | Cys | Ile | Ala | Thr | Ala | |
| | 230 | | | | | 235 | | | | | 240 | | | | | |
| GAG | AAG | GTG | GGC | CGC | TCC | AAC | ATC | CGC | AAG | TCC | TAC | GAC | AGC | GTG | ATC | 1843 |
| Glu | Lys | Val | Gly | Arg | Ser | Asn | Ile | Arg | Lys | Ser | Tyr | Asp | Ser | Val | Ile | |
| 245 | | | | | 250 | | | | | 255 | | | | | 260 | |
| CGA | GAA | CTG | TTG | CAG | AAG | CCC | AAC | GCG | CGC | GTC | GTG | GTC | CTC | TTC | ATG | 1891 |
| Arg | Glu | Leu | Leu | Gln | Lys | Pro | Asn | Ala | Arg | Val | Val | Val | Leu | Phe | Met | |
| | | | | 265 | | | | | 270 | | | | | 275 | | |
| CGC | AGC | GAC | GAC | TCG | CGG | GAG | CTC | ATT | GCA | GCC | GCC | AGC | CGC | GCC | AAT | 1939 |
| Arg | Ser | Asp | Asp | Ser | Arg | Glu | Leu | Ile | Ala | Ala | Ala | Ser | Arg | Ala | Asn | |
| | | | 280 | | | | | 285 | | | | | 290 | | | |
| GCC | TCC | TTC | ACC | TGG | GTG | GCC | AGC | GAC | GGT | TGG | GGC | GCG | CAG | GAG | AGC | 1987 |
| Ala | Ser | Phe | Thr | Trp | Val | Ala | Ser | Asp | Gly | Trp | Gly | Ala | Gln | Glu | Ser | |
| | | 295 | | | | | 300 | | | | | 305 | | | | |
| ATC | ATC | AAG | GGC | AGC | GAG | CAT | GTG | GCC | TAC | GGC | GAC | ATC | ACC | CTG | GAG | 2035 |
| Ile | Ile | Lys | Gly | Ser | Glu | His | Val | Ala | Tyr | Gly | Asp | Ile | Thr | Leu | Glu | |
| | | 310 | | | | | 315 | | | | | 320 | | | | |
| CTG | GCC | TCC | CAG | CCT | GTC | CGC | CAG | TTC | GGC | CGC | TAC | TTC | CAG | AGC | CTC | 2083 |
| Leu | Ala | Ser | Gln | Pro | Val | Arg | Gln | Phe | Gly | Arg | Tyr | Phe | Gln | Ser | Leu | |

| | | | | |
|---|---|---|---|---|
| 325 | | 330 | 335 | 340 |

| | | | | | | | | | | | | | | | | |
|---|---|---|---|---|---|---|---|---|---|---|---|---|---|---|---|---|
| AAC | CCC | TAC | AAC | AAC | CAC | CGC | AAC | CCC | TGG | TTC | CGG | GAC | TTC | TGG | GAG | 2131 |
| Asn | Pro | Tyr | Asn | Asn | His | Arg | Asn | Pro | Trp | Phe | Arg | Asp | Phe | Trp | Glu | |
| | | | | 345 | | | | 350 | | | | | 355 | | | |
| CAA | AAG | TTT | CAG | TGC | AGC | CTC | CAG | AAC | AAA | CGC | AAC | CAC | AGG | CGC | GTC | 2179 |
| Gln | Lys | Phe | Gln | Cys | Ser | Leu | Gln | Asn | Lys | Arg | Asn | His | Arg | Arg | Val | |
| | | | 360 | | | | | 365 | | | | | 370 | | | |
| TGC | GAA | AAG | CAC | CTG | GCC | ATC | GAC | AGC | AGC | AAC | TAC | GAG | CAA | GAG | TCC | 2227 |
| Cys | Glu | Lys | His | Leu | Ala | Ile | Asp | Ser | Ser | Asn | Tyr | Glu | Gln | Glu | Ser | |
| | | 375 | | | | | 380 | | | | | 385 | | | | |
| AAG | ATC | ATG | TTT | GTG | GTG | AAC | GCG | GTG | TAT | GCC | ATG | GCC | CAC | GCT | TTG | 2275 |
| Lys | Ile | Met | Phe | Val | Val | Asn | Ala | Val | Tyr | Ala | Met | Ala | His | Ala | Leu | |
| | | 390 | | | | 395 | | | | | 400 | | | | | |
| CAC | AAA | ATG | CAG | CGC | ACC | CTC | TGT | CCC | AAC | ACT | ACC | AAG | CTT | TGT | GAT | 2323 |
| His | Lys | Met | Gln | Arg | Thr | Leu | Cys | Pro | Asn | Thr | Thr | Lys | Leu | Cys | Asp | |
| 405 | | | | | 410 | | | | | 415 | | | | | 420 | |
| GCT | ATG | AAG | ATC | CTG | GAT | GGG | AAG | AAG | TTG | TAC | AAG | GAT | TAC | TTG | CTG | 2371 |
| Ala | Met | Lys | Ile | Leu | Asp | Gly | Lys | Lys | Leu | Tyr | Lys | Asp | Tyr | Leu | Leu | |
| | | | | 425 | | | | | 430 | | | | | 435 | | |
| AAA | ATC | AAC | TTC | ACG | GCT | CCA | TTC | AAC | CCA | AAT | AAA | GAT | GCA | GAT | AGC | 2419 |
| Lys | Ile | Asn | Phe | Thr | Ala | Pro | Phe | Asn | Pro | Asn | Lys | Asp | Ala | Asp | Ser | |
| | | | | 440 | | | | | 445 | | | | | 450 | | |
| ATA | GTC | AAG | TTT | GAC | ACT | TTT | GGA | GAT | GGA | ATG | GGG | CGA | TAC | AAC | GTG | 2467 |
| Ile | Val | Lys | Phe | Asp | Thr | Phe | Gly | Asp | Gly | Met | Gly | Arg | Tyr | Asn | Val | |
| | | 455 | | | | | 460 | | | | | 465 | | | | |
| TTC | AAT | TTC | CAA | AAT | GTA | GGT | GGG | AAG | TAT | TCC | TAC | TTG | AAA | GTT | GGT | 2515 |
| Phe | Asn | Phe | Gln | Asn | Val | Gly | Gly | Lys | Tyr | Ser | Tyr | Leu | Lys | Val | Gly | |
| | | 470 | | | | 475 | | | | | 480 | | | | | |
| CAC | TGG | GCA | GAA | ACC | TTA | TCG | CTA | GAT | GTC | AAC | TCT | ATC | CAC | TGG | TCC | 2563 |
| His | Trp | Ala | Glu | Thr | Leu | Ser | Leu | Asp | Val | Asn | Ser | Ile | His | Trp | Ser | |
| 485 | | | | | 490 | | | | | 495 | | | | | 500 | |
| CGG | AAC | TCA | GTC | CCC | ACT | TCC | CAG | TGC | AGC | GAC | CCC | TGT | GCC | CCC | AAT | 2611 |
| Arg | Asn | Ser | Val | Pro | Thr | Ser | Gln | Cys | Ser | Asp | Pro | Cys | Ala | Pro | Asn | |
| | | | | 505 | | | | | 510 | | | | | 515 | | |
| GAA | ATG | AAG | AAT | ATG | CAA | CCA | GGG | GAT | GTC | TGC | TGC | TGG | ATT | TGC | ATC | 2659 |
| Glu | Met | Lys | Asn | Met | Gln | Pro | Gly | Asp | Val | Cys | Cys | Trp | Ile | Cys | Ile | |
| | | | | 520 | | | | | 525 | | | | | 530 | | |
| CCC | TGT | GAA | CCC | TAC | GAA | TAC | CTG | GCT | GAT | GAG | TTT | ACC | TGT | ATG | GAT | 2707 |
| Pro | Cys | Glu | Pro | Tyr | Glu | Tyr | Leu | Ala | Asp | Glu | Phe | Thr | Cys | Met | Asp | |
| | | 535 | | | | | 540 | | | | | 545 | | | | |
| TGT | GGG | TCT | GGA | CAG | TGG | CCC | ACT | GCA | GAC | CTA | ACT | GGA | TGC | TAT | GAC | 2755 |
| Cys | Gly | Ser | Gly | Gln | Trp | Pro | Thr | Ala | Asp | Leu | Thr | Gly | Cys | Tyr | Asp | |
| | 550 | | | | | 555 | | | | | 560 | | | | | |
| CTT | CCT | GAG | GAC | TAC | ATC | AGG | TGG | GAA | GAC | GCC | TGG | GCC | ATT | GGC | CCA | 2803 |
| Leu | Pro | Glu | Asp | Tyr | Ile | Arg | Trp | Glu | Asp | Ala | Trp | Ala | Ile | Gly | Pro | |
| 565 | | | | | 570 | | | | | 575 | | | | | 580 | |
| GTC | ACC | ATT | GCC | TGT | CTG | GGT | TTT | ATG | TGT | ACA | TGC | ATG | GTT | GTA | ACT | 2851 |
| Val | Thr | Ile | Ala | Cys | Leu | Gly | Phe | Met | Cys | Thr | Cys | Met | Val | Val | Thr | |
| | | | | 585 | | | | | 590 | | | | | 595 | | |
| GTT | TTT | ATC | AAG | CAC | AAC | AAC | ACA | CCC | TTG | GTC | AAA | GCA | TCG | GGC | CGA | 2899 |
| Val | Phe | Ile | Lys | His | Asn | Asn | Thr | Pro | Leu | Val | Lys | Ala | Ser | Gly | Arg | |
| | | | 600 | | | | | 605 | | | | | 610 | | | |
| GAA | CTC | TGC | TAC | ATC | TTA | TTG | TTT | GGG | GTT | GGC | CTG | TCA | TAC | TGC | ATG | 2947 |
| Glu | Leu | Cys | Tyr | Ile | Leu | Leu | Phe | Gly | Val | Gly | Leu | Ser | Tyr | Cys | Met | |
| | | 615 | | | | | 620 | | | | | 625 | | | | |
| ACA | TTC | TTC | TTC | ATT | GCC | AAG | CCA | TCA | CCA | GTC | ATC | TGT | GCA | TTG | CGC | 2995 |
| Thr | Phe | Phe | Phe | Ile | Ala | Lys | Pro | Ser | Pro | Val | Ile | Cys | Ala | Leu | Arg | |
| | | | | 630 | | | | | 635 | | | | | 640 | | |
| CGA | CTC | GGG | CTG | GGG | AGT | TCC | TTC | GCT | ATC | TGT | TAC | TCA | GCC | CTG | CTG | 3043 |
| Arg | Leu | Gly | Leu | Gly | Ser | Ser | Phe | Ala | Ile | Cys | Tyr | Ser | Ala | Leu | Leu | |

| | | | | | | | | | | | | | | | | |
|---|---|---|---|---|---|---|---|---|---|---|---|---|---|---|---|---|
|645| | | | | |650| | | | |655| | | | |660|

| ACC | AAG | ACA | AAC | TGC | ATT | GCC | CGC | ATC | TTC | GAT | GGG | GTC | AAG | AAT | GGC | 3091 |
|---|---|---|---|---|---|---|---|---|---|---|---|---|---|---|---|---|
| Thr | Lys | Thr | Asn | Cys<br>665 | Ile | Ala | Arg | Ile | Phe<br>670 | Asp | Gly | Val | Lys | Asn<br>675 | Gly | |
| GCT | CAG | AGG | CCA | AAA | TTC | ATC | AGC | CCC | AGT | TCT | CAG | GTT | TTC | ATC | TGC | 3139 |
| Ala | Gln | Arg | Pro<br>680 | Lys | Phe | Ile | Ser | Pro<br>685 | Ser | Ser | Gln | Val | Phe<br>690 | Ile | Cys | |
| CTG | GGT | CTG | ATC | CTG | GTG | CAA | ATT | GTG | ATG | GTG | TCT | GTG | TGG | CTC | ATC | 3187 |
| Leu | Gly | Leu<br>695 | Ile | Leu | Val | Gln | Ile<br>700 | Val | Met | Val | Ser | Val<br>705 | Trp | Leu | Ile | |
| CTG | GAG | GCC | CCA | GGC | ACC | AGG | AGG | TAT | ACC | CTT | GCA | GAG | AAG | CGG | GAA | 3235 |
| Leu | Glu<br>710 | Ala | Pro | Gly | Thr | Arg<br>715 | Arg | Tyr | Thr | Leu | Ala<br>720 | Glu | Lys | Arg | Glu | |
| ACA | GTC | ATC | CTA | AAA | TGC | AAT | GTC | AAA | GAT | TCC | AGC | ATG | TTG | ATC | TCT | 3283 |
| Thr<br>725 | Val | Ile | Leu | Lys | Cys<br>730 | Asn | Val | Lys | Asp | Ser<br>735 | Ser | Met | Leu | Ile | Ser<br>740 | |
| CTT | ACC | TAC | GAT | GTG | ATC | CTG | GTG | ATC | TTA | TGC | ACT | GTG | TAC | GCC | TTC | 3331 |
| Leu | Thr | Tyr | Asp | Val<br>745 | Ile | Leu | Val | Ile | Leu<br>750 | Cys | Thr | Val | Tyr | Ala<br>755 | Phe | |
| AAA | ACG | CGG | AAG | TGC | CCA | GAA | AAT | TTC | AAC | GAA | GCT | AAG | TTC | ATA | GGT | 3379 |
| Lys | Thr | Arg | Lys<br>760 | Cys | Pro | Glu | Asn | Phe<br>765 | Asn | Glu | Ala | Lys | Phe<br>770 | Ile | Gly | |
| TTT | ACC | ATG | TAC | ACC | ACG | TGC | ATC | ATC | TGG | TTG | GCC | TTC | CTC | CCT | ATA | 3427 |
| Phe | Thr | Met<br>775 | Tyr | Thr | Thr | Cys | Ile<br>780 | Ile | Trp | Leu | Ala | Phe<br>785 | Leu | Pro | Ile | |
| TTT | TAT | GTG | ACA | TCA | AGT | GAC | TAC | AGA | GTG | CAG | ACG | ACA | ACC | ATG | TGC | 3475 |
| Phe | Tyr<br>790 | Val | Thr | Ser | Ser | Asp | Tyr | Arg<br>795 | Val | Gln | Thr | Thr<br>800 | Thr | Met | Cys | |
| ATC | TCT | GTC | AGC | CTG | AGT | GGC | TTT | GTG | GTC | TTG | GGC | TGT | TTG | TTT | GCA | 3523 |
| Ile | Ser | Val | Ser | Leu<br>810 | Ser | Gly | Phe | Val | Val<br>815 | Leu | Gly | Cys | Leu | Phe<br>820 | Ala | |
| | | | | | | | | | | | | | | | | |
| Ile<br>805 | | | | | | | | | | | | | | | | |
| CCC | AAG | GTT | CAC | ATC | ATC | CTG | TTT | CAA | CCC | CAG | AAG | AAT | GTT | GTC | ACA | 3571 |
| Pro | Lys | Val | His | Ile<br>825 | Ile | Leu | Phe | Gln | Pro<br>830 | Gln | Lys | Asn | Val | Val<br>835 | Thr | |
| CAC | AGA | CTG | CAC | CTC | AAC | AGG | TTC | AGT | GTC | AGT | GGA | ACT | GGG | ACC | ACA | 3619 |
| His | Arg | Leu | His<br>840 | Leu | Asn | Arg | Phe | Ser<br>845 | Val | Ser | Gly | Thr | Gly<br>850 | Thr | Thr | |
| TAC | TCT | CAG | TCC | TCT | GCA | AGC | ACG | TAT | GTG | CCA | ACG | GTG | TGC | AAT | GGG | 3667 |
| Tyr | Ser | Gln<br>855 | Ser | Ser | Ala | Ser | Thr<br>860 | Tyr | Val | Pro | Thr | Val<br>865 | Cys | Asn | Gly | |
| CGG | GAA | GTC | CTC | GAC | TCC | ACC | ACC | TCA | TCT | CTG | | | | | | 3720 |
| Arg | Glu<br>870 | Val | Leu | Asp | Ser<br>875 | Thr | Thr | Ser | Ser | Leu<br>880 | | | | | | | followed by: TGATTGTGAA TTGCAGTTCA

| GTTCTTGTGT | TTTTAGACTG | TTAGACAAAA | GTGCTCACGT | GCAGCTCCAG | AAATATGGAAA | 3780 |
|---|---|---|---|---|---|---|
| CAGAGCAAAA | GAACAACCCT | AGTACCTTTT | TTTAGAAACA | GTACGATAAA | TTATTTTTGA | 3840 |
| GGACTGTATA | TAGTGATGTG | CTAGAACTTT | CTAGGCTGAG | TCTAGTGCCC | CTATTATTAA | 3900 |
| CAGTCCGAGT | GTACGTACC | | | | | 3919 |

( 2 ) INFORMATION FOR SEQ ID NO:6:

( i ) SEQUENCE CHARACTERISTICS:
        ( A ) LENGTH: 879 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

| Met | Lys | Met | Leu | Thr | Arg | Leu | Gln | Val | Leu | Thr | Leu | Ala | Leu | Phe | Ser |
|---|---|---|---|---|---|---|---|---|---|---|---|---|---|---|---|
| 1 | | | | 5 | | | | | 10 | | | | | 15 | |

-continued

| | | | | | | | | | | | | |
|---|---|---|---|---|---|---|---|---|---|---|---|---|
| Lys | Gly | Phe | Leu | Leu | Ser | Leu | Gly | Asp | His | Asn | Phe | Leu | Arg | Arg | Glu |
| | | | 20 | | | | 25 | | | | 30 | |
| Ile | Lys | Ile | Glu | Gly | Asp | Leu | Val | Leu | Gly | Gly | Leu | Phe | Pro | Ile | Asn |
| | | 35 | | | | 40 | | | | 45 | |
| Glu | Lys | Gly | Thr | Gly | Thr | Glu | Glu | Cys | Gly | Arg | Ile | Asn | Glu | Asp | Arg |
| 50 | | | | 55 | | | | 60 | |
| Gly | Ile | Gln | Arg | Leu | Glu | Ala | Met | Leu | Phe | Ala | Ile | Asp | Glu | Ile | Asn |
| 65 | | | | 70 | | | | 75 | | | | 80 |
| Lys | Asp | Asp | Tyr | Leu | Leu | Pro | Gly | Val | Lys | Leu | Gly | Val | His | Ile | Leu |
| | | | 85 | | | | 90 | | | | 95 |
| Asp | Thr | Cys | Ser | Arg | Asp | Thr | Tyr | Ala | Leu | Glu | Gln | Ser | Leu | Glu | Phe |
| | | | 100 | | | | 105 | | | | 110 |
| Val | Arg | Ala | Ser | Leu | Thr | Lys | Val | Asp | Glu | Ala | Glu | Tyr | Met | Cys | Pro |
| | | 115 | | | | 120 | | | | 125 | |
| Asp | Gly | Ser | Tyr | Ala | Ile | Gln | Glu | Asn | Ile | Pro | Leu | Leu | Ile | Ala | Gly |
| | 130 | | | | 135 | | | | 140 | |
| Val | Ile | Gly | Gly | Ser | Tyr | Ser | Ser | Val | Ser | Ile | Gln | Val | Ala | Asn | Leu |
| 145 | | | | 150 | | | | 155 | | | | 160 |
| Leu | Arg | Leu | Phe | Gln | Ile | Pro | Gln | Ile | Ser | Tyr | Ala | Ser | Thr | Ser | Ala |
| | | | 165 | | | | 170 | | | | 175 |
| Lys | Leu | Ser | Asp | Lys | Ser | Arg | Tyr | Asp | Tyr | Phe | Ala | Arg | Thr | Val | Pro |
| | | 180 | | | | 185 | | | | 190 | |
| Pro | Asp | Phe | Tyr | Gln | Ala | Lys | Ala | Met | Ala | Glu | Ile | Leu | Arg | Phe | Phe |
| | | 195 | | | | 200 | | | | 205 | |
| Asn | Trp | Thr | Tyr | Val | Ser | Thr | Val | Ala | Ser | Glu | Gly | Asp | Tyr | Gly | Glu |
| | 210 | | | | 215 | | | | 220 | |
| Thr | Gly | Ile | Glu | Ala | Phe | Glu | Gln | Glu | Ala | Arg | Leu | Arg | Asn | Ile | Cys |
| 225 | | | | 230 | | | | 235 | | | | 240 |
| Ile | Ala | Thr | Ala | Glu | Lys | Val | Gly | Arg | Ser | Asn | Ile | Arg | Lys | Ser | Tyr |
| | | | 245 | | | | 250 | | | | 255 |
| Asp | Ser | Val | Ile | Arg | Glu | Leu | Leu | Gln | Lys | Pro | Asn | Ala | Arg | Val | Val |
| | | | 260 | | | | 265 | | | | 270 |
| Val | Leu | Phe | Met | Arg | Ser | Asp | Asp | Ser | Arg | Glu | Leu | Ile | Ala | Ala | Ala |
| | | 275 | | | | 280 | | | | 285 | |
| Ser | Arg | Ala | Asn | Ala | Ser | Phe | Thr | Trp | Val | Ala | Ser | Asp | Gly | Trp | Gly |
| | 290 | | | | 295 | | | | 300 | |
| Ala | Gln | Glu | Ser | Ile | Ile | Lys | Gly | Ser | Glu | His | Val | Ala | Tyr | Gly | Asp |
| 305 | | | | 310 | | | | 315 | | | | 320 |
| Ile | Thr | Leu | Glu | Leu | Ala | Ser | Gln | Pro | Val | Arg | Gln | Phe | Gly | Arg | Tyr |
| | | | 325 | | | | 330 | | | | 335 |
| Phe | Gln | Ser | Leu | Asn | Pro | Tyr | Asn | Asn | His | Arg | Asn | Pro | Trp | Phe | Arg |
| | | | 340 | | | | 345 | | | | 350 |
| Asp | Phe | Trp | Glu | Gln | Lys | Phe | Gln | Cys | Ser | Leu | Gln | Asn | Lys | Arg | Asn |
| | | 355 | | | | 360 | | | | 365 | |
| His | Arg | Arg | Val | Cys | Glu | Lys | His | Leu | Ala | Ile | Asp | Ser | Ser | Asn | Tyr |
| | 370 | | | | 375 | | | | 380 | |
| Glu | Gln | Glu | Ser | Lys | Ile | Met | Phe | Val | Val | Asn | Ala | Val | Tyr | Ala | Met |
| 385 | | | | 390 | | | | 395 | | | | 400 |
| Ala | His | Ala | Leu | His | Lys | Met | Gln | Arg | Thr | Leu | Cys | Pro | Asn | Thr | Thr |
| | | | 405 | | | | 410 | | | | 415 |
| Lys | Leu | Cys | Asp | Ala | Met | Lys | Ile | Leu | Asp | Gly | Lys | Lys | Leu | Tyr | Lys |
| | | | 420 | | | | 425 | | | | 430 |
| Asp | Tyr | Leu | Leu | Lys | Ile | Asn | Phe | Thr | Ala | Pro | Phe | Asn | Pro | Asn | Lys |

-continued

|   |   |   | 435 |   |   |   |   | 440 |   |   |   |   | 445 |   |   |
|---|---|---|---|---|---|---|---|---|---|---|---|---|---|---|---|

Asp Ala Asp Ser Ile Val Lys Phe Asp Thr Phe Gly Asp Gly Met Gly
    450             455             460

Arg Tyr Asn Val Phe Phe Gln Asn Val Gly Gly Lys Tyr Ser Tyr
465             470             475             480

Leu Lys Val Gly His Trp Ala Glu Thr Leu Ser Leu Asp Val Asn Ser
            485             490             495

Ile His Trp Ser Arg Asn Ser Val Pro Thr Ser Gln Cys Ser Asp Pro
        500             505             510

Cys Ala Pro Asn Glu Met Lys Asn Met Gln Pro Gly Asp Val Cys Cys
        515             520             525

Trp Ile Cys Ile Pro Cys Glu Pro Tyr Glu Tyr Leu Ala Asp Glu Phe
    530             535             540

Thr Cys Met Asp Cys Gly Ser Gly Gln Trp Pro Thr Ala Asp Leu Thr
545             550             555             560

Gly Cys Tyr Asp Leu Pro Glu Asp Tyr Ile Arg Trp Glu Asp Ala Trp
            565             570             575

Ala Ile Gly Pro Val Thr Ile Ala Cys Leu Gly Phe Met Cys Thr Cys
        580             585             590

Met Val Val Thr Val Phe Ile Lys His Asn Asn Thr Pro Leu Val Lys
        595             600             605

Ala Ser Gly Arg Glu Leu Cys Tyr Ile Leu Leu Phe Gly Val Gly Leu
    610             615             620

Ser Tyr Cys Met Thr Phe Phe Phe Ile Ala Lys Pro Ser Pro Val Ile
625             630             635             640

Cys Ala Leu Arg Arg Leu Gly Leu Gly Ser Ser Phe Ala Ile Cys Tyr
            645             650             655

Ser Ala Leu Leu Thr Lys Thr Asn Cys Ile Ala Arg Ile Phe Asp Gly
        660             665             670

Val Lys Asn Gly Ala Gln Arg Pro Lys Phe Ile Ser Pro Ser Ser Gln
        675             680             685

Val Phe Ile Cys Leu Gly Leu Ile Leu Val Gln Ile Val Met Val Ser
    690             695             700

Val Trp Leu Ile Leu Glu Ala Pro Gly Thr Arg Arg Tyr Thr Leu Ala
705             710             715             720

Glu Lys Arg Glu Thr Val Ile Leu Lys Cys Asn Val Lys Asp Ser Ser
            725             730             735

Met Leu Ile Ser Leu Thr Tyr Asp Val Ile Leu Val Ile Leu Cys Thr
        740             745             750

Val Tyr Ala Phe Lys Thr Arg Lys Cys Pro Glu Asn Phe Asn Glu Ala
        755             760             765

Lys Phe Ile Gly Phe Thr Met Tyr Thr Thr Cys Ile Ile Trp Leu Ala
    770             775             780

Phe Leu Pro Ile Phe Tyr Val Thr Ser Ser Asp Tyr Arg Val Gln Thr
785             790             795             800

Thr Thr Met Cys Ile Ser Val Ser Leu Ser Gly Phe Val Val Leu Gly
            805             810             815

Cys Leu Phe Ala Pro Lys Val His Ile Ile Leu Phe Gln Pro Gln Lys
        820             825             830

Asn Val Val Thr His Arg Leu His Leu Asn Arg Phe Ser Val Ser Gly
        835             840             845

Thr Gly Thr Thr Tyr Ser Gln Ser Ser Ala Ser Thr Tyr Val Pro Thr
850             855             860

| Val | Cys | Asn | Gly | Arg | Glu | Val | Leu | Asp | Ser | Thr | Thr | Ser | Ser | Leu |
| 865 | | | | | 870 | | | | | 875 | | | | |

( 2 ) INFORMATION FOR SEQ ID NO:7:

( i ) SEQUENCE CHARACTERISTICS:
        ( A ) LENGTH: 4085 base pairs
        ( B ) TYPE: nucleic acid
        ( C ) STRANDEDNESS: both
        ( D ) TOPOLOGY: both ( i i ) MOLECULE TYPE: cDNA ( i x ) FEATURE:
        ( A ) NAME/KEY: CDS
        ( B ) LOCATION: 370..3912
        ( D ) OTHER INFORMATION: /product="HUMAN MGLUR5A"

( x i ) SEQUENCE DESCRIPTION: SEQ ID NO:7:

```
CAGCTCGGCT GTTCTGCGCA CGCTGAGCGG AGGGAATGAG CTTGAGATCA TCTTGGGGGG      60

GAAGCCGGGG ACTGGAGAGG CCGGCTCTGC CCTGCTGATC CCCGTGGCCC AACTTTTCGG     120

GGGGCTAGCT AGACCGAGTC TCACTGCTCG CAGCGCAGCC AACAGGGGGG TTTAGAAGAT     180

CATGACCACA TGGATCATCT AACTAAATGG TACATGGGGA CAAAATGGTC CTTTAGAAAA     240

TACATCTGAA TTGCTGGCTA ATTTCTTGAT TTGCGACTCA ACGTAGGACA TCGCTTGTTC     300

GTAGCTATCA GAACCCTCCT GAATTTTCCC CACCATGCTA TCTTTATTGG CTTGAACTCC     360
```

| TTTCCTAAA | ATG | GTC | CTT | CTG | TTG | ATC | CTG | TCA | GTC | TTA | CTT | TGG | AAA | 408 |
| | Met | Val | Leu | Leu | Leu | Ile | Leu | Ser | Val | Leu | Leu | Trp | Lys | |
| | 1 | | | | 5 | | | | | 10 | | | | |

| GAA | GAT | GTC | CGT | GGG | AGT | GCA | CAG | TCC | AGT | GAG | AGG | AGG | GTG | GTG | GCT | 456 |
| Glu | Asp | Val | Arg | Gly | Ser | Ala | Gln | Ser | Ser | Glu | Arg | Arg | Val | Val | Ala | |
| | 15 | | | | | 20 | | | | | 25 | | | | | |

| CAC | ATG | CCG | GGT | GAC | ATC | ATT | ATT | GGA | GCT | CTC | TTT | TCT | GTT | CAT | CAC | 504 |
| His | Met | Pro | Gly | Asp | Ile | Ile | Ile | Gly | Ala | Leu | Phe | Ser | Val | His | His | |
| 30 | | | | | 35 | | | | | 40 | | | | | 45 | |

| CAG | CCT | ACT | GTG | GAC | AAA | GTT | CAT | GAG | AGG | AAG | TGT | GGG | GCG | GTC | CGT | 552 |
| Gln | Pro | Thr | Val | Asp | Lys | Val | His | Glu | Arg | Lys | Cys | Gly | Ala | Val | Arg | |
| | | | 50 | | | | | 55 | | | | | 60 | | | |

| GAA | CAG | TAT | GGC | ATT | CAG | AGA | GTG | GAG | GCC | ATG | CTG | CAT | ACC | CTG | GAA | 600 |
| Glu | Gln | Tyr | Gly | Ile | Gln | Arg | Val | Glu | Ala | Met | Leu | His | Thr | Leu | Glu | |
| | | 65 | | | | | 70 | | | | | 75 | | | | |

| AGG | ATC | AAT | TCA | GAC | CCC | ACA | CTC | TTG | CCC | AAC | ATC | ACA | CTG | GGC | TGT | 648 |
| Arg | Ile | Asn | Ser | Asp | Pro | Thr | Leu | Leu | Pro | Asn | Ile | Thr | Leu | Gly | Cys | |
| | | 80 | | | | | 85 | | | | | 90 | | | | |

| GAG | ATA | AGG | GAC | TCC | TGC | TGG | CAT | TCG | GCT | GTG | GCC | CTA | GAG | CAG | AGC | 696 |
| Glu | Ile | Arg | Asp | Ser | Cys | Trp | His | Ser | Ala | Val | Ala | Leu | Glu | Gln | Ser | |
| | 95 | | | | | 100 | | | | | 105 | | | | | |

| ATT | GAG | TTC | ATA | AGA | GAT | TCC | CTC | ATT | TCT | TCA | GAA | GAG | GAA | GAA | GGC | 744 |
| Ile | Glu | Phe | Ile | Arg | Asp | Ser | Leu | Ile | Ser | Ser | Glu | Glu | Glu | Glu | Gly | |
| 110 | | | | | 115 | | | | | 120 | | | | | 125 | |

| TTG | GTA | CGC | TGT | GTG | GAT | GGC | TCC | TCC | TCT | TCC | TTC | CGC | TCC | AAG | AAG | 792 |
| Leu | Val | Arg | Cys | Val | Asp | Gly | Ser | Ser | Ser | Ser | Phe | Arg | Ser | Lys | Lys | |
| | | | 130 | | | | | 135 | | | | | 140 | | | |

| CCC | ATA | GTA | GGG | GTC | ATT | GGG | CCT | GGC | TCC | AGT | TCT | GTA | GCC | ATT | CAG | 840 |
| Pro | Ile | Val | Gly | Val | Ile | Gly | Pro | Gly | Ser | Ser | Ser | Val | Ala | Ile | Gln | |
| | | 145 | | | | | 150 | | | | | 155 | | | | |

| GTC | CAG | AAT | TTG | CTC | CAG | CTT | TTC | AAC | ATA | CCT | CAG | ATT | GCT | TAC | TCA | 888 |
| Val | Gln | Asn | Leu | Leu | Gln | Leu | Phe | Asn | Ile | Pro | Gln | Ile | Ala | Tyr | Ser | |
| | | 160 | | | | | 165 | | | | | 170 | | | | |

| GCA | ACC | AGC | ATG | GAT | CTG | AGT | GAC | AAG | ACT | CTG | TTC | AAA | TAT | TTC | ATG | 936 |
| Ala | Thr | Ser | Met | Asp | Leu | Ser | Asp | Lys | Thr | Leu | Phe | Lys | Tyr | Phe | Met | |
| | 175 | | | | | 180 | | | | | 185 | | | | | |

| | | | | | | | | | | | | | | | | |
|---|---|---|---|---|---|---|---|---|---|---|---|---|---|---|---|---|
| AGG | GTT | GTG | CCT | TCA | GAT | GCT | CAG | CAG | GCA | AGG | GCC | ATG | GTG | GAC | ATA | 984 |
| Arg | Val | Val | Pro | Ser | Asp | Ala | Gln | Gln | Ala | Arg | Ala | Met | Val | Asp | Ile | |
| 190 | | | | 195 | | | | | 200 | | | | | 205 | | |
| GTG | AAG | AGG | TAC | AAC | TGG | ACC | TAT | GTA | TCA | GCC | GTG | CAC | ACA | GAA | GGC | 1032 |
| Val | Lys | Arg | Tyr | Asn | Trp | Thr | Tyr | Val | Ser | Ala | Val | His | Thr | Glu | Gly | |
| | | | | 210 | | | | | 215 | | | | | 220 | | |
| AAC | TAT | GGA | GAA | AGT | GGG | ATG | GAA | GCC | TCC | AAA | GAT | ATG | TCA | GCG | AAG | 1080 |
| Asn | Tyr | Gly | Glu | Ser | Gly | Met | Glu | Ala | Ser | Lys | Asp | Met | Ser | Ala | Lys | |
| | | | | 225 | | | | | 230 | | | | | 235 | | |
| GAA | GGG | ATT | TGC | ATC | GCC | CAC | TCT | TAC | AAA | ATC | TAC | AGT | AAT | GCA | GGG | 1128 |
| Glu | Gly | Ile | Cys | Ile | Ala | His | Ser | Tyr | Lys | Ile | Tyr | Ser | Asn | Ala | Gly | |
| | | | 240 | | | | | 245 | | | | | 250 | | | |
| GAG | CAG | AGC | TTT | GAT | AAG | CTG | CTG | AAG | AAG | CTC | ACA | AGT | CAC | TTG | CCC | 1176 |
| Glu | Gln | Ser | Phe | Asp | Lys | Leu | Leu | Lys | Lys | Leu | Thr | Ser | His | Leu | Pro | |
| 255 | | | | | 260 | | | | | 265 | | | | | | |
| AAG | GCC | CGG | GTG | GTG | GCC | TGC | TTC | TGT | GAG | GGC | ATG | ACG | GTG | AGA | GGT | 1224 |
| Lys | Ala | Arg | Val | Val | Ala | Cys | Phe | Cys | Glu | Gly | Met | Thr | Val | Arg | Gly | |
| 270 | | | | | 275 | | | | | 280 | | | | | 285 | |
| CTG | CTG | ATG | GCC | ATG | AGG | CGC | CTG | GGT | CTA | GCG | GGA | GAA | TTT | CTG | CTT | 1272 |
| Leu | Leu | Met | Ala | Met | Arg | Arg | Leu | Gly | Leu | Ala | Gly | Glu | Phe | Leu | Leu | |
| | | | | 290 | | | | | 295 | | | | | 300 | | |
| CTG | GGC | AGT | GAT | GGC | TGG | GCT | GAC | AGG | TAT | GAT | GTG | ACA | GAT | GGA | TAT | 1320 |
| Leu | Gly | Ser | Asp | Gly | Trp | Ala | Asp | Arg | Tyr | Asp | Val | Thr | Asp | Gly | Tyr | |
| | | | 305 | | | | | 310 | | | | | 315 | | | |
| CAG | CGA | GAA | GCT | GTT | GGT | GGC | ATC | ACA | ATC | AAG | CTC | CAA | TCT | CCC | GAT | 1368 |
| Gln | Arg | Glu | Ala | Val | Gly | Gly | Ile | Thr | Ile | Lys | Leu | Gln | Ser | Pro | Asp | |
| | | 320 | | | | | 325 | | | | | 330 | | | | |
| GTC | AAG | TGG | TTT | GAT | GAT | TAT | TAT | CTG | AAG | CTC | CGG | CCA | GAA | ACA | AAC | 1416 |
| Val | Lys | Trp | Phe | Asp | Asp | Tyr | Tyr | Leu | Lys | Leu | Arg | Pro | Glu | Thr | Asn | |
| | 335 | | | | | 340 | | | | | 345 | | | | | |
| CAC | CGA | AAC | CCT | TGG | TTT | CAA | GAA | TTT | TGG | CAG | CAT | CGT | TTT | CAG | TGC | 1464 |
| His | Arg | Asn | Pro | Trp | Phe | Gln | Glu | Phe | Trp | Gln | His | Arg | Phe | Gln | Cys | |
| 350 | | | | | 355 | | | | | 360 | | | | | 365 | |
| CGA | CTG | GAA | GCG | TTT | CCA | CAG | GAG | AAC | AGC | AAA | TAC | AAC | AAG | ACT | TGC | 1512 |
| Arg | Leu | Glu | Ala | Phe | Pro | Gln | Glu | Asn | Ser | Lys | Tyr | Asn | Lys | Thr | Cys | |
| | | | | 370 | | | | | 375 | | | | | 380 | | |
| AAT | AGT | TCT | CTG | ACT | CTG | AAA | ACA | CAT | CAT | GTT | CAG | GAT | TCC | AAA | ATG | 1560 |
| Asn | Ser | Ser | Leu | Thr | Leu | Lys | Thr | His | His | Val | Gln | Asp | Ser | Lys | Met | |
| | | | 385 | | | | | 390 | | | | | 395 | | | |
| GGA | TTT | GTG | ATC | AAC | GCC | ATC | TAT | TCG | ATG | GCC | TAT | GGG | CTC | CAC | AAC | 1608 |
| Gly | Phe | Val | Ile | Asn | Ala | Ile | Tyr | Ser | Met | Ala | Tyr | Gly | Leu | His | Asn | |
| | | | 400 | | | | | 405 | | | | | 410 | | | |
| ATG | CAG | ATG | TCC | CTC | TGC | CCA | GGC | TAT | GCA | GGA | CTC | TGT | GAT | GCC | ATG | 1656 |
| Met | Gln | Met | Ser | Leu | Cys | Pro | Gly | Tyr | Ala | Gly | Leu | Cys | Asp | Ala | Met | |
| | | | 415 | | | | | 420 | | | | | 425 | | | |
| AAG | CCA | ATT | GAT | GGA | CGG | AAA | CTT | TTG | GAG | TCC | CTG | ATG | AAA | ACC | AAT | 1704 |
| Lys | Pro | Ile | Asp | Gly | Arg | Lys | Leu | Leu | Glu | Ser | Leu | Met | Lys | Thr | Asn | |
| 430 | | | | | 435 | | | | | 440 | | | | | 445 | |
| TTT | ACT | GGG | GTT | TCT | GGA | GAT | ACG | ATC | CTA | TTC | GAT | GAG | AAT | GGA | GAC | 1752 |
| Phe | Thr | Gly | Val | Ser | Gly | Asp | Thr | Ile | Leu | Phe | Asp | Glu | Asn | Gly | Asp | |
| | | | | 450 | | | | | 455 | | | | | 460 | | |
| TCT | CCA | GGA | AGG | TAT | GAA | ATA | ATG | AAT | TTC | AAG | GAA | ATG | GGA | AAA | GAT | 1800 |
| Ser | Pro | Gly | Arg | Tyr | Glu | Ile | Met | Asn | Phe | Lys | Glu | Met | Gly | Lys | Asp | |
| | | | 465 | | | | | 470 | | | | | 475 | | | |
| TAC | TTT | GAT | TAT | ATC | AAC | GTT | GGA | AGT | TGG | GAC | AAT | GGA | GAA | TTA | AAA | 1848 |
| Tyr | Phe | Asp | Tyr | Ile | Asn | Val | Gly | Ser | Trp | Asp | Asn | Gly | Glu | Leu | Lys | |
| | | | 480 | | | | | 485 | | | | | 490 | | | |
| ATG | GAT | GAT | GAT | GAA | GTA | TGG | TCC | AAG | AAA | AGC | AAC | ATC | ATC | AGA | TCT | 1896 |
| Met | Asp | Asp | Asp | Glu | Val | Trp | Ser | Lys | Lys | Ser | Asn | Ile | Ile | Arg | Ser | |
| | | | 495 | | | | | 500 | | | | | 505 | | | |

| | | | | | | | | | | | | | | | | |
|---|---|---|---|---|---|---|---|---|---|---|---|---|---|---|---|---|
| GTG | TGC | AGT | GAA | CCA | TGT | GAG | AAA | GGC | CAG | ATC | AAG | GTG | ATC | CGA | AAG | 1944 |
| Val | Cys | Ser | Glu | Pro | Cys | Glu | Lys | Gly | Gln | Ile | Lys | Val | Ile | Arg | Lys | |
| 510 | | | | 515 | | | | | 520 | | | | | | 525 | |
| GGA | GAA | GTC | AGC | TGT | TGT | TGG | ACC | TGT | ACA | CCT | TGT | AAG | GAG | AAT | GAG | 1992 |
| Gly | Glu | Val | Ser | Cys | Cys | Trp | Thr | Cys | Thr | Pro | Cys | Lys | Glu | Asn | Glu | |
| | | | | 530 | | | | | 535 | | | | | 540 | | |
| TAT | GTC | TTT | GAT | GAG | TAC | ACA | TGC | AAG | GCA | TGC | CAA | CTG | GGG | TCT | TGG | 2040 |
| Tyr | Val | Phe | Asp | Glu | Tyr | Thr | Cys | Lys | Ala | Cys | Gln | Leu | Gly | Ser | Trp | |
| | | | 545 | | | | | 550 | | | | | 555 | | | |
| CCC | ACT | GAT | GAT | CTC | ACA | GGT | TGT | GAC | TTG | ATC | CCA | GTA | CAG | TAT | CTT | 2088 |
| Pro | Thr | Asp | Asp | Leu | Thr | Gly | Cys | Asp | Leu | Ile | Pro | Val | Gln | Tyr | Leu | |
| | | | 560 | | | | | 565 | | | | | 570 | | | |
| CGA | TGG | GGT | GAC | CCT | GAA | CCC | ATT | GCA | GCT | GTG | GTG | TTT | GCC | TGC | CTT | 2136 |
| Arg | Trp | Gly | Asp | Pro | Glu | Pro | Ile | Ala | Ala | Val | Val | Phe | Ala | Cys | Leu | |
| | | 575 | | | | | 580 | | | | | 585 | | | | |
| GGC | CTC | CTG | GCC | ACC | CTG | TTT | GTT | ACT | GTA | GTC | TTC | ATC | ATT | TAC | CGT | 2184 |
| Gly | Leu | Leu | Ala | Thr | Leu | Phe | Val | Thr | Val | Val | Phe | Ile | Ile | Tyr | Arg | |
| 590 | | | | | 595 | | | | | 600 | | | | | 605 | |
| GAT | ACA | CCA | GTA | GTC | AAG | TCC | TCA | AGC | AGG | GAA | CTC | TGC | TAC | ATT | ATC | 2232 |
| Asp | Thr | Pro | Val | Val | Lys | Ser | Ser | Ser | Arg | Glu | Leu | Cys | Tyr | Ile | Ile | |
| | | | | 610 | | | | | 615 | | | | | 620 | | |
| CTT | GCT | GGC | ATC | TGC | CTG | GGC | TAC | TTA | TGT | ACC | TTC | TGC | CTC | ATT | GCG | 2280 |
| Leu | Ala | Gly | Ile | Cys | Leu | Gly | Tyr | Leu | Cys | Thr | Phe | Cys | Leu | Ile | Ala | |
| | | | 625 | | | | | 630 | | | | | 635 | | | |
| AAG | CCC | AAA | CAG | ATT | TAC | TGC | TAC | CTT | CAG | AGA | ATT | GGC | ATT | GGT | CTC | 2328 |
| Lys | Pro | Lys | Gln | Ile | Tyr | Cys | Tyr | Leu | Gln | Arg | Ile | Gly | Ile | Gly | Leu | |
| | | | 640 | | | | | 645 | | | | | 650 | | | |
| TCC | CCA | GCC | ATG | AGC | TAC | TCA | GCC | CTT | GTA | ACA | AAG | ACC | AAC | CGT | ATT | 2376 |
| Ser | Pro | Ala | Met | Ser | Tyr | Ser | Ala | Leu | Val | Thr | Lys | Thr | Asn | Arg | Ile | |
| | 655 | | | | | 660 | | | | | 665 | | | | | |
| GCA | AGG | ATC | CTG | GCT | GGC | AGC | AAG | AAG | AAG | ATC | TGT | ACC | CCC | AAG | CCC | 2424 |
| Ala | Arg | Ile | Leu | Ala | Gly | Ser | Lys | Lys | Lys | Ile | Cys | Thr | Pro | Lys | Pro | |
| 670 | | | | | 675 | | | | | 680 | | | | | 685 | |
| AGA | TTC | ATG | AGT | GCC | TGT | GCC | CAG | CTA | GTG | ATT | GCT | TTC | ATT | CTC | ATA | 2472 |
| Arg | Phe | Met | Ser | Ala | Cys | Ala | Gln | Leu | Val | Ile | Ala | Phe | Ile | Leu | Ile | |
| | | | | 690 | | | | | 695 | | | | | 700 | | |
| TGC | ATC | CAG | TTG | GGC | ATC | ATC | GTT | GCC | CTC | TTT | ATA | ATG | GAG | CCT | CCT | 2520 |
| Cys | Ile | Gln | Leu | Gly | Ile | Ile | Val | Ala | Leu | Phe | Ile | Met | Glu | Pro | Pro | |
| | | | | 705 | | | | | 710 | | | | | 715 | | |
| GAC | ATA | ATG | CAT | GAC | TAC | CCA | AGC | ATT | CGA | GAA | GTC | TAC | CTG | ATC | TGT | 2568 |
| Asp | Ile | Met | His | Asp | Tyr | Pro | Ser | Ile | Arg | Glu | Val | Tyr | Leu | Ile | Cys | |
| | | 720 | | | | | 725 | | | | | 730 | | | | |
| AAC | ACC | ACC | AAC | CTA | GGA | GTT | GTC | ACT | CCA | CTT | GGA | AAC | AAT | GGA | TTG | 2616 |
| Asn | Thr | Thr | Asn | Leu | Gly | Val | Val | Thr | Pro | Leu | Gly | Asn | Asn | Gly | Leu | |
| | 735 | | | | | 740 | | | | | 745 | | | | | |
| TTG | ATT | TTG | AGC | TGC | ACC | TTC | TAT | GCG | TTC | AAG | ACC | AGA | AAT | GTT | CCA | 2664 |
| Leu | Ile | Leu | Ser | Cys | Thr | Phe | Tyr | Ala | Phe | Lys | Thr | Arg | Asn | Val | Pro | |
| 750 | | | | | 755 | | | | | 760 | | | | | 765 | |
| GCT | AAC | TTC | CCC | GAG | GCC | AAG | TAT | ATC | GCC | CTC | ACA | ATG | TAC | ACG | ACC | 2712 |
| Ala | Asn | Phe | Pro | Glu | Ala | Lys | Tyr | Ile | Ala | Leu | Thr | Met | Tyr | Thr | Thr | |
| | | | 770 | | | | | 775 | | | | | 780 | | | |
| TGC | ATT | AAA | TGG | CTA | GCT | TTT | GTT | CCA | ATC | TAC | TTT | GGC | AGC | AAC | TAC | 2760 |
| Cys | Ile | Lys | Trp | Leu | Ala | Phe | Val | Pro | Ile | Tyr | Phe | Gly | Ser | Asn | Tyr | |
| | | 785 | | | | | 790 | | | | | 795 | | | | |
| AAA | ATC | ATC | ACC | ATG | TGT | TTC | TCG | GTC | AGC | CTC | AGT | GCC | ACA | GTG | GCC | 2808 |
| Lys | Ile | Ile | Thr | Met | Cys | Phe | Ser | Val | Ser | Leu | Ser | Ala | Thr | Val | Ala | |
| | | 800 | | | | | 805 | | | | | 810 | | | | |
| CTA | GGC | TGC | ATG | TTT | GTG | CCG | AAG | GTG | TAC | ATC | ATC | CTG | GCC | AAA | CCA | 2856 |
| Leu | Gly | Cys | Met | Phe | Val | Pro | Lys | Val | Tyr | Ile | Ile | Leu | Ala | Lys | Pro | |
| 815 | | | | | 820 | | | | | 825 | | | | | | |

| | | | | | | | | | | | | | | | | |
|---|---|---|---|---|---|---|---|---|---|---|---|---|---|---|---|---|
| GAG | AGA | AAC | GTG | CGC | AGC | GCC | TTC | ACC | ACA | TCT | ACC | GTG | GTG | CGC | ATG | 2904 |
| Glu | Arg | Asn | Val | Arg | Ser | Ala | Phe | Thr | Thr | Ser | Thr | Val | Val | Arg | Met | |
| 830 | | | | 835 | | | | | 840 | | | | | | 845 | |
| CAT | GTA | GGG | GAT | GGC | AAG | TCA | TCC | TCC | GCA | GCC | AGC | AGA | TCC | AGC | AGC | 2952 |
| His | Val | Gly | Asp | Gly | Lys | Ser | Ser | Ser | Ala | Ala | Ser | Arg | Ser | Ser | Ser | |
| | | | | 850 | | | | | 855 | | | | | 860 | | |
| CTA | GTC | AAC | CTG | TGG | AAG | AGA | AGG | GGC | TCC | TCT | GGG | GAA | ACC | TTA | AGT | 3000 |
| Leu | Val | Asn | Leu | Trp | Lys | Arg | Arg | Gly | Ser | Ser | Gly | Glu | Thr | Leu | Ser | |
| | | | 865 | | | | | 870 | | | | | 875 | | | |
| TCC | AAT | GGA | AAA | TCC | GTC | ACG | TGG | GCC | CAG | AAT | GAG | AAG | AGC | AGC | CGG | 3048 |
| Ser | Asn | Gly | Lys | Ser | Val | Thr | Trp | Ala | Gln | Asn | Glu | Lys | Ser | Ser | Arg | |
| | | 880 | | | | | 885 | | | | | 890 | | | | |
| GGG | CAG | CAC | CTG | TGG | CAG | CGC | CTG | TCC | ATC | CAC | ATC | AAC | AAG | AAA | GAA | 3096 |
| Gly | Gln | His | Leu | Trp | Gln | Arg | Leu | Ser | Ile | His | Ile | Asn | Lys | Lys | Glu | |
| | 895 | | | | | 900 | | | | | 905 | | | | | |
| AAC | CCC | AAC | CAA | ACG | GCC | GTC | ATC | AAG | CCC | TTC | CCC | AAG | AGC | ACG | GAG | 3144 |
| Asn | Pro | Asn | Gln | Thr | Ala | Val | Ile | Lys | Pro | Phe | Pro | Lys | Ser | Thr | Glu | |
| 910 | | | | 915 | | | | | 920 | | | | | | 925 | |
| AGC | CGT | GGC | CTG | GGC | GCT | GGC | GCT | GGC | GCA | GGC | GGG | AGC | GCT | GGG | GGC | 3192 |
| Ser | Arg | Gly | Leu | Gly | Ala | Gly | Ala | Gly | Ala | Gly | Gly | Ser | Ala | Gly | Gly | |
| | | | | 930 | | | | | 935 | | | | | 940 | | |
| GTG | GGG | GCC | ACG | GGC | GGT | GCG | GGC | TGC | GCA | GGC | GCC | GGC | CCA | GGC | GGC | 3240 |
| Val | Gly | Ala | Thr | Gly | Gly | Ala | Gly | Cys | Ala | Gly | Ala | Gly | Pro | Gly | Gly | |
| | | | 945 | | | | | 950 | | | | | 955 | | | |
| CCC | GAG | TCC | CCA | GAC | GCC | GGC | CCC | AAG | GCG | CTG | TTT | GAT | GTG | GCC | GAG | 3288 |
| Pro | Glu | Ser | Pro | Asp | Ala | Gly | Pro | Lys | Ala | Leu | Phe | Asp | Val | Ala | Glu | |
| | | 960 | | | | | 965 | | | | | 970 | | | | |
| GCT | GAG | GAG | CAC | TTC | CCG | GCG | CCC | GCG | CGG | CCG | CGC | TCA | CCG | TCG | CCC | 3336 |
| Ala | Glu | Glu | His | Phe | Pro | Ala | Pro | Ala | Arg | Pro | Arg | Ser | Pro | Ser | Pro | |
| | 975 | | | | | 980 | | | | | 985 | | | | | |
| ATC | AGA | ACG | CTG | AGC | CAC | CGC | GCG | GGC | TCG | GCC | AGC | CGC | ACG | GAC | GAC | 3384 |
| Ile | Arg | Thr | Leu | Ser | His | Arg | Ala | Gly | Ser | Ala | Ser | Arg | Thr | Asp | Asp | |
| 990 | | | | | 995 | | | | | 1000 | | | | | 1005 | |
| GAT | GTG | CCG | TCG | CTG | CAC | TCG | GAG | CCT | GTG | GCG | CGC | AGC | AGC | TCC | TCG | 3432 |
| Asp | Val | Pro | Ser | Leu | His | Ser | Glu | Pro | Val | Ala | Arg | Ser | Ser | Ser | Ser | |
| | | | | 1010 | | | | | 1015 | | | | | 1020 | | |
| CAG | GGC | TCC | CTC | ATG | GAG | CAG | ATC | AGC | AGT | GTG | GTC | ACC | CGC | TTC | ACG | 3480 |
| Gln | Gly | Ser | Leu | Met | Glu | Gln | Ile | Ser | Ser | Val | Val | Thr | Arg | Phe | Thr | |
| | | | 1025 | | | | | 1030 | | | | | 1035 | | | |
| GCC | AAC | ATC | AGC | GAG | CTC | AAC | TCC | ATG | ATG | CTG | TCC | ACC | GCG | GCC | CCC | 3528 |
| Ala | Asn | Ile | Ser | Glu | Leu | Asn | Ser | Met | Met | Leu | Ser | Thr | Ala | Ala | Pro | |
| | | 1040 | | | | | 1045 | | | | | 1050 | | | | |
| AGC | CCC | GGC | GTC | GGC | GCC | CCG | CTC | TGC | TCG | TCC | TAC | CTG | ATC | CCC | AAA | 3576 |
| Ser | Pro | Gly | Val | Gly | Ala | Pro | Leu | Cys | Ser | Ser | Tyr | Leu | Ile | Pro | Lys | |
| | | 1055 | | | | | 1060 | | | | | 1065 | | | | |
| GAG | ATC | CAG | TTG | CCC | ACG | ACC | ATG | ACG | ACC | TTT | GCC | GAA | ATC | CAG | CCT | 3624 |
| Glu | Ile | Gln | Leu | Pro | Thr | Thr | Met | Thr | Thr | Phe | Ala | Glu | Ile | Gln | Pro | |
| 1070 | | | | | 1075 | | | | | 1080 | | | | | 1085 | |
| CTG | CCG | GCC | ATC | GAA | GTC | ACG | GGC | GGC | GCT | CAG | CCC | GCG | GCA | GGG | GCG | 3672 |
| Leu | Pro | Ala | Ile | Glu | Val | Thr | Gly | Gly | Ala | Gln | Pro | Ala | Ala | Gly | Ala | |
| | | | | 1090 | | | | | 1095 | | | | | 1100 | | |
| CAG | GCG | GCT | GGG | GAC | GCG | GCC | CGG | GAG | AGC | CCC | GCG | GCC | GGT | CCC | GAG | 3720 |
| Gln | Ala | Ala | Gly | Asp | Ala | Ala | Arg | Glu | Ser | Pro | Ala | Ala | Gly | Pro | Glu | |
| | | | 1105 | | | | | 1110 | | | | | 1115 | | | |
| GCT | GCG | GCC | GCC | AAG | CCA | GAC | CTG | GAG | GAG | CTG | GTG | GCT | CTC | ACC | CCG | 3768 |
| Ala | Ala | Ala | Ala | Lys | Pro | Asp | Leu | Glu | Glu | Leu | Val | Ala | Leu | Thr | Pro | |
| | | | 1120 | | | | | 1125 | | | | | 1130 | | | |
| CCG | TCC | CCC | TTC | AGA | GAC | TCG | GTG | GAC | TCG | GGG | AGC | ACA | ACC | CCC | AAC | 3816 |
| Pro | Ser | Pro | Phe | Arg | Asp | Ser | Val | Asp | Ser | Gly | Ser | Thr | Thr | Pro | Asn | |
| | | 1135 | | | | | 1140 | | | | | 1145 | | | | |

```
TCG CCA GTG TCC GAG TCG GCC CTC TGT ATC CCG TCG TCT CCC AAA TAT        3864
Ser Pro Val Ser Glu Ser Ala Leu Cys Ile Pro Ser Ser Pro Lys Tyr
1150                1155                1160                1165

GAC ACT CTT ATC ATA AGA GAT TAC ACT CAG AGC TCC TCG TCG TTG TGAATGTC   3919
Asp Thr Leu Ile Ile Arg Asp Tyr Thr Gln Ser Ser Ser Ser Leu
            1170                1175                    1180

TGGAAAGCAC GCCGGCCTGC GCGTGCGGAG CGGAGCCCCC CGTGTTCACA CACACACAAT      3979

GGCAAGCATA GTCGCCTGGT TACGGCCCAG GGGGAAGATG CCAAGGGCAC CCCTTAATGG      4039

AAACACGAGA TCAGTAGTGC TATCTCATGA CAACCGACGA AGAAAC                    4085
```

( 2 ) INFORMATION FOR SEQ ID NO:8:

( i ) SEQUENCE CHARACTERISTICS:
        ( A ) LENGTH: 1180 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Met Val Leu Leu Leu Ile Leu Ser Val Leu Leu Trp Lys Glu Asp Val
1               5                   10                  15

Arg Gly Ser Ala Gln Ser Ser Glu Arg Arg Val Val Ala His Met Pro
                20                  25                  30

Gly Asp Ile Ile Ile Gly Ala Leu Phe Ser Val His His Gln Pro Thr
                35                  40                  45

Val Asp Lys Val His Glu Arg Lys Cys Gly Ala Val Arg Glu Gln Tyr
        50                  55                  60

Gly Ile Gln Arg Val Glu Ala Met Leu His Thr Leu Glu Arg Ile Asn
65                  70                  75                  80

Ser Asp Pro Thr Leu Leu Pro Asn Ile Thr Leu Gly Cys Glu Ile Arg
                85                  90                  95

Asp Ser Cys Trp His Ser Ala Val Ala Leu Glu Gln Ser Ile Glu Phe
                100                 105                 110

Ile Arg Asp Ser Leu Ile Ser Ser Glu Glu Glu Glu Gly Leu Val Arg
            115                 120                 125

Cys Val Asp Gly Ser Ser Ser Ser Phe Arg Ser Lys Lys Pro Ile Val
    130                 135                 140

Gly Val Ile Gly Pro Gly Ser Ser Val Ala Ile Gln Val Gln Asn
145                 150                 155                 160

Leu Leu Gln Leu Phe Asn Ile Pro Gln Ile Ala Tyr Ser Ala Thr Ser
                165                 170                 175

Met Asp Leu Ser Asp Lys Thr Leu Phe Lys Tyr Phe Met Arg Val Val
                180                 185                 190

Pro Ser Asp Ala Gln Gln Ala Arg Ala Met Val Asp Ile Val Lys Arg
            195                 200                 205

Tyr Asn Trp Thr Tyr Val Ser Ala Val His Thr Glu Gly Asn Tyr Gly
        210                 215                 220

Glu Ser Gly Met Glu Ala Ser Lys Asp Met Ser Ala Lys Glu Gly Ile
225                 230                 235                 240

Cys Ile Ala His Ser Tyr Lys Ile Tyr Ser Asn Ala Gly Glu Gln Ser
                245                 250                 255

Phe Asp Lys Leu Leu Lys Lys Leu Thr Ser His Leu Pro Lys Ala Arg
                260                 265                 270

Val Val Ala Cys Phe Cys Glu Gly Met Thr Val Arg Gly Leu Leu Met
        275                 280                 285
```

```
Ala  Met  Arg  Arg  Leu  Gly  Leu  Ala  Gly  Glu  Phe  Leu  Leu  Leu  Gly  Ser
     290                 295                      300

Asp  Gly  Trp  Ala  Asp  Arg  Tyr  Asp  Val  Thr  Asp  Gly  Tyr  Gln  Arg  Glu
305                      310                 315                           320

Ala  Val  Gly  Gly  Ile  Thr  Ile  Lys  Leu  Gln  Ser  Pro  Asp  Val  Lys  Trp
                    325                 330                      335

Phe  Asp  Asp  Tyr  Tyr  Leu  Lys  Leu  Arg  Pro  Glu  Thr  Asn  His  Arg  Asn
               340                      345                      350

Pro  Trp  Phe  Gln  Glu  Phe  Trp  Gln  His  Arg  Phe  Gln  Cys  Arg  Leu  Glu
          355                 360                      365

Ala  Phe  Pro  Gln  Glu  Asn  Ser  Lys  Tyr  Asn  Lys  Thr  Cys  Asn  Ser  Ser
     370                 375                      380

Leu  Thr  Leu  Lys  Thr  His  His  Val  Gln  Asp  Ser  Lys  Met  Gly  Phe  Val
385                      390                 395                           400

Ile  Asn  Ala  Ile  Tyr  Ser  Met  Ala  Tyr  Gly  Leu  His  Asn  Met  Gln  Met
               405                      410                      415

Ser  Leu  Cys  Pro  Gly  Tyr  Ala  Gly  Leu  Cys  Asp  Ala  Met  Lys  Pro  Ile
          420                      425                      430

Asp  Gly  Arg  Lys  Leu  Leu  Glu  Ser  Leu  Met  Lys  Thr  Asn  Phe  Thr  Gly
          435                 440                      445

Val  Ser  Gly  Asp  Thr  Ile  Leu  Phe  Asp  Glu  Asn  Gly  Asp  Ser  Pro  Gly
     450                      455                 460

Arg  Tyr  Glu  Ile  Met  Asn  Phe  Lys  Glu  Met  Gly  Lys  Asp  Tyr  Phe  Asp
465                      470                 475                           480

Tyr  Ile  Asn  Val  Gly  Ser  Trp  Asp  Asn  Gly  Glu  Leu  Lys  Met  Asp  Asp
                    485                 490                      495

Asp  Glu  Val  Trp  Ser  Lys  Lys  Ser  Asn  Ile  Ile  Arg  Ser  Val  Cys  Ser
               500                      505                      510

Glu  Pro  Cys  Glu  Lys  Gly  Gln  Ile  Lys  Val  Ile  Arg  Lys  Gly  Glu  Val
          515                      520                      525

Ser  Cys  Cys  Trp  Thr  Cys  Thr  Pro  Cys  Lys  Glu  Asn  Glu  Tyr  Val  Phe
     530                 535                      540

Asp  Glu  Tyr  Thr  Cys  Lys  Ala  Cys  Gln  Leu  Gly  Ser  Trp  Pro  Thr  Asp
545                      550                 555                           560

Asp  Leu  Thr  Gly  Cys  Asp  Leu  Ile  Pro  Val  Gln  Tyr  Leu  Arg  Trp  Gly
               565                      570                      575

Asp  Pro  Glu  Pro  Ile  Ala  Ala  Val  Val  Phe  Ala  Cys  Leu  Gly  Leu  Leu
          580                      585                      590

Ala  Thr  Leu  Phe  Val  Thr  Val  Val  Phe  Ile  Ile  Tyr  Arg  Asp  Thr  Pro
     595                      600                      605

Val  Val  Lys  Ser  Ser  Ser  Arg  Glu  Leu  Cys  Tyr  Ile  Ile  Leu  Ala  Gly
     610                      615                      620

Ile  Cys  Leu  Gly  Tyr  Leu  Cys  Thr  Phe  Cys  Leu  Ile  Ala  Lys  Pro  Lys
625                      630                      635                      640

Gln  Ile  Tyr  Cys  Tyr  Leu  Gln  Arg  Ile  Gly  Ile  Gly  Leu  Ser  Pro  Ala
                    645                      650                      655

Met  Ser  Tyr  Ser  Ala  Leu  Val  Thr  Lys  Thr  Asn  Arg  Ile  Ala  Arg  Ile
               660                      665                      670

Leu  Ala  Gly  Ser  Lys  Lys  Lys  Ile  Cys  Thr  Pro  Lys  Pro  Arg  Phe  Met
          675                      680                      685

Ser  Ala  Cys  Ala  Gln  Leu  Val  Ile  Ala  Phe  Ile  Leu  Ile  Cys  Ile  Gln
     690                      695                      700

Leu  Gly  Ile  Ile  Val  Ala  Leu  Phe  Ile  Met  Glu  Pro  Pro  Asp  Ile  Met
```

```
705                    710                    715                    720
His Asp Tyr Pro Ser Ile Arg Glu Val Tyr Leu Ile Cys Asn Thr Thr
                725                    730                    735
Asn Leu Gly Val Thr Pro Leu Gly Asn Asn Gly Leu Leu Ile Leu
            740                    745                    750
Ser Cys Thr Phe Tyr Ala Phe Lys Thr Arg Asn Val Pro Ala Asn Phe
            755                    760                    765
Pro Glu Ala Lys Tyr Ile Ala Leu Thr Met Tyr Thr Thr Cys Ile Lys
        770                    775                    780
Trp Leu Ala Phe Val Pro Ile Tyr Phe Gly Ser Asn Tyr Lys Ile Ile
785                    790                    795                    800
Thr Met Cys Phe Ser Val Ser Leu Ser Ala Thr Val Ala Leu Gly Cys
                805                    810                    815
Met Phe Val Pro Lys Val Tyr Ile Ile Leu Ala Lys Pro Glu Arg Asn
            820                    825                    830
Val Arg Ser Ala Phe Thr Thr Ser Thr Val Val Arg Met His Val Gly
            835                    840                    845
Asp Gly Lys Ser Ser Ser Ala Ala Ser Arg Ser Ser Ser Leu Val Asn
        850                    855                    860
Leu Trp Lys Arg Arg Gly Ser Ser Gly Glu Thr Leu Ser Ser Asn Gly
865                    870                    875                    880
Lys Ser Val Thr Trp Ala Gln Asn Glu Lys Ser Ser Arg Gly Gln His
                885                    890                    895
Leu Trp Gln Arg Leu Ser Ile His Ile Asn Lys Lys Glu Asn Pro Asn
            900                    905                    910
Gln Thr Ala Val Ile Lys Pro Phe Pro Lys Ser Thr Glu Ser Arg Gly
            915                    920                    925
Leu Gly Ala Gly Ala Gly Ala Gly Gly Ser Ala Gly Gly Val Gly Ala
        930                    935                    940
Thr Gly Gly Ala Gly Cys Ala Gly Ala Gly Pro Gly Gly Pro Glu Ser
945                    950                    955                    960
Pro Asp Ala Gly Pro Lys Ala Leu Phe Asp Val Ala Glu Ala Glu Glu
                965                    970                    975
His Phe Pro Ala Pro Ala Arg Pro Arg Ser Pro Ser Pro Ile Arg Thr
            980                    985                    990
Leu Ser His Arg Ala Gly Ser Ala Ser Arg Thr Asp Asp Val Pro
        995                    1000                   1005
Ser Leu His Ser Glu Pro Val Ala Arg Ser Ser Ser Ser Gln Gly Ser
    1010                   1015                   1020
Leu Met Glu Gln Ile Ser Ser Val Val Thr Arg Phe Thr Ala Asn Ile
1025                   1030                   1035                   1040
Ser Glu Leu Asn Ser Met Met Leu Ser Thr Ala Ala Pro Ser Pro Gly
                1045                   1050                   1055
Val Gly Ala Pro Leu Cys Ser Ser Tyr Leu Ile Pro Lys Glu Ile Gln
            1060                   1065                   1070
Leu Pro Thr Thr Met Thr Thr Phe Ala Glu Ile Gln Pro Leu Pro Ala
        1075                   1080                   1085
Ile Glu Val Thr Gly Gly Ala Gln Pro Ala Ala Gly Ala Gln Ala Ala
    1090                   1095                   1100
Gly Asp Ala Ala Arg Glu Ser Pro Ala Ala Gly Pro Glu Ala Ala Ala
1105                   1110                   1115                   1120
Ala Lys Pro Asp Leu Glu Glu Leu Val Ala Leu Thr Pro Pro Ser Pro
                1125                   1130                   1135
```

```
Phe Arg Asp Ser Val Asp Ser Gly Ser Thr Thr Pro Asn Ser Pro Val
            1140                1145                1150

Ser Glu Ser Ala Leu Cys Ile Pro Ser Ser Pro Lys Tyr Asp Thr Leu
            1155                1160                1165

Ile Ile Arg Asp Tyr Thr Gln Ser Ser Ser Ser Leu
            1170                1175            1180
```

( 2 ) INFORMATION FOR SEQ ID NO:9:

( i ) SEQUENCE CHARACTERISTICS:
        ( A ) LENGTH: 4181 base pairs
        ( B ) TYPE: nucleic acid
        ( C ) STRANDEDNESS: both
        ( D ) TOPOLOGY: both ( i i ) MOLECULE TYPE: cDNA ( i x ) FEATURE:
        ( A ) NAME/KEY: CDS
        ( B ) LOCATION: 370..4008
        ( D ) OTHER INFORMATION: /product="HUMAN MGLUR5B"
        / note="Variant of MGLUR5A with 96 base pair
        insertion between nucleotides 2999 and 3000."

( x i ) SEQUENCE DESCRIPTION: SEQ ID NO:9:

```
CAGCTCGGCT GTTCTGCGCA CGCTGAGCGG AGGGAATGAG CTTGAGATCA TCTTGGGGGG        60

GAAGCCGGGG ACTGGAGAGG CCGGCTCTGC CCTGCTGATC CCCGTGGCCC AACTTTTCGG       120

GGGGCTAGCT AGACCGAGTC TCACTGCTCG CAGCGCAGCC AACAGGGGGG TTTAGAAGAT       180

CATGACCACA TGGATCATCT AACTAAATGG TACATGGGGA CAAAATGGTC CTTTAGAAAA       240

TACATCTGAA TTGCTGGCTA ATTTCTTGAT TTGCGACTCA ACGTAGGACA TCGCTTGTTC       300

GTAGCTATCA GAACCCTCCT GAATTTTCCC CACCATGCTA TCTTTATTGG CTTGAACTCC       360

TTTCCTAAA ATG GTC CTT CTG TTG ATC CTG TCA GTC TTA CTT TGG AAA          408
          Met Val Leu Leu Leu Ile Leu Ser Val Leu Leu Trp Lys
            1               5                  10

GAA GAT GTC CGT GGG AGT GCA CAG TCC AGT GAG AGG AGG GTG GTG GCT        456
Glu Asp Val Arg Gly Ser Ala Gln Ser Ser Glu Arg Arg Val Val Ala
         15                  20                  25

CAC ATG CCG GGT GAC ATC ATT ATT GGA GCT CTC TTT TCT GTT CAT CAC        504
His Met Pro Gly Asp Ile Ile Ile Gly Ala Leu Phe Ser Val His His
 30                  35                  40                  45

CAG CCT ACT GTG GAC AAA GTT CAT GAG AGG AAG TGT GGG GCG GTC CGT        552
Gln Pro Thr Val Asp Lys Val His Glu Arg Lys Cys Gly Ala Val Arg
                 50                  55                  60

GAA CAG TAT GGC ATT CAG AGA GTG GAG GCC ATG CTG CAT ACC CTG GAA        600
Glu Gln Tyr Gly Ile Gln Arg Val Glu Ala Met Leu His Thr Leu Glu
             65                  70                  75

AGG ATC AAT TCA GAC CCC ACA CTC TTG CCC AAC ATC ACA CTG GGC TGT        648
Arg Ile Asn Ser Asp Pro Thr Leu Leu Pro Asn Ile Thr Leu Gly Cys
         80                  85                  90

GAG ATA AGG GAC TCC TGC TGG CAT TCG GCT GTG GCC CTA GAG CAG AGC        696
Glu Ile Arg Asp Ser Cys Trp His Ser Ala Val Ala Leu Glu Gln Ser
     95                 100                 105

ATT GAG TTC ATA AGA GAT TCC CTC ATT TCT TCA GAA GAG GAA GAA GGC        744
Ile Glu Phe Ile Arg Asp Ser Leu Ile Ser Ser Glu Glu Glu Glu Gly
110                 115                 120                 125

TTG GTA CGC TGT GTG GAT GGC TCC TCC TCT TCC TTC CGC TCC AAG AAG        792
Leu Val Arg Cys Val Asp Gly Ser Ser Ser Ser Phe Arg Ser Lys Lys
                130                 135                 140

CCC ATA GTA GGG GTC ATT GGG CCT GGC TCC AGT TCT GTA GCC ATT CAG        840
Pro Ile Val Gly Val Ile Gly Pro Gly Ser Ser Ser Val Ala Ile Gln
            145                 150                 155
```

| | | | | | | | | | | | | | | | | |
|---|---|---|---|---|---|---|---|---|---|---|---|---|---|---|---|---|
| GTC | CAG | AAT | TTG | CTC | CAG | CTT | TTC | AAC | ATA | CCT | CAG | ATT | GCT | TAC | TCA | 888 |
| Val | Gln | Asn | Leu | Leu | Gln | Leu | Phe | Asn | Ile | Pro | Gln | Ile | Ala | Tyr | Ser | |
| | | 160 | | | | | 165 | | | | | 170 | | | | |
| GCA | ACC | AGC | ATG | GAT | CTG | AGT | GAC | AAG | ACT | CTG | TTC | AAA | TAT | TTC | ATG | 936 |
| Ala | Thr | Ser | Met | Asp | Leu | Ser | Asp | Lys | Thr | Leu | Phe | Lys | Tyr | Phe | Met | |
| | 175 | | | | | 180 | | | | | 185 | | | | | |
| AGG | GTT | GTG | CCT | TCA | GAT | GCT | CAG | CAG | GCA | AGG | GCC | ATG | GTG | GAC | ATA | 984 |
| Arg | Val | Val | Pro | Ser | Asp | Ala | Gln | Gln | Ala | Arg | Ala | Met | Val | Asp | Ile | |
| 190 | | | | | 195 | | | | | 200 | | | | | 205 | |
| GTG | AAG | AGG | TAC | AAC | TGG | ACC | TAT | GTA | TCA | GCC | GTG | CAC | ACA | GAA | GGC | 1032 |
| Val | Lys | Arg | Tyr | Asn | Trp | Thr | Tyr | Val | Ser | Ala | Val | His | Thr | Glu | Gly | |
| | | | | 210 | | | | | 215 | | | | | 220 | | |
| AAC | TAT | GGA | GAA | AGT | GGG | ATG | GAA | GCC | TCC | AAA | GAT | ATG | TCA | GCG | AAG | 1080 |
| Asn | Tyr | Gly | Glu | Ser | Gly | Met | Glu | Ala | Ser | Lys | Asp | Met | Ser | Ala | Lys | |
| | | | | 225 | | | | | 230 | | | | | 235 | | |
| GAA | GGG | ATT | TGC | ATC | GCC | CAC | TCT | TAC | AAA | ATC | TAC | AGT | AAT | GCA | GGG | 1128 |
| Glu | Gly | Ile | Cys | Ile | Ala | His | Ser | Tyr | Lys | Ile | Tyr | Ser | Asn | Ala | Gly | |
| | | | 240 | | | | | 245 | | | | | 250 | | | |
| GAG | CAG | AGC | TTT | GAT | AAG | CTG | CTG | AAG | AAG | CTC | ACA | AGT | CAC | TTG | CCC | 1176 |
| Glu | Gln | Ser | Phe | Asp | Lys | Leu | Leu | Lys | Lys | Leu | Thr | Ser | His | Leu | Pro | |
| | | 255 | | | | | 260 | | | | | 265 | | | | |
| AAG | GCC | CGG | GTG | GTG | GCC | TGC | TTC | TGT | GAG | GGC | ATG | ACG | GTG | AGA | GGT | 1224 |
| Lys | Ala | Arg | Val | Val | Ala | Cys | Phe | Cys | Glu | Gly | Met | Thr | Val | Arg | Gly | |
| 270 | | | | | 275 | | | | | 280 | | | | | 285 | |
| CTG | CTG | ATG | GCC | ATG | AGG | CGC | CTG | GGT | CTA | GCG | GGA | GAA | TTT | CTG | CTT | 1272 |
| Leu | Leu | Met | Ala | Met | Arg | Arg | Leu | Gly | Leu | Ala | Gly | Glu | Phe | Leu | Leu | |
| | | | | 290 | | | | | 295 | | | | | 300 | | |
| CTG | GGC | AGT | GAT | GGC | TGG | GCT | GAC | AGG | TAT | GAT | GTG | ACA | GAT | GGA | TAT | 1320 |
| Leu | Gly | Ser | Asp | Gly | Trp | Ala | Asp | Arg | Tyr | Asp | Val | Thr | Asp | Gly | Tyr | |
| | | | 305 | | | | | 310 | | | | | 315 | | | |
| CAG | CGA | GAA | GCT | GTT | GGT | GGC | ATC | ACA | ATC | AAG | CTC | CAA | TCT | CCC | GAT | 1368 |
| Gln | Arg | Glu | Ala | Val | Gly | Gly | Ile | Thr | Ile | Lys | Leu | Gln | Ser | Pro | Asp | |
| | | 320 | | | | | 325 | | | | | 330 | | | | |
| GTC | AAG | TGG | TTT | GAT | GAT | TAT | TAT | CTG | AAG | CTC | CGG | CCA | GAA | ACA | AAC | 1416 |
| Val | Lys | Trp | Phe | Asp | Asp | Tyr | Tyr | Leu | Lys | Leu | Arg | Pro | Glu | Thr | Asn | |
| | 335 | | | | | 340 | | | | | 345 | | | | | |
| CAC | CGA | AAC | CCT | TGG | TTT | CAA | GAA | TTT | TGG | CAG | CAT | CGT | TTT | CAG | TGC | 1464 |
| His | Arg | Asn | Pro | Trp | Phe | Gln | Glu | Phe | Trp | Gln | His | Arg | Phe | Gln | Cys | |
| 350 | | | | | 355 | | | | | 360 | | | | | 365 | |
| CGA | CTG | GAA | GCG | TTT | CCA | CAG | GAG | AAC | AGC | AAA | TAC | AAC | AAG | ACT | TGC | 1512 |
| Arg | Leu | Glu | Ala | Phe | Pro | Gln | Glu | Asn | Ser | Lys | Tyr | Asn | Lys | Thr | Cys | |
| | | | | 370 | | | | | 375 | | | | | 380 | | |
| AAT | AGT | TCT | CTG | ACT | CTG | AAA | ACA | CAT | CAT | GTT | CAG | GAT | TCC | AAA | ATG | 1560 |
| Asn | Ser | Ser | Leu | Thr | Leu | Lys | Thr | His | His | Val | Gln | Asp | Ser | Lys | Met | |
| | | | 385 | | | | | 390 | | | | | 395 | | | |
| GGA | TTT | GTG | ATC | AAC | GCC | ATC | TAT | TCG | ATG | GCC | TAT | GGG | CTC | CAC | AAC | 1608 |
| Gly | Phe | Val | Ile | Asn | Ala | Ile | Tyr | Ser | Met | Ala | Tyr | Gly | Leu | His | Asn | |
| | | 400 | | | | | 405 | | | | | 410 | | | | |
| ATG | CAG | ATG | TCC | CTC | TGC | CCA | GGC | TAT | GCA | GGA | CTC | TGT | GAT | GCC | ATG | 1656 |
| Met | Gln | Met | Ser | Leu | Cys | Pro | Gly | Tyr | Ala | Gly | Leu | Cys | Asp | Ala | Met | |
| | 415 | | | | | 420 | | | | | 425 | | | | | |
| AAG | CCA | ATT | GAT | GGA | CGG | AAA | CTT | TTG | GAG | TCC | CTG | ATG | AAA | ACC | AAT | 1704 |
| Lys | Pro | Ile | Asp | Gly | Arg | Lys | Leu | Leu | Glu | Ser | Leu | Met | Lys | Thr | Asn | |
| 430 | | | | 435 | | | | | 440 | | | | | 445 | | |
| TTT | ACT | GGG | GTT | TCT | GGA | GAT | ACG | ATC | CTA | TTC | GAT | GAG | AAT | GGA | GAC | 1752 |
| Phe | Thr | Gly | Val | Ser | Gly | Asp | Thr | Ile | Leu | Phe | Asp | Glu | Asn | Gly | Asp | |
| | | | | 450 | | | | | 455 | | | | | 460 | | |
| TCT | CCA | GGA | AGG | TAT | GAA | ATA | ATG | AAT | TTC | AAG | GAA | ATG | GGA | AAA | GAT | 1800 |
| Ser | Pro | Gly | Arg | Tyr | Glu | Ile | Met | Asn | Phe | Lys | Glu | Met | Gly | Lys | Asp | |
| | | | 465 | | | | | 470 | | | | | 475 | | | |

| | | | | | | | | | | | | | | | | |
|---|---|---|---|---|---|---|---|---|---|---|---|---|---|---|---|---|
| TAC | TTT | GAT | TAT | ATC | AAC | GTT | GGA | AGT | TGG | GAC | AAT | GGA | GAA | TTA | AAA | 1848 |
| Tyr | Phe | Asp 480 | Tyr | Ile | Asn | Val | Gly 485 | Ser | Trp | Asp | Asn | Gly 490 | Glu | Leu | Lys | |
| ATG | GAT | GAT | GAT | GAA | GTA | TGG | TCC | AAG | AAA | AGC | AAC | ATC | ATC | AGA | TCT | 1896 |
| Met | Asp 495 | Asp | Asp | Glu | Val | Trp 500 | Ser | Lys | Lys | Ser | Asn 505 | Ile | Ile | Arg | Ser | |
| GTG | TGC | AGT | GAA | CCA | TGT | GAG | AAA | GGC | CAG | ATC | AAG | GTG | ATC | CGA | AAG | 1944 |
| Val 510 | Cys | Ser | Glu | Pro | Cys 515 | Glu | Lys | Gly | Gln | Lys 520 | Lys | Val | Ile | Arg | Lys 525 | |
| GGA | GAA | GTC | AGC | TGT | TGT | TGG | ACC | TGT | ACA | CCT | TGT | AAG | GAG | AAT | GAG | 1992 |
| Gly | Glu | Val | Ser 530 | Cys | Cys | Trp | Thr | Cys 535 | Thr | Pro | Cys | Lys | Glu 540 | Asn | Glu | |
| TAT | GTC | TTT | GAT | GAG | TAC | ACA | TGC | AAG | GCA | TGC | CAA | CTG | GGG | TCT | TGG | 2040 |
| Tyr | Val | Phe | Asp 545 | Glu | Tyr | Thr | Cys | Lys 550 | Ala | Cys | Gln | Leu | Gly 555 | Ser | Trp | |
| CCC | ACT | GAT | GAT | CTC | ACA | GGT | TGT | GAC | TTG | ATC | CCA | GTA | CAG | TAT | CTT | 2088 |
| Pro | Thr | Asp 560 | Asp | Leu | Thr | Gly | Cys 565 | Asp | Leu | Ile | Pro | Val 570 | Gln | Tyr | Leu | |
| CGA | TGG | GGT | GAC | CCT | GAA | CCC | ATT | GCA | GCT | GTG | GTG | TTT | GCC | TGC | CTT | 2136 |
| Arg | Trp 575 | Gly | Asp | Pro | Glu | Pro 580 | Ile | Ala | Ala | Val | Val 585 | Phe | Ala | Cys | Leu | |
| GGC | CTC | CTG | GCC | ACC | CTG | TTT | GTT | ACT | GTA | GTC | TTC | ATC | ATT | TAC | CGT | 2184 |
| Gly 590 | Leu | Leu | Ala | Thr | Leu 595 | Phe | Val | Thr | Val | Val 600 | Phe | Ile | Ile | Tyr | Arg 605 | |
| GAT | ACA | CCA | GTA | GTC | AAG | TCC | TCA | AGC | AGG | GAA | CTC | TGC | TAC | ATT | ATC | 2232 |
| Asp | Thr | Pro | Val | Val 610 | Lys | Ser | Ser | Ser | Arg 615 | Glu | Leu | Cys | Tyr | Ile 620 | Ile | |
| CTT | GCT | GGC | ATC | TGC | CTG | GGC | TAC | TTA | TGT | ACC | TTC | TGC | CTC | ATT | GCG | 2280 |
| Leu | Ala | Gly | Ile 625 | Cys | Leu | Gly | Tyr | Leu 630 | Cys | Thr | Phe | Cys | Leu 635 | Ile | Ala | |
| AAG | CCC | AAA | CAG | ATT | TAC | TGC | TAC | CTT | CAG | AGA | ATT | GGC | ATT | GGT | CTC | 2328 |
| Lys | Pro | Lys 640 | Gln | Ile | Tyr | Cys | Tyr 645 | Leu | Gln | Arg | Ile | Gly 650 | Ile | Gly | Leu | |
| TCC | CCA | GCC | ATG | AGC | TAC | TCA | GCC | CTT | GTA | ACA | AAG | ACC | AAC | CGT | ATT | 2376 |
| Ser | Pro 655 | Ala | Met | Ser | Tyr | Ser 660 | Ala | Leu | Val | Thr | Lys 665 | Thr | Asn | Arg | Ile | |
| GCA | AGG | ATC | CTG | GCT | GGC | AGC | AAG | AAG | AAG | ATC | TGT | ACC | CCC | AAG | CCC | 2424 |
| Ala 670 | Arg | Ile | Leu | Ala | Gly 675 | Ser | Lys | Lys | Lys | Ile 680 | Cys | Thr | Pro | Lys | Pro 685 | |
| AGA | TTC | ATG | AGT | GCC | TGT | GCC | CAG | CTA | GTG | ATT | GCT | TTC | ATT | CTC | ATA | 2472 |
| Arg | Phe | Met | Ser | Ala 690 | Cys | Ala | Gln | Leu | Val 695 | Ile | Ala | Phe | Ile | Leu 700 | Ile | |
| TGC | ATC | CAG | TTG | GGC | ATC | ATC | GTT | GCC | CTC | TTT | ATA | ATG | GAG | CCT | CCT | 2520 |
| Cys | Ile | Gln | Leu 705 | Gly | Ile | Ile | Val | Ala 710 | Leu | Phe | Ile | Met | Glu 715 | Pro | Pro | |
| GAC | ATA | ATG | CAT | GAC | TAC | CCA | AGC | ATT | CGA | GAA | GTC | TAC | CTG | ATC | TGT | 2568 |
| Asp | Ile | Met 720 | His | Asp | Tyr | Pro | Ser 725 | Ile | Arg | Glu | Val | Tyr 730 | Leu | Ile | Cys | |
| AAC | ACC | ACC | AAC | CTA | GGA | GTT | GTC | ACT | CCA | CTT | GGA | AAC | AAT | GGA | TTG | 2616 |
| Asn | Thr | Thr 735 | Asn | Leu | Gly | Val | Val 740 | Thr | Pro | Leu | Gly | Asn 745 | Asn | Gly | Leu | |
| TTG | ATT | TTG | AGC | TGC | ACC | TTC | TAT | GCG | TTC | AAG | ACC | AGA | AAT | GTT | CCA | 2664 |
| Leu 750 | Ile | Leu | Ser | Cys | Thr 755 | Phe | Tyr | Ala | Phe | Lys 760 | Thr | Arg | Asn | Val | Pro 765 | |
| GCT | AAC | TTC | CCC | GAG | GCC | AAG | TAT | ATC | GCC | CTC | ACA | ATG | TAC | ACG | ACC | 2712 |
| Ala | Asn | Phe | Pro | Glu 770 | Ala | Lys | Tyr | Ile | Ala 775 | Leu | Thr | Met | Tyr | Thr 780 | Thr | |
| TGC | ATT | AAA | TGG | CTA | GCT | TTT | GTT | CCA | ATC | TAC | TTT | GGC | AGC | AAC | TAC | 2760 |
| Cys | Ile | Lys | Trp 785 | Leu | Ala | Phe | Val | Pro 790 | Ile | Tyr | Phe | Gly | Ser 795 | Asn | Tyr | |

| | | | | | | | | | | | | | | | | |
|---|---|---|---|---|---|---|---|---|---|---|---|---|---|---|---|---|
| AAA | ATC | ATC | ACC | ATG | TGT | TTC | TCG | GTC | AGC | CTC | AGT | GCC | ACA | GTG | GCC | 2808 |
| Lys | Ile | Ile | Thr | Met | Cys | Phe | Ser | Val | Ser | Leu | Ser | Ala | Thr | Val | Ala | |
| | | 800 | | | | | 805 | | | | | 810 | | | | |
| CTA | GGC | TGC | ATG | TTT | GTG | CCG | AAG | GTG | TAC | ATC | ATC | CTG | GCC | AAA | CCA | 2856 |
| Leu | Gly | Cys | Met | Phe | Val | Pro | Lys | Val | Tyr | Ile | Ile | Leu | Ala | Lys | Pro | |
| | 815 | | | | | 820 | | | | | 825 | | | | | |
| GAG | AGA | AAC | GTG | CGC | AGC | GCC | TTC | ACC | ACA | TCT | ACC | GTG | GTG | CGC | ATG | 2904 |
| Glu | Arg | Asn | Val | Arg | Ser | Ala | Phe | Thr | Thr | Ser | Thr | Val | Val | Arg | Met | |
| 830 | | | | | 835 | | | | | 840 | | | | | 845 | |
| CAT | GTA | GGG | GAT | GGC | AAG | TCA | TCC | TCC | GCA | GCC | AGC | AGA | TCC | AGC | AGC | 2952 |
| His | Val | Gly | Asp | Gly | Lys | Ser | Ser | Ser | Ala | Ala | Ser | Arg | Ser | Ser | Ser | |
| | | | | 850 | | | | | 855 | | | | | 860 | | |
| CTA | GTC | AAC | CTG | TGG | AAG | AGA | AGG | GGC | TCC | TCT | GGG | GAA | ACC | TTA | AGG | 3000 |
| Leu | Val | Asn | Leu | Trp | Lys | Arg | Arg | Gly | Ser | Ser | Gly | Glu | Thr | Leu | Arg | |
| | | | 865 | | | | | 870 | | | | | 875 | | | |
| TAC | AAA | GAC | AGG | AGA | CTG | GCC | CAG | CAC | AAG | TCG | GAA | ATA | GAG | TGT | TTC | 3048 |
| Tyr | Lys | Asp | Arg | Arg | Leu | Ala | Gln | His | Lys | Ser | Glu | Ile | Glu | Cys | Phe | |
| | | 880 | | | | | 885 | | | | | 890 | | | | |
| ACC | CCC | AAA | GGG | AGT | ATG | GGG | AAT | GGT | GGG | AGA | GCA | ACA | ATG | AGC | AGT | 3096 |
| Thr | Pro | Lys | Gly | Ser | Met | Gly | Asn | Gly | Gly | Arg | Ala | Thr | Met | Ser | Ser | |
| | 895 | | | | | 900 | | | | | 905 | | | | | |
| TCC | AAT | GGA | AAA | TCC | GTC | ACG | TGG | GCC | CAG | AAT | GAG | AAG | AGC | AGC | CGG | 3144 |
| Ser | Asn | Gly | Lys | Ser | Val | Thr | Trp | Ala | Gln | Asn | Glu | Lys | Ser | Ser | Arg | |
| 910 | | | | | 915 | | | | | 920 | | | | | 925 | |
| GGG | CAG | CAC | CTG | TGG | CAG | CGC | CTG | TCC | ATC | CAC | ATC | AAC | AAG | AAA | GAA | 3192 |
| Gly | Gln | His | Leu | Trp | Gln | Arg | Leu | Ser | Ile | His | Ile | Asn | Lys | Lys | Glu | |
| | | | | 930 | | | | | 935 | | | | | 940 | | |
| AAC | CCC | AAC | CAA | ACG | GCC | GTC | ATC | AAG | CCC | TTC | CCC | AAG | AGC | ACG | GAG | 3240 |
| Asn | Pro | Asn | Gln | Thr | Ala | Val | Ile | Lys | Pro | Phe | Pro | Lys | Ser | Thr | Glu | |
| | | | 945 | | | | | 950 | | | | | 955 | | | |
| AGC | CGT | GGC | CTG | GGC | GCT | GGC | GCT | GGC | GCA | GGC | GGG | AGC | GCT | GGG | GGC | 3288 |
| Ser | Arg | Gly | Leu | Gly | Ala | Gly | Ala | Gly | Ala | Gly | Gly | Ser | Ala | Gly | Gly | |
| | | 960 | | | | | 965 | | | | | 970 | | | | |
| GTG | GGG | GCC | ACG | GGC | GGT | GCG | GGC | TGC | GCA | GGC | GCC | GGC | CCA | GGC | GGC | 3336 |
| Val | Gly | Ala | Thr | Gly | Gly | Ala | Gly | Cys | Ala | Gly | Ala | Gly | Pro | Gly | Gly | |
| | 975 | | | | | 980 | | | | | 985 | | | | | |
| CCC | GAG | TCC | CCA | GAC | GCC | GGC | CCC | AAG | GCG | CTG | TTT | GAT | GTG | GCC | GAG | 3384 |
| Pro | Glu | Ser | Pro | Asp | Ala | Gly | Pro | Lys | Ala | Leu | Phe | Asp | Val | Ala | Glu | |
| 990 | | | | 995 | | | | | 1000 | | | | | 1005 | | |
| GCT | GAG | GAG | CAC | TTC | CCG | GCG | CCC | GCG | CGG | CCG | CGC | TCA | CCG | TCG | CCC | 3432 |
| Ala | Glu | Glu | His | Phe | Pro | Ala | Pro | Ala | Arg | Pro | Arg | Ser | Pro | Ser | Pro | |
| | | | | 1010 | | | | | 1015 | | | | | 1020 | | |
| ATC | AGA | ACG | CTG | AGC | CAC | CGC | GCG | GGC | TCG | GCC | AGC | CGC | ACG | GAC | GAC | 3480 |
| Ile | Arg | Thr | Leu | Ser | His | Arg | Ala | Gly | Ser | Ala | Ser | Arg | Thr | Asp | Asp | |
| | | | 1025 | | | | | 1030 | | | | | 1035 | | | |
| GAT | GTG | CCG | TCG | CTG | CAC | TCG | GAG | CCT | GTG | GCG | CGC | AGC | AGC | TCC | TCG | 3528 |
| Asp | Val | Pro | Ser | Leu | His | Ser | Glu | Pro | Val | Ala | Arg | Ser | Ser | Ser | Ser | |
| | | 1040 | | | | | 1045 | | | | | 1050 | | | | |
| CAG | GGC | TCC | CTC | ATG | GAG | CAG | ATC | AGC | AGT | GTG | GTC | ACC | CGC | TTC | ACG | 3576 |
| Gln | Gly | Ser | Leu | Met | Glu | Gln | Ile | Ser | Ser | Val | Val | Thr | Arg | Phe | Thr | |
| | 1055 | | | | | 1060 | | | | | 1065 | | | | | |
| GCC | AAC | ATC | AGC | GAG | CTC | AAC | TCC | ATG | ATG | CTG | TCC | ACC | GCG | GCC | CCC | 3624 |
| Ala | Asn | Ile | Ser | Glu | Leu | Asn | Ser | Met | Met | Leu | Ser | Thr | Ala | Ala | Pro | |
| 1070 | | | | 1075 | | | | | 1080 | | | | | 1085 | | |
| AGC | CCC | GGC | GTC | GGC | GCC | CCG | CTC | TGC | TCG | TCC | TAC | CTG | ATC | CCC | AAA | 3672 |
| Ser | Pro | Gly | Val | Gly | Ala | Pro | Leu | Cys | Ser | Ser | Tyr | Leu | Ile | Pro | Lys | |
| | | | | 1090 | | | | | 1095 | | | | | 1100 | | |
| GAG | ATC | CAG | TTG | CCC | ACG | ACC | ATG | ACG | ACC | TTT | GCC | GAA | ATC | CAG | CCT | 3720 |
| Glu | Ile | Gln | Leu | Pro | Thr | Thr | Met | Thr | Thr | Phe | Ala | Glu | Ile | Gln | Pro | |
| | | | 1105 | | | | | 1110 | | | | | 1115 | | | |

```
CTG CCG GCC ATC GAA GTC ACG GGC GGC GCT CAG CCC GCG GCA GGG GCG        3768
Leu Pro Ala Ile Glu Val Thr Gly Gly Ala Gln Pro Ala Ala Gly Ala
        1120            1125            1130

CAG GCG GCT GGG GAC GCG GCC CGG GAG AGC CCC GCG GCC GGT CCC GAG        3816
Gln Ala Ala Gly Asp Ala Ala Arg Glu Ser Pro Ala Ala Gly Pro Glu
        1135            1140            1145

GCT GCG GCC GCC AAG CCA GAC CTG GAG GAG CTG GTG GCT CTC ACC CCG        3864
Ala Ala Ala Ala Lys Pro Asp Leu Glu Glu Leu Val Ala Leu Thr Pro
1150            1155            1160            1165

CCG TCC CCC TTC AGA GAC TCG GTG GAC TCG GGG AGC ACA ACC CCC AAC        3912
Pro Ser Pro Phe Arg Asp Ser Val Asp Ser Gly Ser Thr Thr Pro Asn
        1170            1175            1180

TCG CCA GTG TCC GAG TCG GCC CTC TGT ATC CCG TCG TCT CCC AAA TAT        3960
Ser Pro Val Ser Glu Ser Ala Leu Cys Ile Pro Ser Ser Pro Lys Tyr
        1185            1190            1195

GAC ACT CTT ATC ATA AGA GAT TAC ACT CAG AGC TCC TCG TCG TTG TGAATGTC  4015
Asp Thr Leu Ile Ile Arg Asp Tyr Thr Gln Ser Ser Ser Ser Leu
        1200            1205            1210

TGGAAAGCAC GCCGGCCTGC GCGTGCGGAG CGGAGCCCCC CGTGTTCACA CACACACAAT     4075

GGCAAGCATA GTCGCCTGGT TACGGCCCAG GGGGAAGATG CCAAGGGCAC CCCTTAATGG     4135

AAACACGAGA TCAGTAGTGC TATCTCATGA CAACCGACGA AGAAAC                    4181
```

( 2 ) INFORMATION FOR SEQ ID NO:10:

( i ) SEQUENCE CHARACTERISTICS:
        ( A ) LENGTH: 1212 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

```
Met Val Leu Leu Leu Ile Leu Ser Val Leu Leu Trp Lys Glu Asp Val
 1               5                   10                  15

Arg Gly Ser Ala Gln Ser Ser Glu Arg Arg Val Val Ala His Met Pro
            20                  25                  30

Gly Asp Ile Ile Ile Gly Ala Leu Phe Ser Val His His Gln Pro Thr
            35                  40                  45

Val Asp Lys Val His Glu Arg Lys Cys Gly Ala Val Arg Glu Gln Tyr
        50                  55                  60

Gly Ile Gln Arg Val Glu Ala Met Leu His Thr Leu Glu Arg Ile Asn
 65                  70                  75                  80

Ser Asp Pro Thr Leu Leu Pro Asn Ile Thr Leu Gly Cys Glu Ile Arg
                85                  90                  95

Asp Ser Cys Trp His Ser Ala Val Ala Leu Glu Gln Ser Ile Glu Phe
            100                 105                 110

Ile Arg Asp Ser Leu Ile Ser Ser Glu Glu Glu Gly Leu Val Arg
            115                 120                 125

Cys Val Asp Gly Ser Ser Ser Ser Phe Arg Ser Lys Lys Pro Ile Val
        130                 135                 140

Gly Val Ile Gly Pro Gly Ser Ser Ser Val Ala Ile Gln Val Gln Asn
145                 150                 155                 160

Leu Leu Gln Leu Phe Asn Ile Pro Gln Ile Ala Tyr Ser Ala Thr Ser
                165                 170                 175

Met Asp Leu Ser Asp Lys Thr Leu Phe Lys Tyr Phe Met Arg Val Val
            180                 185                 190

Pro Ser Asp Ala Gln Gln Ala Arg Ala Met Val Asp Ile Val Lys Arg
```

-continued

|  | 195 |  |  |  | 200 |  |  |  | 205 |  |  |  |
|---|---|---|---|---|---|---|---|---|---|---|---|---|
| Tyr | Asn | Trp | Thr | Tyr | Val | Ser | Ala | Val | His | Thr | Glu | Gly | Asn | Tyr | Gly |
| | 210 | | | | 215 | | | | 220 | | | |

```
            195                     200                     205
Tyr Asn Trp Thr Tyr Val Ser Ala Val His Thr Glu Gly Asn Tyr Gly
    210                 215                 220
Glu Ser Gly Met Glu Ala Ser Lys Asp Met Ser Ala Lys Glu Gly Ile
225                 230                 235                 240
Cys Ile Ala His Ser Tyr Lys Ile Tyr Ser Asn Ala Gly Glu Gln Ser
                245                 250                 255
Phe Asp Lys Leu Leu Lys Lys Leu Thr Ser His Leu Pro Lys Ala Arg
                260                 265                 270
Val Val Ala Cys Phe Cys Glu Gly Met Thr Val Arg Gly Leu Leu Met
                275                 280                 285
Ala Met Arg Arg Leu Gly Leu Ala Gly Glu Phe Leu Leu Leu Gly Ser
290                 295                 300
Asp Gly Trp Ala Asp Arg Tyr Asp Val Thr Asp Gly Tyr Gln Arg Glu
305                 310                 315                 320
Ala Val Gly Gly Ile Thr Ile Lys Leu Gln Ser Pro Asp Val Lys Trp
                325                 330                 335
Phe Asp Asp Tyr Tyr Leu Lys Leu Arg Pro Glu Thr Asn His Arg Asn
                340                 345                 350
Pro Trp Phe Gln Glu Phe Trp Gln His Arg Phe Gln Cys Arg Leu Glu
                355                 360                 365
Ala Phe Pro Gln Glu Asn Ser Lys Tyr Asn Lys Thr Cys Asn Ser Ser
370                 375                 380
Leu Thr Leu Lys Thr His His Val Gln Asp Ser Lys Met Gly Phe Val
385                 390                 395                 400
Ile Asn Ala Ile Tyr Ser Met Ala Tyr Gly Leu His Asn Met Gln Met
                405                 410                 415
Ser Leu Cys Pro Gly Tyr Ala Gly Leu Cys Asp Ala Met Lys Pro Ile
                420                 425                 430
Asp Gly Arg Lys Leu Leu Glu Ser Leu Met Lys Thr Asn Phe Thr Gly
                435                 440                 445
Val Ser Gly Asp Thr Ile Leu Phe Asp Glu Asn Gly Asp Ser Pro Gly
450                 455                 460
Arg Tyr Glu Ile Met Asn Phe Lys Glu Met Gly Lys Asp Tyr Phe Asp
465                 470                 475                 480
Tyr Ile Asn Val Gly Ser Trp Asp Asn Gly Glu Leu Lys Met Asp Asp
                485                 490                 495
Asp Glu Val Trp Ser Lys Lys Ser Asn Ile Ile Arg Ser Val Cys Ser
                500                 505                 510
Glu Pro Cys Glu Lys Gly Gln Ile Lys Val Ile Arg Lys Gly Glu Val
                515                 520                 525
Ser Cys Cys Trp Thr Cys Thr Pro Cys Lys Glu Asn Glu Tyr Val Phe
    530                 535                 540
Asp Glu Tyr Thr Cys Lys Ala Cys Gln Leu Gly Ser Trp Pro Thr Asp
545                 550                 555                 560
Asp Leu Thr Gly Cys Asp Leu Ile Pro Val Gln Tyr Leu Arg Trp Gly
                565                 570                 575
Asp Pro Glu Pro Ile Ala Ala Val Val Phe Ala Cys Leu Gly Leu Leu
                580                 585                 590
Ala Thr Leu Phe Val Thr Val Val Phe Ile Ile Tyr Arg Asp Thr Pro
                595                 600                 605
Val Val Lys Ser Ser Ser Arg Glu Leu Cys Tyr Ile Ile Leu Ala Gly
    610                 615                 620
```

| | | | | | | | | | | | | | | |
|---|---|---|---|---|---|---|---|---|---|---|---|---|---|---|
| Ile | Cys | Leu | Gly | Tyr | Leu | Cys | Thr | Phe | Cys | Leu | Ile | Ala | Lys | Pro | Lys |
| 625 | | | | 630 | | | | | 635 | | | | | 640 |
| Gln | Ile | Tyr | Cys | Tyr | Leu | Gln | Arg | Ile | Gly | Ile | Gly | Leu | Ser | Pro | Ala |
| | | | 645 | | | | | 650 | | | | 655 | | |
| Met | Ser | Tyr | Ser | Ala | Leu | Val | Thr | Lys | Thr | Asn | Arg | Ile | Ala | Arg | Ile |
| | | | 660 | | | | 665 | | | | 670 | | | |
| Leu | Ala | Gly | Ser | Lys | Lys | Lys | Ile | Cys | Thr | Pro | Lys | Pro | Arg | Phe | Met |
| | | 675 | | | | 680 | | | | 685 | | | | |
| Ser | Ala | Cys | Ala | Gln | Leu | Val | Ile | Ala | Phe | Ile | Leu | Ile | Cys | Ile | Gln |
| | 690 | | | | 695 | | | | | 700 | | | | |
| Leu | Gly | Ile | Ile | Val | Ala | Leu | Phe | Ile | Met | Glu | Pro | Pro | Asp | Ile | Met |
| 705 | | | | 710 | | | | 715 | | | | | 720 | | |
| His | Asp | Tyr | Pro | Ser | Ile | Arg | Glu | Val | Tyr | Leu | Ile | Cys | Asn | Thr | Thr |
| | | | 725 | | | | 730 | | | | | 735 | | | |
| Asn | Leu | Gly | Val | Val | Thr | Pro | Leu | Gly | Asn | Asn | Gly | Leu | Leu | Ile | Leu |
| | | | 740 | | | | 745 | | | | 750 | | | | |
| Ser | Cys | Thr | Phe | Tyr | Ala | Phe | Lys | Thr | Arg | Asn | Val | Pro | Ala | Asn | Phe |
| | | 755 | | | | 760 | | | | 765 | | | | | |
| Pro | Glu | Ala | Lys | Tyr | Ile | Ala | Leu | Thr | Met | Tyr | Thr | Thr | Cys | Ile | Lys |
| | 770 | | | | 775 | | | | 780 | | | | | | |
| Trp | Leu | Ala | Phe | Val | Pro | Ile | Tyr | Phe | Gly | Ser | Asn | Tyr | Lys | Ile | Ile |
| 785 | | | | 790 | | | | 795 | | | | | 800 | | |
| Thr | Met | Cys | Phe | Ser | Val | Ser | Leu | Ser | Ala | Thr | Val | Ala | Leu | Gly | Cys |
| | | | 805 | | | | 810 | | | | 815 | | | | |
| Met | Phe | Val | Pro | Lys | Val | Tyr | Ile | Ile | Leu | Ala | Lys | Pro | Glu | Arg | Asn |
| | | 820 | | | | 825 | | | | 830 | | | | | |
| Val | Arg | Ser | Ala | Phe | Thr | Thr | Ser | Thr | Val | Val | Arg | Met | His | Val | Gly |
| | 835 | | | | 840 | | | | | 845 | | | | | |
| Asp | Gly | Lys | Ser | Ser | Ser | Ala | Ala | Ser | Arg | Ser | Ser | Ser | Leu | Val | Asn |
| 850 | | | | | 855 | | | | 860 | | | | | | |
| Leu | Trp | Lys | Arg | Arg | Gly | Ser | Ser | Gly | Glu | Thr | Leu | Arg | Tyr | Lys | Asp |
| 865 | | | | 870 | | | | 875 | | | | | 880 | | |
| Arg | Arg | Leu | Ala | Gln | His | Lys | Ser | Glu | Ile | Glu | Cys | Phe | Thr | Pro | Lys |
| | | | 885 | | | | 890 | | | | | 895 | | | |
| Gly | Ser | Met | Gly | Asn | Gly | Gly | Arg | Ala | Thr | Met | Ser | Ser | Ser | Asn | Gly |
| | | 900 | | | | 905 | | | | 910 | | | | | |
| Lys | Ser | Val | Thr | Trp | Ala | Gln | Asn | Glu | Lys | Ser | Ser | Arg | Gly | Gln | His |
| | 915 | | | | 920 | | | | 925 | | | | | | |
| Leu | Trp | Gln | Arg | Leu | Ser | Ile | His | Ile | Asn | Lys | Lys | Glu | Asn | Pro | Asn |
| 930 | | | | | 935 | | | | 940 | | | | | | |
| Gln | Thr | Ala | Val | Ile | Lys | Pro | Phe | Pro | Lys | Ser | Thr | Glu | Ser | Arg | Gly |
| 945 | | | | | 950 | | | | 955 | | | | | 960 | |
| Leu | Gly | Ala | Gly | Ala | Gly | Ala | Gly | Gly | Ser | Ala | Gly | Gly | Val | Gly | Ala |
| | | | | 965 | | | | 970 | | | | 975 | | | |
| Thr | Gly | Gly | Ala | Gly | Cys | Ala | Gly | Ala | Gly | Pro | Gly | Gly | Pro | Glu | Ser |
| | | | 980 | | | | 985 | | | | 990 | | | | |
| Pro | Asp | Ala | Gly | Pro | Lys | Ala | Leu | Phe | Asp | Val | Ala | Glu | Ala | Glu | Glu |
| | | 995 | | | | 1000 | | | | 1005 | | | | | |
| His | Phe | Pro | Ala | Pro | Ala | Arg | Pro | Arg | Ser | Pro | Ser | Pro | Ile | Arg | Thr |
| | 1010 | | | | 1015 | | | | 1020 | | | | | | |
| Leu | Ser | His | Arg | Ala | Gly | Ser | Ala | Ser | Arg | Thr | Asp | Asp | Val | Pro | |
| 1025 | | | | 1030 | | | | 1035 | | | | 1040 | | | |
| Ser | Leu | His | Ser | Glu | Pro | Val | Ala | Arg | Ser | Ser | Ser | Gln | Gly | Ser | |
| | | | | 1045 | | | | 1050 | | | | 1055 | | | |

```
Leu Met Glu Gln Ile Ser Ser Val Val Thr Arg Phe Thr Ala Asn Ile
        1060                1065                1070

Ser Glu Leu Asn Ser Met Met Leu Ser Thr Ala Ala Pro Ser Pro Gly
        1075                1080                1085

Val Gly Ala Pro Leu Cys Ser Ser Tyr Leu Ile Pro Lys Glu Ile Gln
        1090                1095                1100

Leu Pro Thr Thr Met Thr Thr Phe Ala Glu Ile Gln Pro Leu Pro Ala
1105                1110                1115                1120

Ile Glu Val Thr Gly Gly Ala Gln Pro Ala Ala Gly Ala Gln Ala Ala
                1125                1130                1135

Gly Asp Ala Ala Arg Glu Ser Pro Ala Ala Gly Pro Glu Ala Ala Ala
                1140                1145                1150

Ala Lys Pro Asp Leu Glu Glu Leu Val Ala Leu Thr Pro Pro Ser Pro
        1155                1160                1165

Phe Arg Asp Ser Val Asp Ser Gly Ser Thr Thr Pro Asn Ser Pro Val
        1170                1175                1180

Ser Glu Ser Ala Leu Cys Ile Pro Ser Ser Pro Lys Tyr Asp Thr Leu
1185                1190                1195                1200

Ile Ile Arg Asp Tyr Thr Gln Ser Ser Ser Ser Leu
                1205                1210
```

( 2 ) INFORMATION FOR SEQ ID NO:11:

( i ) SEQUENCE CHARACTERISTICS:
        ( A ) LENGTH: 3282 base pairs
        ( B ) TYPE: nucleic acid
        ( C ) STRANDEDNESS: both
        ( D ) TOPOLOGY: both ( i i ) MOLECULE TYPE: cDNA ( i x ) FEATURE:
        ( A ) NAME/KEY: CDS
        ( B ) LOCATION: 370..3003
        ( D ) OTHER INFORMATION: /product="HUMAN MGLUR5C"
            / note="Variant of MGLUR5A with truncated 3'end."

( x i ) SEQUENCE DESCRIPTION: SEQ ID NO:11:

```
CAGCTCGGCT GTTCTGCGCA CGCTGAGCGG AGGGAATGAG CTTGAGATCA TCTTGGGGGG      60

GAAGCCGGGG ACTGGAGAGG CCGGCTCTGC CCTGCTGATC CCCGTGGCCC AACTTTTCGG     120

GGGGCTAGCT AGACCGAGTC TCACTGCTCG CAGCGCAGCC AACAGGGGGG TTTAGAAGAT     180

CATGACCACA TGGATCATCT AACTAAATGG TACATGGGGA CAAAATGGTC CTTTAGAAAA     240

TACATCTGAA TTGCTGGCTA ATTTCTTGAT TTGCGACTCA ACGTAGGACA TCGCTTGTTC     300

GTAGCTATCA GAACCCTCCT GAATTTTCCC CACCATGCTA TCTTTATTGG CTTGAACTCC     360

TTTCCTAAA ATG GTC CTT CTG TTG ATC CTG TCA GTC TTA CTT TGG AAA        408
            Met Val Leu Leu Leu Ile Leu Ser Val Leu Leu Trp Lys
              1               5                   10

GAA GAT GTC CGT GGG AGT GCA CAG TCC AGT GAG AGG AGG GTG GTG GCT      456
Glu Asp Val Arg Gly Ser Ala Gln Ser Ser Glu Arg Arg Val Val Ala
       15                  20                  25

CAC ATG CCG GGT GAC ATC ATT ATT GGA GCT CTC TTT TCT GTT CAT CAC      504
His Met Pro Gly Asp Ile Ile Ile Gly Ala Leu Phe Ser Val His His
 30                  35                  40                  45

CAG CCT ACT GTG GAC AAA GTT CAT GAG AGG AAG TGT GGG GCG GTC CGT      552
Gln Pro Thr Val Asp Lys Val His Glu Arg Lys Cys Gly Ala Val Arg
                50                  55                  60

GAA CAG TAT GGC ATT CAG AGA GTG GAG GCC ATG CTG CAT ACC CTG GAA      600
Glu Gln Tyr Gly Ile Gln Arg Val Glu Ala Met Leu His Thr Leu Glu
```

| | | | | | | | | | | | | | | | | |
|---|---|---|---|---|---|---|---|---|---|---|---|---|---|---|---|---|
| | | 65 | | | | | 70 | | | | | 75 | | | | |
| AGG | ATC | AAT | TCA | GAC | CCC | ACA | CTC | TTG | CCC | AAC | ATC | ACA | CTG | GGC | TGT | 648 |
| Arg | Ile | Asn | Ser | Asp | Pro | Thr | Leu | Leu | Pro | Asn | Ile | Thr | Leu | Gly | Cys | |
| | | 80 | | | | | 85 | | | | | 90 | | | | |
| GAG | ATA | AGG | GAC | TCC | TGC | TGG | CAT | TCG | GCT | GTG | GCC | CTA | GAG | CAG | AGC | 696 |
| Glu | Ile | Arg | Asp | Ser | Cys | Trp | His | Ser | Ala | Val | Ala | Leu | Glu | Gln | Ser | |
| | | 95 | | | | | 100 | | | | | 105 | | | | |
| ATT | GAG | TTC | ATA | AGA | GAT | TCC | CTC | ATT | TCT | TCA | GAA | GAG | GAA | GAA | GGC | 744 |
| Ile | Glu | Phe | Ile | Arg | Asp | Ser | Leu | Ile | Ser | Ser | Glu | Glu | Glu | Glu | Gly | |
| 110 | | | | | 115 | | | | | 120 | | | | | 125 | |
| TTG | GTA | CGC | TGT | GTG | GAT | GGC | TCC | TCC | TCT | TCC | TTC | CGC | TCC | AAG | AAG | 792 |
| Leu | Val | Arg | Cys | Val | Asp | Gly | Ser | Ser | Ser | Ser | Phe | Arg | Ser | Lys | Lys | |
| | | | | 130 | | | | | 135 | | | | | 140 | | |
| CCC | ATA | GTA | GGG | GTC | ATT | GGG | CCT | GGC | TCC | AGT | TCT | GTA | GCC | ATT | CAG | 840 |
| Pro | Ile | Val | Gly | Val | Ile | Gly | Pro | Gly | Ser | Ser | Ser | Val | Ala | Ile | Gln | |
| | | | 145 | | | | | 150 | | | | | 155 | | | |
| GTC | CAG | AAT | TTG | CTC | CAG | CTT | TTC | AAC | ATA | CCT | CAG | ATT | GCT | TAC | TCA | 888 |
| Val | Gln | Asn | Leu | Leu | Gln | Leu | Phe | Asn | Ile | Pro | Gln | Ile | Ala | Tyr | Ser | |
| | | 160 | | | | | 165 | | | | | 170 | | | | |
| GCA | ACC | AGC | ATG | GAT | CTG | AGT | GAC | AAG | ACT | CTG | TTC | AAA | TAT | TTC | ATG | 936 |
| Ala | Thr | Ser | Met | Asp | Leu | Ser | Asp | Lys | Thr | Leu | Phe | Lys | Tyr | Phe | Met | |
| | 175 | | | | | 180 | | | | | 185 | | | | | |
| AGG | GTT | GTG | CCT | TCA | GAT | GCT | CAG | CAG | GCA | AGG | GCC | ATG | GTG | GAC | ATA | 984 |
| Arg | Val | Val | Pro | Ser | Asp | Ala | Gln | Gln | Ala | Arg | Ala | Met | Val | Asp | Ile | |
| 190 | | | | | 195 | | | | | 200 | | | | | 205 | |
| GTG | AAG | AGG | TAC | AAC | TGG | ACC | TAT | GTA | TCA | GCC | GTG | CAC | ACA | GAA | GGC | 1032 |
| Val | Lys | Arg | Tyr | Asn | Trp | Thr | Tyr | Val | Ser | Ala | Val | His | Thr | Glu | Gly | |
| | | | | 210 | | | | | 215 | | | | | 220 | | |
| AAC | TAT | GGA | GAA | AGT | GGG | ATG | GAA | GCC | TCC | AAA | GAT | ATG | TCA | GCG | AAG | 1080 |
| Asn | Tyr | Gly | Glu | Ser | Gly | Met | Glu | Ala | Ser | Lys | Asp | Met | Ser | Ala | Lys | |
| | | | 225 | | | | | 230 | | | | | 235 | | | |
| GAA | GGG | ATT | TGC | ATC | GCC | CAC | TCT | TAC | AAA | ATC | TAC | AGT | AAT | GCA | GGG | 1128 |
| Glu | Gly | Ile | Cys | Ile | Ala | His | Ser | Tyr | Lys | Ile | Tyr | Ser | Asn | Ala | Gly | |
| | | 240 | | | | | 245 | | | | | 250 | | | | |
| GAG | CAG | AGC | TTT | GAT | AAG | CTG | CTG | AAG | AAG | CTC | ACA | AGT | CAC | TTG | CCC | 1176 |
| Glu | Gln | Ser | Phe | Asp | Lys | Leu | Leu | Lys | Lys | Leu | Thr | Ser | His | Leu | Pro | |
| | 255 | | | | | 260 | | | | | 265 | | | | | |
| AAG | GCC | CGG | GTG | GTG | GCC | TGC | TTC | TGT | GAG | GGC | ATG | ACG | GTG | AGA | GGT | 1224 |
| Lys | Ala | Arg | Val | Val | Ala | Cys | Phe | Cys | Glu | Gly | Met | Thr | Val | Arg | Gly | |
| 270 | | | | | 275 | | | | | 280 | | | | | 285 | |
| CTG | CTG | ATG | GCC | ATG | AGG | CGC | CTG | GGT | CTA | GCG | GGA | GAA | TTT | CTG | CTT | 1272 |
| Leu | Leu | Met | Ala | Met | Arg | Arg | Leu | Gly | Leu | Ala | Gly | Glu | Phe | Leu | Leu | |
| | | | | 290 | | | | | 295 | | | | | 300 | | |
| CTG | GGC | AGT | GAT | GGC | TGG | GCT | GAC | AGG | TAT | GAT | GTG | ACA | GAT | GGA | TAT | 1320 |
| Leu | Gly | Ser | Asp | Gly | Trp | Ala | Asp | Arg | Tyr | Asp | Val | Thr | Asp | Gly | Tyr | |
| | | | 305 | | | | | 310 | | | | | 315 | | | |
| CAG | CGA | GAA | GCT | GTT | GGT | GGC | ATC | ACA | ATC | AAG | CTC | CAA | TCT | CCC | GAT | 1368 |
| Gln | Arg | Glu | Ala | Val | Gly | Gly | Ile | Thr | Ile | Lys | Leu | Gln | Ser | Pro | Asp | |
| | | 320 | | | | | 325 | | | | | 330 | | | | |
| GTC | AAG | TGG | TTT | GAT | GAT | TAT | TAT | CTG | AAG | CTC | CGG | CCA | GAA | ACA | AAC | 1416 |
| Val | Lys | Trp | Phe | Asp | Asp | Tyr | Tyr | Leu | Lys | Leu | Arg | Pro | Glu | Thr | Asn | |
| | 335 | | | | | 340 | | | | | 345 | | | | | |
| CAC | CGA | AAC | CCT | TGG | TTT | CAA | GAA | TTT | TGG | CAG | CAT | CGT | TTT | CAG | TGC | 1464 |
| His | Arg | Asn | Pro | Trp | Phe | Gln | Glu | Phe | Trp | Gln | His | Arg | Phe | Gln | Cys | |
| 350 | | | | | 355 | | | | | 360 | | | | | 365 | |
| CGA | CTG | GAA | GCG | TTT | CCA | CAG | GAG | AAC | AGC | AAA | TAC | AAC | AAG | ACT | TGC | 1512 |
| Arg | Leu | Glu | Ala | Phe | Pro | Gln | Glu | Asn | Ser | Lys | Tyr | Asn | Lys | Thr | Cys | |
| | | | | 370 | | | | | 375 | | | | | 380 | | |
| AAT | AGT | TCT | CTG | ACT | CTG | AAA | ACA | CAT | CAT | GTT | CAG | GAT | TCC | AAA | ATG | 1560 |
| Asn | Ser | Ser | Leu | Thr | Leu | Lys | Thr | His | His | Val | Gln | Asp | Ser | Lys | Met | |

| | | | | | | | | | | | | | | | | |
|---|---|---|---|---|---|---|---|---|---|---|---|---|---|---|---|---|
| | | 385 | | | | | | 390 | | | | | | 395 | | |
| GGA | TTT | GTG | ATC | AAC | GCC | ATC | TAT | TCG | ATG | GCC | TAT | GGG | CTC | CAC | AAC | 1608 |
| Gly | Phe | Val | Ile | Asn | Ala | Ile | Tyr | Ser | Met | Ala | Tyr | Gly | Leu | His | Asn | |
| | | 400 | | | | 405 | | | | | 410 | | | | | |
| ATG | CAG | ATG | TCC | CTC | TGC | CCA | GGC | TAT | GCA | GGA | CTC | TGT | GAT | GCC | ATG | 1656 |
| Met | Gln | Met | Ser | Leu | Cys | Pro | Gly | Tyr | Ala | Gly | Leu | Cys | Asp | Ala | Met | |
| | 415 | | | | 420 | | | | | 425 | | | | | | |
| AAG | CCA | ATT | GAT | GGA | CGG | AAA | CTT | TTG | GAG | TCC | CTG | ATG | AAA | ACC | AAT | 1704 |
| Lys | Pro | Ile | Asp | Gly | Arg | Lys | Leu | Leu | Glu | Ser | Leu | Met | Lys | Thr | Asn | |
| 430 | | | | | 435 | | | | 440 | | | | | 445 | | |
| TTT | ACT | GGG | GTT | TCT | GGA | GAT | ACG | ATC | CTA | TTC | GAT | GAG | AAT | GGA | GAC | 1752 |
| Phe | Thr | Gly | Val | Ser | Gly | Asp | Thr | Ile | Leu | Phe | Asp | Glu | Asn | Gly | Asp | |
| | | | | 450 | | | | | 455 | | | | | 460 | | |
| TCT | CCA | GGA | AGG | TAT | GAA | ATA | ATG | AAT | TTC | AAG | GAA | ATG | GGA | AAA | GAT | 1800 |
| Ser | Pro | Gly | Arg | Tyr | Glu | Ile | Met | Asn | Phe | Lys | Glu | Met | Gly | Lys | Asp | |
| | | | 465 | | | | 470 | | | | | 475 | | | | |
| TAC | TTT | GAT | TAT | ATC | AAC | GTT | GGA | AGT | TGG | GAC | AAT | GGA | GAA | TTA | AAA | 1848 |
| Tyr | Phe | Asp | Tyr | Ile | Asn | Val | Gly | Ser | Trp | Asp | Asn | Gly | Glu | Leu | Lys | |
| | | 480 | | | | | 485 | | | | | 490 | | | | |
| ATG | GAT | GAT | GAT | GAA | GTA | TGG | TCC | AAG | AAA | AGC | AAC | ATC | ATC | AGA | TCT | 1896 |
| Met | Asp | Asp | Asp | Glu | Val | Trp | Ser | Lys | Lys | Ser | Asn | Ile | Ile | Arg | Ser | |
| | 495 | | | | | 500 | | | | | 505 | | | | | |
| GTG | TGC | AGT | GAA | CCA | TGT | GAG | AAA | GGC | CAG | ATC | AAG | GTG | ATC | CGA | AAG | 1944 |
| Val | Cys | Ser | Glu | Pro | Cys | Glu | Lys | Gly | Gln | Ile | Lys | Val | Ile | Arg | Lys | |
| 510 | | | | | 515 | | | | | 520 | | | | | 525 | |
| GGA | GAA | GTC | AGC | TGT | TGT | TGG | ACC | TGT | ACA | CCT | TGT | AAG | GAG | AAT | GAG | 1992 |
| Gly | Glu | Val | Ser | Cys | Cys | Trp | Thr | Cys | Thr | Pro | Cys | Lys | Glu | Asn | Glu | |
| | | | | 530 | | | | | 535 | | | | | 540 | | |
| TAT | GTC | TTT | GAT | GAG | TAC | ACA | TGC | AAG | GCA | TGC | CAA | CTG | GGG | TCT | TGG | 2040 |
| Tyr | Val | Phe | Asp | Glu | Tyr | Thr | Cys | Lys | Ala | Cys | Gln | Leu | Gly | Ser | Trp | |
| | | | 545 | | | | | 550 | | | | | 555 | | | |
| CCC | ACT | GAT | GAT | CTC | ACA | GGT | TGT | GAC | TTG | ATC | CCA | GTA | CAG | TAT | CTT | 2088 |
| Pro | Thr | Asp | Asp | Leu | Thr | Gly | Cys | Asp | Leu | Ile | Pro | Val | Gln | Tyr | Leu | |
| | | 560 | | | | | 565 | | | | | 570 | | | | |
| CGA | TGG | GGT | GAC | CCT | GAA | CCC | ATT | GCA | GCT | GTG | GTG | TTT | GCC | TGC | CTT | 2136 |
| Arg | Trp | Gly | Asp | Pro | Glu | Pro | Ile | Ala | Ala | Val | Val | Phe | Ala | Cys | Leu | |
| 575 | | | | | 580 | | | | | 585 | | | | | | |
| GGC | CTC | CTG | GCC | ACC | CTG | TTT | GTT | ACT | GTA | GTC | TTC | ATC | ATT | TAC | CGT | 2184 |
| Gly | Leu | Leu | Ala | Thr | Leu | Phe | Val | Thr | Val | Val | Phe | Ile | Ile | Tyr | Arg | |
| 590 | | | | | 595 | | | | | 600 | | | | | 605 | |
| GAT | ACA | CCA | GTA | GTC | AAG | TCC | TCA | AGC | AGG | GAA | CTC | TGC | TAC | ATT | ATC | 2232 |
| Asp | Thr | Pro | Val | Val | Lys | Ser | Ser | Ser | Arg | Glu | Leu | Cys | Tyr | Ile | Ile | |
| | | | | 610 | | | | | 615 | | | | | 620 | | |
| CTT | GCT | GGC | ATC | TGC | CTG | GGC | TAC | TTA | TGT | ACC | TTC | TGC | CTC | ATT | GCG | 2280 |
| Leu | Ala | Gly | Ile | Cys | Leu | Gly | Tyr | Leu | Cys | Thr | Phe | Cys | Leu | Ile | Ala | |
| | | | 625 | | | | | 630 | | | | | 635 | | | |
| AAG | CCC | AAA | CAG | ATT | TAC | TGC | TAC | CTT | CAG | AGA | ATT | GGC | ATT | GGT | CTC | 2328 |
| Lys | Pro | Lys | Gln | Ile | Tyr | Cys | Tyr | Leu | Gln | Arg | Ile | Gly | Ile | Gly | Leu | |
| | | 640 | | | | 645 | | | | | 650 | | | | | |
| TCC | CCA | GCC | ATG | AGC | TAC | TCA | GCC | CTT | GTA | ACA | AAG | ACC | AAC | CGT | ATT | 2376 |
| Ser | Pro | Ala | Met | Ser | Tyr | Ser | Ala | Leu | Val | Thr | Lys | Thr | Asn | Arg | Ile | |
| 655 | | | | | 660 | | | | | 665 | | | | | | |
| GCA | AGG | ATC | CTG | GCT | GGC | AGC | AAG | AAG | AAG | ATC | TGT | ACC | CCC | AAG | CCC | 2424 |
| Ala | Arg | Ile | Leu | Ala | Gly | Ser | Lys | Lys | Lys | Ile | Cys | Thr | Pro | Lys | Pro | |
| 670 | | | | 675 | | | | | 680 | | | | | 685 | | |
| AGA | TTC | ATG | AGT | GCC | TGT | GCC | CAG | CTA | GTG | ATT | GCT | TTC | ATT | CTC | ATA | 2472 |
| Arg | Phe | Met | Ser | Ala | Cys | Ala | Gln | Leu | Val | Ile | Ala | Phe | Ile | Leu | Ile | |
| | | | | 690 | | | | | 695 | | | | | 700 | | |
| TGC | ATC | CAG | TTG | GGC | ATC | ATC | GTT | GCC | CTC | TTT | ATA | ATG | GAG | CCT | CCT | 2520 |
| Cys | Ile | Gln | Leu | Gly | Ile | Ile | Val | Ala | Leu | Phe | Ile | Met | Glu | Pro | Pro | |

|   |   |   |   |   |   |   |   |   |   |   |   |   |   |   |   |      |
|---|---|---|---|---|---|---|---|---|---|---|---|---|---|---|---|------|
|   |   |   | 705 |   |   |   |   |   | 710 |   |   |   |   | 715 |   |      |
| GAC | ATA | ATG | CAT | GAC | TAC | CCA | AGC | ATT | CGA | GAA | GTC | TAC | CTG | ATC | TGT | 2568 |
| Asp | Ile | Met | His | Asp | Tyr | Pro | Ser | Ile | Arg | Glu | Val | Tyr | Leu | Ile | Cys |      |
|     |     | 720 |     |     |     |     | 725 |     |     |     |     | 730 |     |     |     |      |
| AAC | ACC | ACC | AAC | CTA | GGA | GTT | GTC | ACT | CCA | CTT | GGA | AAC | AAT | GGA | TTG | 2616 |
| Asn | Thr | Thr | Asn | Leu | Gly | Val | Val | Thr | Pro | Leu | Gly | Asn | Asn | Gly | Leu |      |
|     | 735 |     |     |     |     | 740 |     |     |     |     |     | 745 |     |     |     |      |
| TTG | ATT | TTG | AGC | TGC | ACC | TTC | TAT | GCG | TTC | AAG | ACC | AGA | AAT | GTT | CCA | 2664 |
| Leu | Ile | Leu | Ser | Cys | Thr | Phe | Tyr | Ala | Phe | Lys | Thr | Arg | Asn | Val | Pro |      |
| 750 |     |     |     |     | 755 |     |     |     |     | 760 |     |     |     |     | 765 |      |
| GCT | AAC | TTC | CCC | GAG | GCC | AAG | TAT | ATC | GCC | CTC | ACA | ATG | TAC | ACG | ACC | 2712 |
| Ala | Asn | Phe | Pro | Glu | Ala | Lys | Tyr | Ile | Ala | Leu | Thr | Met | Tyr | Thr | Thr |      |
|     |     |     |     | 770 |     |     |     |     | 775 |     |     |     |     | 780 |     |      |
| TGC | ATT | AAA | TGG | CTA | GCT | TTT | GTT | CCA | ATC | TAC | TTT | GGC | AGC | AAC | TAC | 2760 |
| Cys | Ile | Lys | Trp | Leu | Ala | Phe | Val | Pro | Ile | Tyr | Phe | Gly | Ser | Asn | Tyr |      |
|     |     |     | 785 |     |     |     |     | 790 |     |     |     |     | 795 |     |     |      |
| AAA | ATC | ATC | ACC | ATG | TGT | TTC | TCG | GTC | AGC | CTC | AGT | GCC | ACA | GTG | GCC | 2808 |
| Lys | Ile | Ile | Thr | Met | Cys | Phe | Ser | Val | Ser | Leu | Ser | Ala | Thr | Val | Ala |      |
|     |     | 800 |     |     |     |     | 805 |     |     |     |     | 810 |     |     |     |      |
| CTA | GGC | TGC | ATG | TTT | GTG | CCG | ACG | GTG | TAC | ATC | ATC | CTG | GCC | AAA | CCA | 2856 |
| Leu | Gly | Cys | Met | Phe | Val | Pro | Thr | Val | Tyr | Ile | Ile | Leu | Ala | Lys | Pro |      |
|     | 815 |     |     |     |     | 820 |     |     |     |     | 825 |     |     |     |     |      |
| GAG | AGA | AAC | GTG | CGC | AGC | GCC | TTC | ACC | ACA | TCT | ACC | GTG | GTG | CGC | ATG | 2904 |
| Glu | Arg | Asn | Val | Arg | Ser | Ala | Phe | Thr | Thr | Ser | Thr | Val | Val | Arg | Met |      |
| 830 |     |     |     |     | 835 |     |     |     |     | 840 |     |     |     |     | 845 |      |
| CAT | GTA | GGG | GAT | GGC | AAG | TCA | TCC | TCC | GCA | GCC | AGC | AGA | TCC | AGC | AGC | 2952 |
| His | Val | Gly | Asp | Gly | Lys | Ser | Ser | Ser | Ala | Ala | Ser | Arg | Ser | Ser | Ser |      |
|     |     |     |     | 850 |     |     |     |     | 855 |     |     |     |     | 860 |     |      |
| CTA | GTC | AAC | CTG | TGG | AAG | AGA | AGG | GGC | TCC | TCT | GGG | GAA | ACC | TTA | AGG | 3000 |
| Leu | Val | Asn | Leu | Trp | Lys | Arg | Arg | Gly | Ser | Ser | Gly | Glu | Thr | Leu | Arg |      |
|     |     |     | 865 |     |     |     |     | 870 |     |     |     |     | 875 |     |     |      |

| | |
|---|---|
| TAAAAGTTGT GGGGGCTTAC AGGGATGCTG GCCCCTAAAA CTGGAGCAGA GGCATGTGTT | 3060 |
| TCCTGGGTCT TTTAAATGGG AGAAATCTGG GTAAATGACA CCATCTGAGG CAGGGTGACT | 3120 |
| TACGGCATGG ACCTCCTCAT AAAATGGTAT TTATGGGGTT AATGGGATGT GGCTCCACTT | 3180 |
| ACTTAGCCCA AGTCTAGAAA CATGGAAGTC AAACTCTCTA ATAAAGCAGA GCTACAGCGT | 3240 |
| CGGGGGAGTG ACGTTGACA GGGCAGACAG ACCAGAGTTC AG | 3282 |

( 2 ) INFORMATION FOR SEQ ID NO:12:

( i ) SEQUENCE CHARACTERISTICS:
        ( A ) LENGTH: 877 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

| | | | | | | | | | | | | | | |
|---|---|---|---|---|---|---|---|---|---|---|---|---|---|---|
| Met | Val | Leu | Leu | Leu | Ile | Leu | Ser | Val | Leu | Leu | Trp | Lys | Glu | Asp | Val |
| 1 |     |     |     | 5 |     |     |     |     | 10 |     |     |     |     | 15 |     |
| Arg | Gly | Ser | Ala | Gln | Ser | Ser | Glu | Arg | Arg | Val | Val | Ala | His | Met | Pro |
|     |     |     | 20 |     |     |     |     | 25 |     |     |     |     | 30 |     |     |
| Gly | Asp | Ile | Ile | Ile | Gly | Ala | Leu | Phe | Ser | Val | His | His | Gln | Pro | Thr |
|     |     |     | 35 |     |     |     |     | 40 |     |     |     |     | 45 |     |     |
| Val | Asp | Lys | Val | His | Glu | Arg | Lys | Cys | Gly | Ala | Val | Arg | Glu | Gln | Tyr |
|     | 50 |     |     |     |     | 55 |     |     |     |     | 60 |     |     |     |     |
| Gly | Ile | Gln | Arg | Val | Glu | Ala | Met | Leu | His | Thr | Leu | Glu | Arg | Ile | Asn |
| 65 |     |     |     |     | 70 |     |     |     |     | 75 |     |     |     |     | 80 |
| Ser | Asp | Pro | Thr | Leu | Leu | Pro | Asn | Ile | Thr | Leu | Gly | Cys | Glu | Ile | Arg |

```
                          85                              90                              95
Asp  Ser  Cys  Trp  His  Ser  Ala  Val  Ala  Leu  Glu  Gln  Ser  Ile  Glu  Phe
               100                      105                      110

Ile  Arg  Asp  Ser  Leu  Ile  Ser  Ser  Glu  Glu  Glu  Glu  Gly  Leu  Val  Arg
               115                      120                      125

Cys  Val  Asp  Gly  Ser  Ser  Ser  Ser  Phe  Arg  Ser  Lys  Lys  Pro  Ile  Val
               130                      135                      140

Gly  Val  Ile  Gly  Pro  Gly  Ser  Ser  Ser  Val  Ala  Ile  Gln  Val  Gln  Asn
145                           150                      155                      160

Leu  Leu  Gln  Leu  Phe  Asn  Ile  Pro  Gln  Ile  Ala  Tyr  Ser  Ala  Thr  Ser
                         165                      170                      175

Met  Asp  Leu  Ser  Asp  Lys  Thr  Leu  Phe  Lys  Tyr  Phe  Met  Arg  Val  Val
               180                      185                      190

Pro  Ser  Asp  Ala  Gln  Gln  Ala  Arg  Ala  Met  Val  Asp  Ile  Val  Lys  Arg
               195                      200                      205

Tyr  Asn  Trp  Thr  Tyr  Val  Ser  Ala  Val  His  Thr  Glu  Gly  Asn  Tyr  Gly
          210                      215                      220

Glu  Ser  Gly  Met  Glu  Ala  Ser  Lys  Asp  Met  Ser  Ala  Lys  Glu  Gly  Ile
225                           230                      235                      240

Cys  Ile  Ala  His  Ser  Tyr  Lys  Ile  Tyr  Ser  Asn  Ala  Gly  Glu  Gln  Ser
                    245                      250                      255

Phe  Asp  Lys  Leu  Leu  Lys  Lys  Leu  Thr  Ser  His  Leu  Pro  Lys  Ala  Arg
               260                      265                      270

Val  Val  Ala  Cys  Phe  Cys  Glu  Gly  Met  Thr  Val  Arg  Gly  Leu  Leu  Met
               275                      280                      285

Ala  Met  Arg  Arg  Leu  Gly  Leu  Ala  Gly  Glu  Phe  Leu  Leu  Leu  Gly  Ser
          290                      295                      300

Asp  Gly  Trp  Ala  Asp  Arg  Tyr  Asp  Val  Thr  Asp  Gly  Tyr  Gln  Arg  Glu
305                           310                      315                      320

Ala  Val  Gly  Gly  Ile  Thr  Ile  Lys  Leu  Gln  Ser  Pro  Asp  Val  Lys  Trp
                    325                      330                      335

Phe  Asp  Asp  Tyr  Tyr  Leu  Lys  Leu  Arg  Pro  Glu  Thr  Asn  His  Arg  Asn
               340                      345                      350

Pro  Trp  Phe  Gln  Glu  Phe  Trp  Gln  His  Arg  Phe  Gln  Cys  Arg  Leu  Glu
          355                      360                      365

Ala  Phe  Pro  Gln  Glu  Asn  Ser  Lys  Tyr  Asn  Lys  Thr  Cys  Asn  Ser  Ser
     370                      375                      380

Leu  Thr  Leu  Lys  Thr  His  His  Val  Gln  Asp  Ser  Lys  Met  Gly  Phe  Val
385                      390                      395                           400

Ile  Asn  Ala  Ile  Tyr  Ser  Met  Ala  Tyr  Gly  Leu  His  Asn  Met  Gln  Met
                    405                      410                      415

Ser  Leu  Cys  Pro  Gly  Tyr  Ala  Gly  Leu  Cys  Asp  Ala  Met  Lys  Pro  Ile
               420                      425                      430

Asp  Gly  Arg  Lys  Leu  Leu  Glu  Ser  Leu  Met  Lys  Thr  Asn  Phe  Thr  Gly
          435                      440                      445

Val  Ser  Gly  Asp  Thr  Ile  Leu  Phe  Asp  Glu  Asn  Gly  Asp  Ser  Pro  Gly
     450                      455                      460

Arg  Tyr  Glu  Ile  Met  Asn  Phe  Lys  Glu  Met  Gly  Lys  Asp  Tyr  Phe  Asp
465                      470                      475                           480

Tyr  Ile  Asn  Val  Gly  Ser  Trp  Asp  Asn  Gly  Glu  Leu  Lys  Met  Asp  Asp
                    485                      490                      495

Asp  Glu  Val  Trp  Ser  Lys  Lys  Ser  Asn  Ile  Ile  Arg  Ser  Val  Cys  Ser
               500                      505                      510
```

```
Glu  Pro  Cys  Glu  Lys  Gly  Gln  Ile  Lys  Val  Ile  Arg  Lys  Gly  Glu  Val
          515                 520                           525

Ser  Cys  Cys  Trp  Thr  Cys  Thr  Pro  Cys  Lys  Glu  Asn  Glu  Tyr  Val  Phe
          530                 535                           540

Asp  Glu  Tyr  Thr  Cys  Lys  Ala  Cys  Gln  Leu  Gly  Ser  Trp  Pro  Thr  Asp
545                           550                 555                           560

Asp  Leu  Thr  Gly  Cys  Asp  Leu  Ile  Pro  Val  Gln  Tyr  Leu  Arg  Trp  Gly
                    565                      570                           575

Asp  Pro  Glu  Pro  Ile  Ala  Ala  Val  Val  Phe  Ala  Cys  Leu  Gly  Leu  Leu
               580                      585                      590

Ala  Thr  Leu  Phe  Val  Thr  Val  Val  Phe  Ile  Ile  Tyr  Arg  Asp  Thr  Pro
          595                 600                           605

Val  Val  Lys  Ser  Ser  Ser  Arg  Glu  Leu  Cys  Tyr  Ile  Ile  Leu  Ala  Gly
     610                      615                      620

Ile  Cys  Leu  Gly  Tyr  Leu  Cys  Thr  Phe  Cys  Leu  Ile  Ala  Lys  Pro  Lys
625                      630                 635                           640

Gln  Ile  Tyr  Cys  Tyr  Leu  Gln  Arg  Ile  Gly  Ile  Gly  Leu  Ser  Pro  Ala
                    645                      650                      655

Met  Ser  Tyr  Ser  Ala  Leu  Val  Thr  Lys  Thr  Asn  Arg  Ile  Ala  Arg  Ile
               660                 665                      670

Leu  Ala  Gly  Ser  Lys  Lys  Lys  Ile  Cys  Thr  Pro  Lys  Pro  Arg  Phe  Met
               675                 680                 685

Ser  Ala  Cys  Ala  Gln  Leu  Val  Ile  Ala  Phe  Ile  Leu  Ile  Cys  Ile  Gln
     690                      695                      700

Leu  Gly  Ile  Ile  Val  Ala  Leu  Phe  Ile  Met  Glu  Pro  Pro  Asp  Ile  Met
705                      710                 715                           720

His  Asp  Tyr  Pro  Ser  Ile  Arg  Glu  Val  Tyr  Leu  Ile  Cys  Asn  Thr  Thr
                    725                 730                           735

Asn  Leu  Gly  Val  Val  Thr  Pro  Leu  Gly  Asn  Asn  Gly  Leu  Leu  Ile  Leu
               740                 745                      750

Ser  Cys  Thr  Phe  Tyr  Ala  Phe  Lys  Thr  Arg  Asn  Val  Pro  Ala  Asn  Phe
          755                 760                      765

Pro  Glu  Ala  Lys  Tyr  Ile  Ala  Leu  Thr  Met  Tyr  Thr  Thr  Cys  Ile  Lys
     770                 775                      780

Trp  Leu  Ala  Phe  Val  Pro  Ile  Tyr  Phe  Gly  Ser  Asn  Tyr  Lys  Ile  Ile
785                      790                 795                           800

Thr  Met  Cys  Phe  Ser  Val  Ser  Leu  Ser  Ala  Thr  Val  Ala  Leu  Gly  Cys
               805                      810                      815

Met  Phe  Val  Pro  Thr  Val  Tyr  Ile  Ile  Leu  Ala  Lys  Pro  Glu  Arg  Asn
               820                 825                 830

Val  Arg  Ser  Ala  Phe  Thr  Thr  Ser  Thr  Val  Val  Arg  Met  His  Val  Gly
          835                      840                      845

Asp  Gly  Lys  Ser  Ser  Ser  Ala  Ala  Ser  Arg  Ser  Ser  Ser  Leu  Val  Asn
     850                      855                      860

Leu  Trp  Lys  Arg  Arg  Gly  Ser  Ser  Gly  Glu  Thr  Leu  Arg
865                      870                 875
```

( 2 ) INFORMATION FOR SEQ ID NO:13:

( i ) SEQUENCE CHARACTERISTICS:
        ( A ) LENGTH: 343 base pairs
        ( B ) TYPE: nucleic acid
        ( C ) STRANDEDNESS: both
        ( D ) TOPOLOGY: both ( i i ) MOLECULE TYPE: cDNA ( i x ) FEATURE:
    ( A ) NAME/KEY: misc_feature
    ( B ) LOCATION: 1..343
    ( D ) OTHER INFORMATION: /note="Partial sequence of MGLUR2
        3'untranslated sequence."

( x i ) SEQUENCE DESCRIPTION: SEQ ID NO:13:

| | | | | | | |
|---|---|---|---|---|---|---|
| TGGAGACGCC | ATACTGCCGC | GCTGACACAG | CTGCTCCTGG | GCACCTAGTG | CAGACCCACG | 60 |
| TCCAGGGCCA | GGAGGAAGTT | GGCTGGAGCA | CTGCAATAAT | TTATTACCCA | GCCTATGTCT | 120 |
| GCCCCCCGAG | TCACTTACCC | ACCTCCTTAC | CCCAGCTCTT | CAGACTCAGA | AGTCAGGAGC | 180 |
| CTTGGCCAGG | AGCCTCTGCA | GTGGCCACTA | ACTGCCCTTG | TAGCTGTGTT | TCCTCCTGGC | 240 |
| CAGGCCCAGG | GCTCAGAGAG | GAGCAAGCCA | GGGTTCACTC | TGCCCTGGAC | CCGGGTGGCT | 300 |
| GAGGACGGCA | GGCCCCAGTC | CTAACCAGCA | AAGGTGCTTC | CAG | | 343 |